United States Patent
Dubridge et al.

(10) Patent No.: US 11,623,958 B2
(45) Date of Patent: *Apr. 11, 2023

(54) SINGLE CHAIN VARIABLE FRAGMENT CD3 BINDING PROTEINS

(71) Applicant: Harpoon Therapeutics, Inc., South San Francisco, CA (US)

(72) Inventors: Robert B. Dubridge, Belmont, CA (US); Pui Seto, San Carlos, CA (US); Richard J. Austin, San Francisco, CA (US); Luke Evnin, San Francisco, CA (US); Jeanmarie Guenot, San Francisco, CA (US); Bryan Lemon, Mountain View, CA (US)

(73) Assignee: HARPOON THERAPEUTICS, INC., South San Francisco, CA (US)

( * ) Notice: Subject to any disclaimer, the term of this patent is extended or adjusted under 35 U.S.C. 154(b) by 601 days.

This patent is subject to a terminal disclaimer.

(21) Appl. No.: 16/773,806

(22) Filed: Jan. 27, 2020

(65) Prior Publication Data
US 2020/0231672 A1    Jul. 23, 2020

Related U.S. Application Data

(63) Continuation-in-part of application No. 15/600,264, filed on May 19, 2017, now Pat. No. 10,544,221.

(60) Provisional application No. 62/339,685, filed on May 20, 2016.

(51) Int. Cl.
C07K 16/28    (2006.01)
C07K 16/18    (2006.01)

(52) U.S. Cl.
CPC .......... *C07K 16/2809* (2013.01); *C07K 16/18* (2013.01); *C07K 16/2887* (2013.01); *C07K 2317/31* (2013.01); *C07K 2317/565* (2013.01); *C07K 2317/622* (2013.01); *C07K 2317/73* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. |
| 4,943,533 A | 7/1990 | Mendelsohn et al. |
| 5,061,620 A | 10/1991 | Tsukamoto et al. |
| 5,199,942 A | 4/1993 | Gillis |
| 5,225,539 A | 7/1993 | Winter |
| 5,350,674 A | 9/1994 | Boenisch et al. |
| 5,399,346 A | 3/1995 | Anderson et al. |
| 5,530,101 A | 6/1996 | Queen et al. |
| 5,565,332 A | 10/1996 | Hoogenboom et al. |
| 5,580,859 A | 12/1996 | Felgner et al. |
| 5,585,089 A | 12/1996 | Queen et al. |
| 5,585,362 A | 12/1996 | Wilson et al. |
| 5,589,466 A | 12/1996 | Felgner et al. |
| 5,759,808 A | 6/1998 | Casterman et al. |
| 5,766,886 A | 6/1998 | Studnicka et al. |
| 5,773,292 A | 6/1998 | Bander |
| 5,800,988 A | 9/1998 | Casterman et al. |
| 5,811,097 A | 9/1998 | Allison et al. |
| 5,840,526 A | 11/1998 | Casterman et al. |
| 5,843,439 A | 12/1998 | Anderson et al. |
| 5,844,093 A | 12/1998 | Kettleborough et al. |
| 5,858,358 A | 1/1999 | June et al. |
| 5,859,205 A | 1/1999 | Adair et al. |
| 5,874,541 A | 2/1999 | Casterman et al. |
| 5,883,223 A | 3/1999 | Gray |
| 5,977,318 A | 11/1999 | Linsley et al. |
| 6,005,079 A | 12/1999 | Casterman et al. |
| 6,015,695 A | 1/2000 | Casterman et al. |
| 6,051,227 A | 4/2000 | Allison et al. |
| 6,107,090 A | 8/2000 | Bander |
| 6,120,766 A | 9/2000 | Hale et al. |
| 6,136,311 A | 10/2000 | Bander |
| 6,210,669 B1 | 4/2001 | Aruffo et al. |
| 6,303,121 B1 | 10/2001 | Kwon |
| 6,326,193 B1 | 12/2001 | Liu et al. |
| 6,331,415 B1 | 12/2001 | Cabilly et al. |
| 6,352,694 B1 | 3/2002 | June et al. |
| 6,355,476 B1 | 3/2002 | Kwon et al. |
| 6,362,325 B1 | 3/2002 | Kwon |
| 6,407,213 B1 | 6/2002 | Carter et al. |
| 6,534,055 B1 | 3/2003 | June et al. |

(Continued)

FOREIGN PATENT DOCUMENTS

| | | |
|---|---|---|
| CN | 1563092 A | 1/2005 |
| CN | 101646689 A | 2/2010 |

(Continued)

OTHER PUBLICATIONS

Annual Report Pursuant to Section 13 or 15(d) of the Securities Exchange Act of 1934. 2019 22-24 [online]. [Retrieved on Aug. 5, 2021], Retrieved from website URL:https://www.annualreports.com/HostedData/AnnualReportArchive/h/NASDAQ_HARP_2018.pdf.

Brauchle et al. Characterization of a Novel FLT3 BiTE Molecule for the Treatment of Acute Myeloid Leukemia. Mol Cancer Ther 19:1875-88 (2020).

Glaser et al. Novel antibody hinge regions for efficient production of CH2 domain-deleted antibodies. J. Biol. Chem. 280:41494-503 (2005).

(Continued)

*Primary Examiner* — Zachary S Skelding
(74) *Attorney, Agent, or Firm* — Wilson Sonsini Goodrich & Rosati

(57) ABSTRACT

Disclosed herein are single chain variable fragment CD3 binding proteins with improved binding affinities, and robust aggregation profiles. Also described are multispecific binding proteins comprising a single chain variable fragment CD3 binding protein according to the instant disclosure. Pharmaceutical compositions comprising the binding proteins disclosed herein and methods of using such formulations are provided.

24 Claims, 4 Drawing Sheets

Specification includes a Sequence Listing.

(56) References Cited

U.S. PATENT DOCUMENTS

| | | |
|---|---|---|
| 6,548,640 B1 | 4/2003 | Winter |
| 6,569,997 B1 | 5/2003 | Kwon |
| 6,670,453 B2 | 12/2003 | Frenken et al. |
| 6,682,736 B1 | 1/2004 | Hanson et al. |
| 6,692,964 B1 | 2/2004 | June et al. |
| 6,759,518 B1 | 7/2004 | Kontermann et al. |
| 6,767,711 B2 | 7/2004 | Bander |
| 6,797,514 B2 | 9/2004 | Berenson et al. |
| 6,808,710 B1 | 10/2004 | Wood et al. |
| 6,867,041 B2 | 3/2005 | Berenson et al. |
| 6,887,466 B2 | 5/2005 | June et al. |
| 6,887,673 B2 | 5/2005 | Kunkel et al. |
| 6,905,680 B2 | 6/2005 | June et al. |
| 6,905,681 B1 | 6/2005 | June et al. |
| 6,905,685 B2 | 6/2005 | Kwon |
| 6,905,874 B2 | 6/2005 | Berenson et al. |
| 6,974,863 B2 | 12/2005 | Kwon |
| 6,984,720 B1 | 1/2006 | Korman et al. |
| 7,034,121 B2 | 4/2006 | Carreno et al. |
| 7,060,808 B1 | 6/2006 | Goldstein et al. |
| 7,067,318 B2 | 6/2006 | June et al. |
| 7,144,575 B2 | 12/2006 | June et al. |
| 7,163,680 B2 | 1/2007 | Bander |
| 7,172,869 B2 | 2/2007 | June et al. |
| 7,175,843 B2 | 2/2007 | June et al. |
| 7,214,493 B2 | 5/2007 | Kunkel et al. |
| 7,232,566 B2 | 6/2007 | June et al. |
| 7,247,301 B2 | 7/2007 | Van De Winkel et al. |
| 7,262,276 B2 | 8/2007 | Huang et al. |
| 7,288,638 B2 | 10/2007 | Jure-Kunkel et al. |
| 7,488,802 B2 | 2/2009 | Collins et al. |
| 7,595,378 B2 | 9/2009 | Van De Winkel et al. |
| 7,605,238 B2 | 10/2009 | Korman et al. |
| 7,666,414 B2 | 2/2010 | Bander |
| 7,723,484 B2 | 5/2010 | Beidler et al. |
| 7,807,162 B2 | 10/2010 | Silence |
| 7,812,135 B2 | 10/2010 | Smith et al. |
| 7,850,971 B2 | 12/2010 | Maddon et al. |
| 7,939,072 B2 | 5/2011 | Yarden et al. |
| 7,943,743 B2 | 5/2011 | Korman et al. |
| 8,008,449 B2 | 8/2011 | Korman et al. |
| 8,114,965 B2 | 2/2012 | Maddon et al. |
| 8,153,768 B2 | 4/2012 | Kunz et al. |
| 8,168,757 B2 | 5/2012 | Finnefrock et al. |
| 8,188,223 B2 | 5/2012 | Beirnaert et al. |
| 8,236,308 B2 | 8/2012 | Kischel et al. |
| 8,354,509 B2 | 1/2013 | Carven et al. |
| 8,388,967 B2 | 3/2013 | Smith et al. |
| 8,470,330 B2 | 6/2013 | Schuelke et al. |
| 8,552,156 B2 | 10/2013 | Takayanagi et al. |
| 8,609,089 B2 | 12/2013 | Langermann et al. |
| 8,623,356 B2 | 1/2014 | Christopherson et al. |
| 8,629,244 B2 | 1/2014 | Kolkman et al. |
| 8,703,135 B2 | 4/2014 | Beste et al. |
| 8,709,424 B2 | 4/2014 | Schebye et al. |
| 8,779,105 B2 | 7/2014 | Korman et al. |
| 8,784,821 B1 | 7/2014 | Kufer et al. |
| 8,846,042 B2 | 9/2014 | Zhou |
| 8,900,587 B2 | 12/2014 | Carven et al. |
| 8,907,071 B2 | 12/2014 | Sullivan et al. |
| 8,937,164 B2 | 1/2015 | Descamps et al. |
| 9,126,984 B2 | 9/2015 | Crosignani et al. |
| 9,169,316 B2 | 10/2015 | Baty et al. |
| 9,309,327 B2 | 4/2016 | Humphreys et al. |
| 9,327,022 B2 | 5/2016 | Zhang et al. |
| 9,340,621 B2 | 5/2016 | Kufer et al. |
| 9,359,442 B2 | 6/2016 | Hoffee et al. |
| 9,422,368 B2 | 8/2016 | Spee et al. |
| 9,624,185 B1 | 4/2017 | Xu |
| 9,642,918 B2 | 5/2017 | Bruederle et al. |
| 9,708,412 B2 | 7/2017 | Baeuerle et al. |
| 9,920,115 B2 | 3/2018 | Dubridge et al. |
| 10,066,016 B2 | 9/2018 | Dubridge et al. |
| 10,100,106 B2 | 10/2018 | Dubridge et al. |
| 10,428,120 B2 | 10/2019 | Kontermann et al. |
| 10,543,271 B2 | 1/2020 | Wesche et al. |
| 10,544,221 B2 | 1/2020 | Dubridge et al. |
| 11,180,563 B2 | 11/2021 | Wesche et al. |
| 2002/0015704 A1 | 2/2002 | Bander |
| 2002/0051780 A1 | 5/2002 | Lindhofer et al. |
| 2003/0031673 A1 | 2/2003 | Bander |
| 2003/0092892 A1 | 5/2003 | Frenken et al. |
| 2004/0101519 A1 | 5/2004 | June et al. |
| 2005/0042664 A1 | 2/2005 | Wu et al. |
| 2005/0048617 A1 | 3/2005 | Wu et al. |
| 2005/0095244 A1 | 5/2005 | Jure-Kunkel et al. |
| 2005/0100543 A1 | 5/2005 | Hansen et al. |
| 2005/0175606 A1 | 8/2005 | Huang et al. |
| 2006/0034810 A1 | 2/2006 | Riley et al. |
| 2006/0046971 A1 | 3/2006 | Stuhler et al. |
| 2006/0121005 A1 | 6/2006 | Berenson et al. |
| 2006/0228364 A1 | 10/2006 | Dennis et al. |
| 2006/0252096 A1 | 11/2006 | Zha et al. |
| 2007/0014794 A1 | 1/2007 | Carter et al. |
| 2007/0178082 A1 | 8/2007 | Silence et al. |
| 2007/0269422 A1 | 11/2007 | Beirnaert et al. |
| 2008/0069772 A1 | 3/2008 | Stuhler et al. |
| 2008/0260757 A1 | 10/2008 | Holt et al. |
| 2009/0041789 A1 | 2/2009 | Elsaesser-Beile et al. |
| 2009/0136494 A1 | 5/2009 | Ponath et al. |
| 2009/0259026 A1 | 10/2009 | Tomlinson et al. |
| 2010/0022452 A1 | 1/2010 | Silence |
| 2010/0028330 A1 | 2/2010 | Collins et al. |
| 2010/0122358 A1 | 5/2010 | Brueggemann et al. |
| 2010/0150918 A1 | 6/2010 | Kufer et al. |
| 2010/0166734 A1 | 7/2010 | Dolk |
| 2010/0189651 A1 | 7/2010 | Stagliano et al. |
| 2010/0189727 A1 | 7/2010 | Rodeck et al. |
| 2010/0266531 A1 | 10/2010 | Hsieh et al. |
| 2010/0291112 A1 | 11/2010 | Kellner et al. |
| 2010/0311119 A1 | 12/2010 | Hermans et al. |
| 2011/0129458 A1 | 6/2011 | Dolk et al. |
| 2011/0150892 A1 | 6/2011 | Thudium et al. |
| 2011/0165621 A1 | 7/2011 | Dreier et al. |
| 2011/0262439 A1 | 10/2011 | Kufer et al. |
| 2011/0275787 A1 | 11/2011 | Kufer et al. |
| 2011/0313135 A1 | 12/2011 | Vanhove et al. |
| 2012/0039899 A1 | 2/2012 | Olsen et al. |
| 2012/0039906 A1 | 2/2012 | Olive |
| 2012/0114649 A1 | 5/2012 | Langermann et al. |
| 2012/0231024 A1 | 9/2012 | Elsaesser-Beile et al. |
| 2012/0237977 A1 | 9/2012 | Daugherty et al. |
| 2012/0263677 A1 | 10/2012 | Eagle et al. |
| 2012/0328619 A1 | 12/2012 | Fey et al. |
| 2013/0017199 A1 | 1/2013 | Langermann |
| 2013/0017200 A1 | 1/2013 | Scheer et al. |
| 2013/0136744 A1 | 5/2013 | Bouche et al. |
| 2013/0183321 A1 | 7/2013 | Smith et al. |
| 2013/0197201 A1 | 8/2013 | Vasquez et al. |
| 2013/0266568 A1 | 10/2013 | Brinkmann et al. |
| 2013/0267686 A1 | 10/2013 | Brinkmann et al. |
| 2013/0273055 A1 | 10/2013 | Borges et al. |
| 2013/0330335 A1 | 12/2013 | Bremel et al. |
| 2014/0004121 A1 | 1/2014 | Fanslow, III et al. |
| 2014/0023664 A1 | 1/2014 | Lowman et al. |
| 2014/0044728 A1 | 2/2014 | Takayanagi et al. |
| 2014/0045195 A1 | 2/2014 | Daugherty et al. |
| 2014/0065152 A1 | 3/2014 | Kwon |
| 2014/0072565 A1 | 3/2014 | Kwon |
| 2014/0072566 A1 | 3/2014 | Kwon |
| 2014/0073767 A1 | 3/2014 | Lee et al. |
| 2014/0088295 A1 | 3/2014 | Smith et al. |
| 2014/0093511 A1 | 4/2014 | Lonberg et al. |
| 2014/0205601 A1 | 7/2014 | Beirnaert et al. |
| 2014/0220002 A1 | 8/2014 | Ponte et al. |
| 2014/0242075 A1 | 8/2014 | Parren et al. |
| 2014/0302037 A1 | 10/2014 | Borges et al. |
| 2014/0322218 A1 | 10/2014 | Xiao et al. |
| 2014/0348841 A1 | 11/2014 | Schebye et al. |
| 2015/0037334 A1 | 2/2015 | Kufer et al. |
| 2015/0056206 A1 | 2/2015 | Zhou |
| 2015/0064169 A1 | 3/2015 | Wang et al. |
| 2015/0079088 A1 | 3/2015 | Lowman et al. |
| 2015/0079093 A1 | 3/2015 | Stuhler |

(56) References Cited

U.S. PATENT DOCUMENTS

| | | |
|---|---|---|
| 2015/0079109 A1 | 3/2015 | Li et al. |
| 2015/0093336 A1 | 4/2015 | Van Ginderachter et al. |
| 2015/0174268 A1 | 6/2015 | Li et al. |
| 2015/0183875 A1 | 7/2015 | Cobbold et al. |
| 2015/0225367 A1 | 8/2015 | Crosignani et al. |
| 2015/0232557 A1 | 8/2015 | Tan et al. |
| 2015/0274836 A1 | 10/2015 | Ho et al. |
| 2015/0274844 A1 | 10/2015 | Blankenship et al. |
| 2016/0017058 A1 | 1/2016 | Kim et al. |
| 2016/0024174 A1 | 1/2016 | Odunsi et al. |
| 2016/0032011 A1 | 2/2016 | Zhang et al. |
| 2016/0032019 A1 | 2/2016 | Xiao et al. |
| 2016/0039942 A1 | 2/2016 | Cobbold et al. |
| 2016/0068605 A1 | 3/2016 | Nemeth et al. |
| 2016/0115241 A1 | 4/2016 | Yan et al. |
| 2016/0130331 A1 | 5/2016 | Stull et al. |
| 2016/0215063 A1 | 7/2016 | Bernett et al. |
| 2016/0229913 A1 | 8/2016 | Bosques et al. |
| 2016/0251438 A1 | 9/2016 | Lucas et al. |
| 2016/0251440 A1 | 9/2016 | Roobrouck et al. |
| 2016/0257721 A1 | 9/2016 | Lieber et al. |
| 2016/0263087 A1 | 9/2016 | Crosignani et al. |
| 2016/0319040 A1 | 11/2016 | Dreier et al. |
| 2016/0340444 A1 | 11/2016 | Baeuerle et al. |
| 2016/0355842 A1 | 12/2016 | Parks et al. |
| 2017/0029502 A1 | 2/2017 | Raum et al. |
| 2017/0037149 A1 | 2/2017 | Raum et al. |
| 2017/0152316 A1 | 6/2017 | Cobbold et al. |
| 2017/0158771 A1 | 6/2017 | Glennie et al. |
| 2017/0204164 A1 | 7/2017 | Himmler et al. |
| 2017/0274094 A1 | 9/2017 | Stull et al. |
| 2017/0275373 A1 | 9/2017 | Kufer et al. |
| 2017/0298149 A1 | 10/2017 | Baeuerle et al. |
| 2017/0306014 A1 | 10/2017 | Cornen et al. |
| 2017/0334997 A1 | 11/2017 | Dubridge et al. |
| 2017/0349660 A1 | 12/2017 | Saville et al. |
| 2017/0362310 A1 | 12/2017 | Shoemaker |
| 2017/0369563 A1 | 12/2017 | Dubridge et al. |
| 2018/0016323 A1 | 1/2018 | Brandenburg et al. |
| 2018/0036306 A1 | 2/2018 | Jones et al. |
| 2018/0134789 A1 | 5/2018 | Baeuerle et al. |
| 2018/0148508 A1 | 5/2018 | Wang et al. |
| 2018/0161428 A1 | 6/2018 | Dubridge et al. |
| 2018/0162949 A1 | 6/2018 | Baeuerle et al. |
| 2018/0327508 A1 | 11/2018 | Wesche et al. |
| 2018/0327511 A1 | 11/2018 | Satoh et al. |
| 2018/0346601 A1 | 12/2018 | Dettling et al. |
| 2019/0016811 A1 | 1/2019 | Lucas et al. |
| 2019/0023786 A1 | 1/2019 | Broderick et al. |
| 2019/0031749 A1 | 1/2019 | Dubridge et al. |
| 2019/0062427 A1 | 2/2019 | Rosenthal et al. |
| 2019/0092862 A1 | 3/2019 | Cui et al. |
| 2019/0112381 A1 | 4/2019 | Wesche et al. |
| 2019/0127483 A1 | 5/2019 | Li |
| 2019/0135930 A1 | 5/2019 | Wesche et al. |
| 2019/0225702 A1 | 7/2019 | Baeuerle et al. |
| 2020/0095340 A1 | 3/2020 | Wesche et al. |
| 2020/0115461 A1 | 4/2020 | Evnin et al. |
| 2020/0148771 A1 | 5/2020 | Paeuerle et al. |
| 2020/0155520 A1 | 5/2020 | Colburn et al. |
| 2020/0352998 A1 | 11/2020 | Albertson et al. |
| 2021/0171649 A1 | 6/2021 | Wesche et al. |
| 2021/0179735 A1 | 6/2021 | Baeuerle et al. |
| 2021/0269530 A1 | 9/2021 | Lin et al. |
| 2021/0284728 A1 | 9/2021 | Lin et al. |
| 2021/0292421 A1 | 9/2021 | Lin et al. |
| 2021/0355219 A1 | 11/2021 | Lin et al. |
| 2022/0017626 A1 | 1/2022 | Wesche et al. |
| 2022/0054544 A1 | 2/2022 | Lin et al. |
| 2022/0098311 A1 | 3/2022 | Wesche et al. |
| 2022/0112297 A1 | 4/2022 | Wesche et al. |
| 2022/0267462 A1 | 8/2022 | Wesche et al. |

FOREIGN PATENT DOCUMENTS

| | | |
|---|---|---|
| CN | 105968201 A | 9/2016 |
| CN | 105968204 A | 9/2016 |
| CN | 109593786 A | 4/2019 |
| EP | 0239400 A2 | 9/1987 |
| EP | 0519596 A1 | 12/1992 |
| EP | 0592106 A1 | 4/1994 |
| EP | 1378520 A1 | 1/2004 |
| EP | 1736484 A1 | 12/2006 |
| EP | 2336179 A1 | 6/2011 |
| EP | 2581113 A1 | 4/2013 |
| EP | 3146979 A1 | 3/2017 |
| EP | 3193929 B1 | 6/2019 |
| FR | 901228 A | 7/1945 |
| JP | 2005501517 A | 1/2005 |
| JP | 2005518789 A | 6/2005 |
| JP | 2007535915 A | 12/2007 |
| JP | 2008278814 A | 11/2008 |
| JP | 2015501135 A | 1/2015 |
| JP | 2016500655 A | 1/2016 |
| JP | 2019052750 A | 4/2019 |
| WO | WO-9109967 A1 | 7/1991 |
| WO | WO-9307105 A1 | 4/1993 |
| WO | WO-9404678 A1 | 3/1994 |
| WO | WO-9937681 A2 | 7/1999 |
| WO | WO-0043507 A1 | 7/2000 |
| WO | WO-0130381 A2 | 5/2001 |
| WO | WO-0190190 A2 | 11/2001 |
| WO | WO-0196584 A2 | 12/2001 |
| WO | WO-02055082 A1 | 7/2002 |
| WO | WO-02085945 A2 | 10/2002 |
| WO | WO-03025020 A1 | 3/2003 |
| WO | WO-03035694 A2 | 5/2003 |
| WO | WO-03064606 A2 | 8/2003 |
| WO | WO-2004003019 A2 | 1/2004 |
| WO | WO-2004035607 A2 | 4/2004 |
| WO | WO-2004041867 A2 | 5/2004 |
| WO | WO-2004042404 A1 | 5/2004 |
| WO | WO-2004049794 A2 | 6/2004 |
| WO | WO-2004056312 A2 | 7/2004 |
| WO | WO-2004099249 A2 | 11/2004 |
| WO | WO-2005003168 A2 | 1/2005 |
| WO | WO-2005009465 A1 | 2/2005 |
| WO | WO-2006020258 A2 | 2/2006 |
| WO | WO-2006072625 A2 | 7/2006 |
| WO | WO-2006072626 A1 | 7/2006 |
| WO | WO-2006105021 A2 | 10/2006 |
| WO | WO-2006121168 A1 | 11/2006 |
| WO | WO-2006122787 A1 | 11/2006 |
| WO | WO-2007005874 A2 | 1/2007 |
| WO | WO-2007024715 A2 | 3/2007 |
| WO | WO-2007042261 A2 | 4/2007 |
| WO | WO-2007042573 A2 | 4/2007 |
| WO | WO-2007062466 A1 | 6/2007 |
| WO | WO-2007113648 A2 | 10/2007 |
| WO | WO-2007115230 A2 | 10/2007 |
| WO | WO-2008028977 A2 | 3/2008 |
| WO | WO-2008084106 A1 | 7/2008 |
| WO | WO-2009009116 A2 | 1/2009 |
| WO | WO-2009025846 A2 | 2/2009 |
| WO | WO-2009030285 A1 | 3/2009 |
| WO | WO-2009101611 A1 | 8/2009 |
| WO | WO-2009114335 A2 | 9/2009 |
| WO | WO-2009147248 A2 | 12/2009 |
| WO | WO-2010003118 A1 | 1/2010 |
| WO | WO-2010012557 A1 | 2/2010 |
| WO | WO-2010019570 A2 | 2/2010 |
| WO | WO-2010027827 A2 | 3/2010 |
| WO | WO-2010037836 A2 | 4/2010 |
| WO | WO-2010037837 A2 | 4/2010 |
| WO | WO-2010065939 A1 | 6/2010 |
| WO | WO-2010077634 A1 | 7/2010 |
| WO | WO-2010081173 A2 | 7/2010 |
| WO | WO-2011028683 A1 | 3/2011 |
| WO | WO-2011039368 A2 | 4/2011 |
| WO | WO-2011051327 A2 | 5/2011 |
| WO | WO-2011066342 A2 | 6/2011 |
| WO | WO-2011070024 A1 | 6/2011 |

(56) References Cited

FOREIGN PATENT DOCUMENTS

| | | |
|---|---|---|
| WO | WO-2011107553 A1 | 9/2011 |
| WO | WO-2011117423 A1 | 9/2011 |
| WO | WO-2011131407 A1 | 10/2011 |
| WO | WO-2011140249 A2 | 11/2011 |
| WO | WO-2011155607 A1 | 12/2011 |
| WO | WO-2012071411 A2 | 5/2012 |
| WO | WO-2012122444 A1 | 9/2012 |
| WO | WO-2012131053 A1 | 10/2012 |
| WO | WO-2012138475 A1 | 10/2012 |
| WO | WO-2012145493 A1 | 10/2012 |
| WO | WO-2012158818 A2 | 11/2012 |
| WO | WO-2012160448 A2 | 11/2012 |
| WO | WO-2012163805 A1 | 12/2012 |
| WO | WO-2012175400 A1 | 12/2012 |
| WO | WO-2013006490 A2 | 1/2013 |
| WO | WO-2013036130 A1 | 3/2013 |
| WO | WO-2013039954 A1 | 3/2013 |
| WO | WO-2013072406 A1 | 5/2013 |
| WO | WO-2013072415 A1 | 5/2013 |
| WO | WO-2013079174 A1 | 6/2013 |
| WO | WO-2013087699 A1 | 6/2013 |
| WO | WO-2013104804 A2 | 7/2013 |
| WO | WO-2013110531 A1 | 8/2013 |
| WO | WO-2013119716 A1 | 8/2013 |
| WO | WO-2013126712 A1 | 8/2013 |
| WO | WO-2013128027 A1 | 9/2013 |
| WO | WO-2013128194 A1 | 9/2013 |
| WO | WO-2013132044 A1 | 9/2013 |
| WO | WO-2013169264 A1 | 11/2013 |
| WO | WO-2013173223 A1 | 11/2013 |
| WO | WO-2014008218 A1 | 1/2014 |
| WO | WO-2014033304 A2 | 3/2014 |
| WO | WO-2014036357 A1 | 3/2014 |
| WO | WO-2014047231 A1 | 3/2014 |
| WO | WO-2014052064 A1 | 4/2014 |
| WO | WO-2014055648 A1 | 4/2014 |
| WO | WO-2014094122 A1 | 6/2014 |
| WO | WO-2014132072 A1 | 9/2014 |
| WO | WO-2014138306 A1 | 9/2014 |
| WO | WO-2014140358 A1 | 9/2014 |
| WO | WO-2014144689 A1 | 9/2014 |
| WO | WO-2014151910 A1 | 9/2014 |
| WO | WO-2015026684 A1 | 2/2015 |
| WO | WO-2015031667 A2 | 3/2015 |
| WO | WO-2015042246 A1 | 3/2015 |
| WO | WO-2015082499 A2 | 6/2015 |
| WO | WO-2015103072 A1 | 7/2015 |
| WO | WO-2015121812 A1 | 8/2015 |
| WO | WO-2015140717 A1 | 9/2015 |
| WO | WO-2015146437 A1 | 10/2015 |
| WO | WO-2015150097 A1 | 10/2015 |
| WO | WO-2015150447 A1 | 10/2015 |
| WO | WO-2015173764 A1 | 11/2015 |
| WO | WO-2015184099 A1 | 12/2015 |
| WO | WO-2015184207 A1 | 12/2015 |
| WO | WO-2015187835 A2 | 12/2015 |
| WO | WO-2016009029 A1 | 1/2016 |
| WO | WO-2016026772 A1 | 2/2016 |
| WO | WO-2016032334 A1 | 3/2016 |
| WO | WO-2016034044 A1 | 3/2016 |
| WO | WO-2016046778 A2 | 3/2016 |
| WO | WO-2016055551 A1 | 4/2016 |
| WO | WO-2016071283 A1 | 5/2016 |
| WO | WO-2016071293 A2 | 5/2016 |
| WO | WO-2016075099 A1 | 5/2016 |
| WO | WO-2016087531 A1 | 6/2016 |
| WO | WO-2016105450 A2 | 6/2016 |
| WO | WO-2016125017 A1 | 8/2016 |
| WO | WO-2016130819 A2 | 8/2016 |
| WO | WO-2016134333 A1 | 8/2016 |
| WO | WO-2016134335 A2 | 8/2016 |
| WO | WO-2016147144 A1 | 9/2016 |
| WO | WO-2016171999 A2 | 10/2016 |
| WO | WO-2016179003 A1 | 11/2016 |
| WO | WO-2016179518 A2 | 11/2016 |
| WO | WO-2016180982 A1 | 11/2016 |
| WO | WO-2016181348 A1 | 11/2016 |
| WO | WO-2016182064 A1 | 11/2016 |
| WO | WO-2016187101 A2 | 11/2016 |
| WO | WO-2016187594 A1 | 11/2016 |
| WO | WO-2016210447 A1 | 12/2016 |
| WO | WO-2017007700 A1 | 1/2017 |
| WO | WO-2017021349 A1 | 2/2017 |
| WO | WO-2017021356 A1 | 2/2017 |
| WO | WO-2017025038 A1 | 2/2017 |
| WO | WO-2017025698 A1 | 2/2017 |
| WO | WO-2017025868 A1 | 2/2017 |
| WO | WO-2017027392 A1 | 2/2017 |
| WO | WO-2017031104 A1 | 2/2017 |
| WO | WO-2017041749 A1 | 3/2017 |
| WO | WO-2017079528 A1 | 5/2017 |
| WO | WO-2017134134 A1 | 8/2017 |
| WO | WO-2017136549 A1 | 8/2017 |
| WO | WO-2017156178 A1 | 9/2017 |
| WO | WO-2017161206 A1 | 9/2017 |
| WO | WO-2017201488 A1 | 11/2017 |
| WO | WO-2017201493 A1 | 11/2017 |
| WO | WO-2017220988 A1 | 12/2017 |
| WO | WO-2018017863 A1 | 1/2018 |
| WO | WO-2018017864 A2 | 1/2018 |
| WO | WO-2018026953 A1 | 2/2018 |
| WO | WO-2018027203 A1 | 2/2018 |
| WO | WO-2018033798 A1 | 2/2018 |
| WO | WO-2018048975 A1 | 3/2018 |
| WO | WO-2018067993 A1 | 4/2018 |
| WO | WO-2018071777 A1 | 4/2018 |
| WO | WO-2018083204 A1 | 5/2018 |
| WO | WO-2018085469 A2 | 5/2018 |
| WO | WO-2018098354 A1 | 5/2018 |
| WO | WO-2018098356 A1 | 5/2018 |
| WO | WO-2018106529 A1 | 6/2018 |
| WO | WO-2018106588 A1 | 6/2018 |
| WO | WO-2018110555 A1 | 6/2018 |
| WO | WO-2018115859 A1 | 6/2018 |
| WO | WO-2018133877 A1 | 7/2018 |
| WO | WO-2018136725 A1 | 7/2018 |
| WO | WO-2018160671 A1 | 9/2018 |
| WO | WO-2018160754 A2 | 9/2018 |
| WO | WO-2018165619 A1 | 9/2018 |
| WO | WO-2018183366 A1 | 10/2018 |
| WO | WO-2018204717 A1 | 11/2018 |
| WO | WO-2018209298 A1 | 11/2018 |
| WO | WO-2018209304 A1 | 11/2018 |
| WO | WO-2018232020 A1 | 12/2018 |
| WO | WO-2019011852 A1 | 1/2019 |
| WO | WO-2019011855 A1 | 1/2019 |
| WO | WO-2019025983 A1 | 2/2019 |
| WO | WO-2019075359 A1 | 4/2019 |
| WO | WO-2019075378 A1 | 4/2019 |
| WO | WO-2019136305 A1 | 7/2019 |
| WO | WO-2019222278 A1 | 11/2019 |
| WO | WO-2019222282 A1 | 11/2019 |
| WO | WO-2019222283 A1 | 11/2019 |
| WO | WO-2019229701 A2 | 12/2019 |
| WO | WO-2019246004 A1 | 12/2019 |
| WO | WO-2020053263 A1 | 3/2020 |
| WO | WO-2020060593 A1 | 3/2020 |
| WO | WO-2020061482 A1 | 3/2020 |
| WO | WO-2020061526 A1 | 3/2020 |
| WO | WO-2020069028 A1 | 4/2020 |
| WO | WO-2020092792 A2 | 5/2020 |
| WO | WO-2020097403 A1 | 5/2020 |
| WO | WO-2020232303 A1 | 11/2020 |
| WO | WO-2020252349 A1 | 12/2020 |
| WO | WO-2020261093 A1 | 12/2020 |
| WO | WO-2020263830 A1 | 12/2020 |
| WO | WO-2021097060 A1 | 5/2021 |
| WO | WO-2021168303 A1 | 8/2021 |
| WO | WO-2021231434 A1 | 11/2021 |
| WO | WO-2022031884 A2 | 2/2022 |
| WO | WO-2022032006 A2 | 2/2022 |

(56) References Cited

FOREIGN PATENT DOCUMENTS

| | | |
|---|---|---|
| WO | WO-2022098909 A1 | 5/2022 |
| WO | WO-2022212732 A1 | 10/2022 |

OTHER PUBLICATIONS

Halaby et al. The immunoglobulin fold family: sequence analysis and 3D structure comparisons. Prot Eng 12(7):563-571 (1999).
Han et al. Masked Chimeric Antigen Receptor for Tumor-Specific Activation. Molecular Therapy 25(1):274-284 (2017).
Hassanzadeh-Ghassabeh et al. Nanobodies and their potential applications. Nanomedicine 8(6):1013-1026 (2013).
Huck et al. Sequence of a human immunoglobulin gamma 3 heavy chain constant region gene: comparison with the other human C gamma genes. Nucl. Acids Res. 14:1779-89 (1986).
Julian et al. Efficient affinity maturation of antibody variable domains requires co-selection of compensatory mutations to maintain thermodynamic stability. Sci Rep 7:45259 (2017).
Škrlec et al. Non-immunoglobulin scaffolds: a focus on their targets. Trends in Biotechnol 33:408-418 (2015).
Krzywinska et al. CD45 Isoform Profile Identifies Natural Killer (NK) Subsets with Differential Activity. PLoS One 11(4):e0150434 (2016).
Leibl et al. Ovarian granulosa cell tumors frequently express EGFR (Her-1), Her-3, and Her-4: An immunohistochemical study. Gynecol Oncol 101(1):18-23 (2006).
Mason et al. CD79a: a novel marker for B-cell neoplasms in routinely processed tissue samples. Blood 86(4):1453-1459 (1995).
PCT/US2020/060184 International Search Report and Written Opinion dated Mar. 4, 2021.
PCT/US2021/018853 International Search Report and Written Opinion dated Jul. 8, 2021.
PCT/US2021/031790 International Search Report and Written Opinion dated Sep. 16, 2021.
Sandler et al. Nondermatologic adverse events associated with anti-EGFR therapy. Oncology (Williston Park) 20(5 Suppl 2):35-40 (2006).
Sheng et al. Novel Transgenic Mouse Model for Studying Human Serum Albumin as a Biomarker of Carcinogenic Exposure. Chem. Res. Toxicol. 29(5):797-809 (2016).
Stehle et al. Albumin-based drug carriers: comparison between serum albumins of different species on pharmacokinetics and tumor uptake of the conjugate. Anticancer Drugs. 10(8):785-90 (1999).
Stirewalt et al. The role of FLT3 in haematopoietic malignancies. Nat Rev Cancer 3:650-665 (2003).
Tan et al. Influence of the hinge region on complement activation, C1q binding, and segmental flexibility in chimeric human immunoglobulins. PNAS USA 87:162-166 (1990).
Thomas. Cetuximab: adverse event profile and recommendations for toxicity management. Clin J Oncol Nurs. 9(3):332-8 (2005).
UniProtKB Accession No. A0A3M1V7M7_9EURY, lg-like_bact domain-containing protein, Feb. 13, 2019 [online] [Retrieved on Jun. 8, 2021], Retrieved from the internet <url:<a href="https://www.uniprotorg/uniprot/A0A3M1V7M7.bct">https://www.uniprotorg/uniprot/A0A3M1V7M7.bct</url:.<a>.
U.S. Appl. No. 16/159,554 Office Action dated Mar. 16, 2021.
U.S. Appl. No. 16/161,986 Office Action dated Dec. 2, 2021.
Baum et al. Antitumor activities of PSMAxCD3 diabodies by redirected T-cell lysis of prostate cancer cells. Immunotherapy 5(1):27-38 (2013).
Harmsen et al. Properties, production, and applications of camelid single-domain antibody fragments. Appl. Microbiol. Biotechnol. 77:13-22 (2007).
PCT/US2019/052270 International Search Report and Written Opinion dated Mar. 5, 2020.
U.S. Appl. No. 15/821,498 Office Action dated Apr. 21, 2020.
U.S. Appl. No. 15/821,530 Office Action dated Apr. 22, 2020.
U.S. Appl. No. 16/583,070 Office Action dated Mar. 3, 2020.
Zabetakis et al. Contributions of the complementarity determining regions to the thermal stability of a single-domain antibody. PLoS One 8(10):e77678 (2013).
Agata et al. Expression of the PD-1 antigen on the surface of stimulated mouse T and B lymphocytes. Int. Immunol 8:765-75 (1996).
Al-Lazikani et al. Standard conformations for the canonical structures of immunoglobulins. J. Mol Biology 273(4):927-948 (1997).
Almagro et al. Humanization of antibodies. Front Biosci 13:1619-1633 (2008).
Altschul et al. Basic local alignment search tool. J Mol Biol 215(3):403-410 (1990).
Altschul, et al. Gapped BLAST and PSI-BLAST: a new generation of protein database search programs. Nucleic Acids Res 25:3389-3402 (1977).
Argani et al. Mesothelin is overexpressed in the vast majority of ductal adenocarcinomas of the pancreas: identification of a new pancreatic cancer marker by serial analysis of gene expression (SAGE). Clin Cancer Res 7(12):3862-3868 (2001).
Austin et al. Cancer Research (Jul. 2018) vol. 78, No. 13, Supp. Supplement 1. Abstract No. 1781. Meeting Info: 2018 Annual Meeting of the American Association for Cancer Research, AACR 2018. Chicago, IL, United States. Apr. 14, 2018-Apr. 18, 2018).
Baca et al. Antibody humanization using monovalent phage display. J Biol Chem 272(16):10678-10684 (1997).
Baeuerle et al. Bispecific T-cell engaging antibodies for cancer therapy. Cancer Res 69:4941-4944 (2009).
Barrett et al. Treatment of advanced leukemia in mice with mRNA engineered T cells. Hum Gene Ther 22:1575-1586 (2011).
Batzer et al. Enhanced evolutionary PCR using oligonucleotides with inosine at the 3'-terminus. Nucleic Acids Res. 19(18):5081 (1991).
Bedouelle et al. Diversity and junction residues as hotspots of binding energy in an antibody neutralizing the dengue virus. FEBS J 273(1):34-46 (2006).
Bird et al. Single-chain antigen-binding proteins. Science 242(4877):423-426 (1988).
Blank et al. Interaction of PD-L1 on tumor cells with PD-1 on tumor-specific T cells as a mechanism of immune evasion: implications for tumor immunotherapy. Cancer Immunol Immunother 54:307-314 (2005).
Bortoletto et al. Optimizing anti-CD3 affinity for effective T cell targeting against tumor cells. Eur J Immunol 32:3102-3107 (2002).
Bracci et al. Cyclophosphamide enhances the antitumor efficacy of adoptively transferred immune cells through the induction of cytokine expression, B-cell and T-cell homeostatic proliferation, and specific tumor infiltration. Clin Cancer Res 13(2 Pt 1):644-653 (2007).
Brown et al. Tolerance of single, but not multiple, amino acid replacements in antibody VH CDR 2: a means of minimizing B cell wastage from somatic hypermutation? J Immunol 156(9):3285-3291 (1996).
Caldas et al. Design and synthesis of germline-based hemi-humanized single-chain Fv against the CD18 surface antigen. Protein Eng 13(5):353-360 (2000).
Caldas et al. Humanization of the anti-CD18 antibody 6.7: an unexpected effect of a framework residue in binding to antigen. Mol Immunol. 39(15):941-952 (2003).
Carter et al. Humanization of an anti-p185HER2 antibody for human cancer therapy. PNAS USA 89(10):4285-4289 (1992).
Carter et al. PD-1: PD-L inhibitory pathway affects both CD4(+) and CD8(+) T cells and is overcome by IL-2. Eur J Immunol 32:634-643 (2002).
Casset et al. A peptide mimetic of an anti-CD4 monoclonal antibody by rational design. Biochemical and Biophysical Research Communication 307:198-205 (2003).
Chang et al. Loop-sequence features and stability determinants in antibody variable domains by high-throughput experiments. Structure 22(1):9-21 (2014).
Chang et al. Molecular cloning of mesothelin, a differentiation antigen present on mesothelium, mesotheliomas, and ovarian cancers. PNAS USA 93:136-140 (1996).

(56) References Cited

OTHER PUBLICATIONS

Chatalic et al. A Novel 111 In-labeled Anti-PSMA Nanobody for Targeted SPECT/CT Imaging of Prostate Cancer. J Nucl Med 56(7):1094-1099 and Supplemental Data (2015).
Chen et al. Fusion protein linkers: Property, design and functionality. Advanced Drug Delivery Reviews 65:1357-1369 (2013).
Chen et al. Selection and analysis of an optimized anti-VEGF antibody: Crystal structure of an affinity-matured Fab in complex with antigen. J Mol Bio 293:865-881 (1999).
Chien et al. Significant structural and functional change of an antigen-binding site by a distant amino acid substitution: proposal of a structural mechanism. PNAS USA 86(14):5532-5536 (1989).
Cho et al. Targeting B Cell Maturation Antigen (BCMA) in Multiple Myeloma: Potential Uses of BCMA-Based Immunotherapy. Front Immunol 9:1821 (2018).
Choi et al. Engineering of Immunoglobulin Fc heterodimers using yeast surface-displayed combinatorial Fc library screening. PLOS One 10(12):e0145349 (2015).
Chothia et al. Canonical structures for the hypervariable regions of immunoglobulins. J Mol Biol 196(4):901-917 (1987).
Chothia, et al. Conformations of immunoglobulin hypervariable regions. Nature 342(6252):877-83 (1989).
Corso et al. Real-time detection of mesothelin in pancreatic cancer cell line supernatant using an acoustic wave immunosensor. Cancer Detect Prev 30:180-187 (2006).
Cougot et al. 'Cap-tabolism'. Trends in Biochem Sci 29:436-444 (2001).
Couto et al. Anti-BA46 monoclonal antibody Mc3: humanization using a novel positional consensus and in vivo and in vitro characterization. Cancer Res 55(8):1717-1722 (1995).
Couto et al. Designing human consensus antibodies with minimal positional templates. Cancer Res 55(23 Supp):5973s-5977s (1995).
Creaney et al. Detection of malignant mesothelioma in asbestos-exposed individuals: the potential role of soluble mesothelin-related protein. Hematol. Oncol. Clin. North Am. 19:1025-1040 (2005).
Cristaudo et al. Clinical significance of serum mesothelin in patients with mesothelioma and lung cancer. Clin. Cancer Res. 13:5076-5081 (2007).
Dao et al. Targeting the intracellular WT1 oncogene product with a therapeutic human antibody. Sci Transi Med 5(176):176ra33 (2013).
De Genst et al. Antibody repertoire development in camelids. Dev Comp Immunol 30(1-2):187-198 (2006).
De Pascalis et al. Grafting of "abbreviated" complementarity-determining regions containing specificity-determining residues essential for ligand contact to engineer a less immunogenic humanized monoclonal antibody. J Immunol. 169(6):3076-3084 (2002).
Dennis et al. Imaging Tumors with an Albumin-Binding Fab, a Novel Tumor-Targeting Agent. Cancer Res 67(1):254-61 (2007).
Document D28—Investigation of human CD3ε variants binding to monoclonal antibodies. Submitted by Pfizer to the European Patent Register on Apr. 30, 2014 in connection with their opposition to the EP2155783 patent. (3 pages) (2014).
Document D78—CD3ε N-terminal peptide bound to the CDRs of SP24. Submitted by Janssen Biotech to the European Patent Register on Mar. 18, 2016 in connection with their opposition to the EP2155783 patent (1 page) (2016).
Document D79—Interactions between CD3ε and SP34 CDR residues. CD3ε residues are in ellipses, SP34 CDR residues are in boxes. Submitted by Janssen Biotech to the European Patent Register on Mar. 18, 2016 in connection with their opposition to the EP2155783 patent (1 page) (2016).
Document D83—Alignment of variable domains from the prior art and the patent. Submitted by Janssen Biotech to the European Patent Register on Mar. 18, 2016 in connection with their opposition to the EP2155783 patent (1 page) (2016).
Dong et al. B7-H1 pathway and its role in the evasion of tumor immunity. J Mol Med 81:281-287 (2003).
Elango et al. Optimized transfection of mRNA transcribed from a d(A/T)100 tail-containing vector. Biochim Biophys Res Commun 330:958-966 (2005).

Foote et al. Antibody Framework Residues Affecting the Conformation of the Hypervariable Loops. J. Mol. Biol. 224(2):487-99 (1992).
Frankel et al. Targeting T cells to tumor cells using bispecific antibodies. Curr Opin Chem Biol 17(3):385-392 (2013).
Freeman et al. Engagement of the PD-1 immunoinhibitory receptor by a novel B7 family member leads to negative regulation of lymphocyte activation. J Exp Med 192:1027-1034 (2000).
Garland et al. The use of Teflon cell culture bags to expand functionally active CD8+ cytotoxic T lymphocytes. J Immunol Meth 227(1-2):53-63 (1999).
Giusti et al. Somatic diversification of S107 from an antiphosphocholine to an anti-DNA autoantibody is due to a single base change in its heavy chain variable region. PNAS USA 84(9):2926-30 (1987).
Goldman et al. Enhancing Stability of Camelid and Shark Single Domain Antibodies: An Overview. Front. Immunol. 8:865 (2017).
Goodman et al. The Pharmaceutical Basis of Therapeutics. 6th ed. pp. 21-25 (1980).
Goswami et al. Developments and Challenges for mAb-Based Therapeutics. Antibodies 2:452-500 (2013).
Gross et al. Endowing T cells with antibody specificity using chimeric T cell receptors. FASEB J. 6(15):3370-3378 (1992).
Grupp et al. Chimeric antigen receptor-modified T cells for acute lymphoid leukemia. NEJM 368:1509-1518 (2013).
Gubbels et al. Mesothelin-MUC16 binding is a high affinity, N-glycan dependent interaction that facilitates peritoneal metastasis of ovarian tumors. Mol Cancer 5:50 (2006).
Gussow et al. Chapter 5: Humanization of Monoclonal Antibodies. Methods in Enzymology 203:99-121 (1991).
Haanen et al. Selective expansion of cross-reactive CD8(+) memory T cells by viral variants. J Exp Med 190(9):1319-1328 (1999).
Harding et al. The immunogenicity of humanized and fully human antibodies: residual immunogenicity resides in the CDR regions. MAbs 2(3):256-265 (2010).
Hassan et al. Detection and quantitation of serum mesothelin, a tumor marker for patients with mesothelioma and ovarian cancer. Clin Cancer Res 12:447-453 (2006).
Hassan et al. Mesothelin: a new target for immunotherapy. Clin Cancer Res 10:3937-3942 (2004).
Hassan et al. Mesothelin targeted cancer immunotherapy. Eur J Cancer 44:46-53 (2008).
Hassan et al. Phase I study of SS1P, a recombinant anti-mesothelin immunotoxin given as a bolus I.V. infusion to patients with mesothelin-expressing mesothelioma, ovarian, and pancreatic cancers. Clin Cancer Res 13(17):5144-5149 (2007).
Hassan et al. Preclinical evaluation of MORAb-009, a chimeric antibody targeting tumor-associated mesothelin. Cancer Immun. 7:20 (2007).
Hellstrom et al. Mesothelin variant 1 is released from tumor cells as a diagnostic marker. Cancer Epidemiol Biomarkers Prev 15:1014-1020 (2006).
Hipp et al. A novel BCMA/CD3 bispecific T-cell engager for the treatment of multiple myeloma induces selective lysis in vitro and in vivo. Leukemia 31(8):1743-1751 (2017).
Ho et al. A novel high-affinity human monoclonal antibody to mesothelin. Int J Cancer 128:2020-2030 (2011).
Ho et al. Mesothelin expression in human lung cancer. Clin Cancer Res 13:1571-1575 (2007).
Ho et al. Mesothelin is shed from tumor cells. Cancer Epidemiol Biomarkers Prev 15:1751 (2006).
Hollinger et al. "Diabodies": Small bivalent and bispecific antibody fragments . PNAS USA 90:6444 6448 (1993).
Holm et al. Functional mapping and single chain construction of the anti-cytokeratin 8 monoclonal antibody TS1. Mol Immunol 44(6):1075-1084 (2007).
Holt et al. Anti-serum albumin domain antibodies for extending the half-lives of short-lived drugs. Protein Eng Des Sel 21(5):283-288 (2008).
Hopp et al. The effects of affinity and valency of an albumin-binding domain (ABD) on the half-life of a single-chain diabody-ABD fusion protein. Protein Eng. Des. Sel. 23(11):827-34 (2010).

(56) References Cited

OTHER PUBLICATIONS

Huston et al. Protein engineering of antibody binding sites: recovery of specific activity in an anti-digoxin single-chain Fv analogue produced in *Escherichia coli*. PNAS USA 85(16):5879-5883 (1988).
Hutchinson et al. Mutagenesis at a specific position in a DNA sequence. J Biol Chem 253:6551-6560 (1978).
Izumoto et al. Phase II clinical trial of Wilms tumor 1 peptide vaccination for patients with recurrent glioblastoma multiforme. J Neurosurg 108:963-971 (2008).
Janssen letter—Submission under Rule 116 EPC. Submitted by Janssen Biotech to the European Patent Register on Mar. 18, 2016 in connection with their opposition to the EP2155783 patent (6 pages) (2016).
Jones et al. Replacing the complementarity-determining regions in a human antibody with those from a mouse. Nature 321:522-525 (1986).
Kabat et al. Identical V region amino acid sequences and segments of sequences in antibodies of different specificities. Relative contributions of VH and VL genes, minigenes, and complementarity-determining regions to binding of antibody-combining sites. J Immunol 147:1709-1719 (1991).
Kabat et al. Sequences of proteins of immunological interest. NIH Publ. No. 91-3242 1:647-669 (1991).
Kalos et al. T cells with chimeric antigen receptors have potent antitumor effects and can establish memory in patients with advanced leukemia. Sci Transl Med 3(95):95ra73 (2011).
Kojima et al. Molecular cloning and expression of megakaryocyte potentiating factor cDNA. J Biol Chem 270:21984-21990 (1995).
Konishi et al. B7-H1 expression on non-small cell lung cancer cells and its relationship with tumor-infiltrating lymphocytes and their PD-1 expression. Clin Cancer Res 10:5094-5100 (2004).
Laabi et al. The BCMA gene, preferentially expressed during B lymphoid maturation, is bidirectionally transcribed. Nucleic Acids Res 22(7):1147-1154 (1994).
Latchman et al. PD-L2 is a second ligand for PD-1 and inhibits T cell activation. Nat Immunol 2:261-268 (2001).
Le Gall et al. Immunosuppressive properties of anti-CD3 single-chain Fv and diabody. J Immunol Methods 285(1):111-127 (2004).
Li et al. Development of novel tetravalent anti-CD20 antibodies with potent antitumor activity. Cancer Res 68:2400-2408 (2008).
Liu et al. A New Format of Single Chain Tri-specific Antibody with Diminished Molecular Size Efficiently Induces Ovarian Tumor Cell Killing. Biotechnology Letters 27(22):1821-1827 (2005).
Liu et al. MGD011, a CD19 × CD3 Dual Affinity Re-Targeting Bi-specific Molecule Incorporating Extended Circulating Half-life for the Treatment of B-cell Malignancies. Clin Cancer Res 23(6):1506-1518 (epub 2016) (2017).
Lowman et al. Monovalent phage display: A method for selecting variant proteins from random libraries. Methods 3:205-216 (1991).
Lu et al. In vitro and in vivo antitumor effect of a trivalent bispecific antibody targeting ErbB2 and CD16. Cancer Biol Ther. 7(11):1744-1750 (2008).
Lutterbuese et al. T cell-engaging BiTE antibodies specific for EGFR potently eliminate KRAS- and BRAF-mutated colorectal cancer cells. PNAS 107:12605-12610 (2007).
MacCallum et al. Antibody-antigen interactions: contact analysis and binding site topography. J Mol Biol. 262(5):732-745 (1996).
Mariuzza et al. The structural basis of antigen-antibody recognition. Annu Rev Biophys Biophys Chem 16:139-159 (1987).
Milone et al. Chimeric receptors containing CD137 signal transduction domains mediate enhanced survival of T cells and increased antileukemic efficacy in vivo. Mol Ther 17(8):1453-1464 (2009).
Mirsky et al. Antibody-Specific Model of Amino Acid Substitution for Immunological Inferences from Alignments of Antibody Sequences. Mol. Biol. Evol. 32(3):806-819 (2014).
Müller et al. Improved Pharmacokinetics of Recombinant Bispecific Antibody Molecules by Fusion to Human Serum Albumin. J. Biol. Chem. 282(17):12650-60 (2007).
Morea et al. Antibody modeling: implications for engineering and design. Methods 20(3):267-279 (2000).
Moschella et al. Unraveling cancer chemoimmunotherapy mechanisms by gene and protein expression profiling of responses to cyclophosphamide. Cancer Res 71(10):3528-3539 (2011).
Muller et al. Improving the pharmacokinetic properties of biologies by fusion to an anti-HSA shark VNAR domain. MAbs 4(6):673-685 (2012).
Mumtaz et al. Design of liposomes for circumventing the reticuloendothelial cells. Glycobiology 5:505-10 (1991).
Muul et al. Persistence and expression of the adenosine deaminase gene for 12 years and immune reaction to gene transfer components: long-term results of the first clinical gene therapy trial. Blood 101(7):2563-2569 (2003).
Muyldermans. Nanobodies: natural single-domain antibodies. Annu Rev Biochem 82:775-797 (2013).
Nacheva et al. Preventing nondesired RNA-primed RNA extension catalyzed by T7 RNA polymerase. Eur J Biochem 270:1458-1465 (2003).
Nazarian et al. Characterization of bispecific T-cell Engager (BiTE) antibodies with a high-capacity T-cell dependent cellular cytotoxicity (TDCC) assay. J Biomol Screen 20:519-527 (2015).
Needleman et al. A general method applicable to the search for similarities in the amino acid sequence of two proteins. J. Mol. Biol. 48:443-453 (1970).
Nelson et al. Antibody fragments Hope and Hype. mAbs 2(1):77-83 (2010).
Nicholson et al. Construction and characterisation of a functional CD19 specific single chain Fv fragment for immunotherapy of B lineage leukaemia and lymphoma. Mol Immun 34(16-17):1157-1165 (1997).
Nishikawa et al. Nonviral vectors in the new millennium: delivery barriers in gene transfer. Human Gene Therapy. 12:861-870 (2001).
Nunez-Prado et al. The coming of age of engineered multivalent antibodies. Drug Discovery Today 20(5):588-594 (2015).
Ohiro et al. A homogeneous and noncompetitive immunoassay based on the enhanced fluorescence resonance energy transfer by leucine zipper interaction. Anal Chem 74(22):5786-5792 (2002).
Ohtsuka et al. An alternative approach to deoxyoligonucleotides as hybridization probes by insertion of Deoxyinosine at Ambiguous Codon Positions. J Biol Chem 260(5):2605-2608 (Mar. 10, 1985).
O'Keefe et al. Chapter 18: Prostate specific membrane antigen. In: Chung L.W.K., Isaacs W.B., Simons J.W. (eds) Prostate Cancer. Contemporary Cancer Research. Humana Press, Totowa, NJ (pp. 307-326) (2001).
Ordonez. Application of mesothelin immunostaining in tumor diagnosis. Am J Surg Pathol 27:1418-1428 (2003).
Padlan. A possible procedure for reducing the immunogenicity of antibody variable domains while preserving their ligand-binding properties. Mol Immunol 28(4-5):489-498 (1991).
Padlan. Anatomy of the Antibody Molecule. Mol Immunol 31(3):169-217 (1994).
Padlan et al. Structure of an antibody-antigen complex: Crystal structure of the HyHEL-10 Fab-lysozyme complex. PNAS USA 86:5938-5942 (1989).
Pawluczkowycz et al. Binding of submaximal C1q promotes complement-dependent cytotoxicity (CDC) of B cells opsonized with anti-CD20 mAbs ofatumumab (OFA) or rituximab (RTX): considerably higher levels of CDC are induced by OFA than by RTX. J Immunol 183:749-758 (2009).
PCT/US2016/033644 International Search Report and Written Opinion dated Sep. 6, 2016.
PCT/US2017/033665 International Search Report and Written Opinion dated Oct. 18, 2017.
PCT/US2017/033673 International Search Report and Written Opinion dated Oct. 18, 2017.
PCT/US2017056530 International Search Report and Written Opinion dated Jan. 23, 2018.
PCT/US2017/063121 International Search Report and Written Opinion dated Mar. 26, 2018.
PCT/US2017/063121 Invitation to Pay Additional Fees dated Feb. 1, 2018.
PCT/US2017/063126 International Search Report and Written Opinion dated Apr. 5, 2018.

(56) References Cited

OTHER PUBLICATIONS

PCT/US2017/063126 Invitation to Pay Additional Fees dated Feb. 1, 2018.
PCT/US2018/014396 International Search Report and Written Opinion dated Jun. 14, 2018.
PCT/US2018/020185 International Search Report and Written Opinion dated Jun. 15, 2018.
PCT/US2018/020307 International Search Report and Written Opinion dated Aug. 24, 2018.
PCT/US2018/030983 International Search Report and Written Opinion dated Sep. 25, 2018.
PCT/US2018/030983 Invitation to Pay Additional Fees dated Jul. 31, 2018.
PCT/US2018/032418 International Search Report and Written Opinion dated Sep. 24, 2018.
PCT/US2018/032427 International Search Report and Written Opinion dated Sep. 13, 2018.
PCT/US2018/055659 International Search Report and Written Opinion dated Feb. 21, 2019.
PCT/US2018/055659 Invitation to Pay Additional Fees dated Dec. 19, 2018.
PCT/US2018/055682 International Search Report and Written Opinion dated Mar. 1, 2019.
PCT/US2018/055682 Invitation to Pay Additional Fees dated Jan. 8, 2019.
PCT/US2018/32418 Invitation to Pay Additional Fees dated Jul. 23, 2018.
PCT/US2018/32427 Invitation to Pay Additional Fees dated Jul. 24, 2018.
PCT/US2019/032224 International Search Report and Written Opinion dated Aug. 28, 2019.
PCT/US2019/032302 International Search Report and Written Opinion dated Aug. 22, 2019.
PCT/US2019/032306 International Search Report and Written Opinion dated Aug. 22, 2019.
PCT/US2019/032307 International Search Report and Written Opinion dated Aug. 22, 2019.
PCT/US2019/052206 International Search Report and Written Opinion dated Feb. 14, 2020.
PCT/US2019/052206 Invitation to Pay Additional Fees dated Dec. 23, 2019.
PCT/US2019/052270 Invitation to Pay Additional Fees dated Jan. 9, 2020.
PCT/US2019/053017 International Search Report and Written Opinion dated Jan. 31, 2020.
PCT/US2019/053017 Invitation to Pay Additional Fees dated Nov. 27, 2019.
Pearson, et al. Improved Tools for Biological Sequence Comparison. Proc. Nat'l Acad. Sci. USA. 85 (1988): 2444-48.
Pedersen et al. Comparison of surface accessible residues in human and murine immunoglobulin Fv domains. Implication for humanization of murine antibodies. J Mol Biol 235(3):959-973 (1994).
Pfizer letter—Opposition to European Patent EP2155783 (Application 08735001.3). Submitted by Pfizer to the European Patent Register on Apr. 30, 2014 in connection with their opposition to the EP2155783 patent. (pp. 1-23 and Appendix 1 on pp. 24-26) (2014).
Porter et al. Chimeric antigen receptor T cells persist and induce sustained remissions in relapsed refractory chronic lymphocytic leukemia. Sci Trans Med 7(303):303ra319 (2015).
Porter et al. Chimeric antigen receptor-modified T cells in chronic lymphoid leukemia. NEJM 365:725-733 (2011).
Presta. Antibody Engineering. Curr Op Struct Biol 2:593-596 (1992).
Presta et al. Humanization of an antibody directed against IgE. J Immunol 151:2623-2632 (1993).
Ramadoss et al. An Anti-B Cell Maturation Antigen Bispecific Antibody for Multiple Myeloma. J. Ann. Chem. Soc. 137(16):5288-91 (2015).
Riechmann et al. Reshaping human antibodies for therapy. Nature, 332.6162:323-7 (1988).
Riechmann et al. Single domain antibodies: comparison of camel VH and camelised human VH domains. J Immunol Methods 231(1-2):25-38 (1999).
Roguska et al. A comparison of two murine monoclonal antibodies humanized by CDR-grafting and variable domain resurfacing. Protein Eng 9(10):895-904 (1996).
Roguska et al. Humanization of murine monoclonal antibodies through variable domain resurfacing. PNAS 91:969-973 (1994).
Rosenberg et al. Use of tumor-infiltrating lymphocytes and interleukin-2 in the immunotherapy of patients with metastatic melanoma. A preliminary report. NEJM 319:1676 (1988).
Rosok et al. A Combinatorial Library Strategy for the Rapid Humanization of Anticarcinoma BR96 Fab. J Biol Chem 271:22611-22618 (1996).
Rossolini et al. Use of deoxyinosine-containing primers vs degenerate primers for polymerase chain reaction based on ambiguous sequence information. Mol Cell Probes 8(2):91-98 (1994).
Rozan et al. Single-domain antibody-based and linker-free bispecific antibodies targeting FcγRIII induce potent antitumor activity without recruiting regulatory T cells. Mol Cancer Ther 12(8):1481-1491 (2013).
Rudikoff et al. Single amino acid substitution altering antigen-binding Specificity. PNAS USA 79:1979-1983 (1982).
Rump et al. Binding of ovarian cancer antigen CA125/MUC16 to mesothelin mediates cell adhesion. J Biol Chem 279:9190-9198 (2004).
Running Deer et al. High-level expression of proteins in mammalian cells using transcription regulatory sequences from the Chinese hamster EF-1 alpha gene. Biotechnol Prog. 20:880-889 (2004).
Sadelain et al. Targeting tumours with genetically enhanced T lymphocytes. Nat Rev Cancer 3(1):35-45 (2003).
Sadelain et al. The basic principles of chimeric antigen receptor design. Cancer Discov. 3(4):388-98 (2013).
Saerens et al. Identification of a universal VHH framework to graft non-canonical antigen-binding loops of camel single-domain antibodies. J. Mol. Biol. 352(3):597-607 (2005).
Sandhu. A rapid procedure for the humanization of monoclonal antibodies. Gene 150(2):409-410 (1994).
Sastry et al. Targeting hepatitis B virus-infected cells with a T-cell receptor-like antibody. J Virol 85(5):1935-1942 (2011).
Schenborn et al. A novel transcription property of SP6 and T7 RNA polymerases: dependence on template structure. Nuc Acids Res 13:6223-6236 (1985).
Scheraga. Predicting three-dimensional structures of oligopeptides. Rev Computational Chem 3:73-142 (1992).
Schmidt et al. Cloning and Characterization of Canine Prostate-Specific Membrane Antigen. The Prostate 73:642-650 (2013).
Schmittgen et al. Expression of prostate specific membrane antigen and three alternatively spliced variants of PSMA in prostate cancer patients. Int J Cancer 107:323-329 (2003).
Sergeeva et al. An anti-PR1/HLA-A2 T-cell receptor-like antibody mediates complementdependent cytotoxicity against acute myeloid leukemia progenitor cells. Blood 117(16):4262-4272 (2011).
Sims et al. A humanized CD18 antibody can block function without cell destruction. J Immunol. 151:2296-2308 (1993).
Smirnova et al. Identification of new splice variants of the genes BAFF and BCMA. Mol. Immunol. 45 (4):1179-83 (2008).
Smith et al. Comparison of Biosequences. Advances in Applied Mathematics. 2:482-489 (1981).
Song et al. CD27 costimulation augments the survival and antitumor activity of redirected human T cells in vivo. Blood 119(3):696-706 (2012).
Spiess et al. Alternative molecular formats and therapeutic applications for bispecific antibodies. Mol. Immunol. 67(2 Pt A):95-106 (2015).
Stepinski et al. Synthesis and properties of mRNAs containing the novel 'anti-reverse' cap analogs 7-methyl(3'0-methyl)GpppG and 7-methyl(e'-deoxy)GpppG. RNA 7:1486-1495 (2001).
Sternjak et al. Cancer Research, (Jul. 2017) vol. 77, No. 13, Supp. Supplement 1. Abstract No. 3630. Meeting Info: American Association for Cancer Research Annual Meeting 2017. Washington, DC, United States. Apr. 1, 2017-Apr. 5, 2017.

(56) References Cited

OTHER PUBLICATIONS

Stork et al. A novel tri-functional antibody fusion protein with improved pharmacokinetic properties generated by fusing a bispecific single-chain diabody with an albumin-binding domain from streptococcal protein G. Protein Eng. Des. Sel. 20(11):569-76 (2007).
Strop. Veracity of microbial transglutaminase. Bioconjugate Chem. 25(5):855-862 (2014).
Studnicka et al. Human-engineered monoclonal antibodies retain full specific binding activity by preserving non-CDR complementarity-modulating residues. Pro Eng 7(6):805-814 (1994).
Su et al. PSMA specific single chain antibody-mediated targeted knockdown of Notch1 inhibits human prostate cancer cell proliferation and tumor growth. Cancer Lett. 338 (2): 282-291 (2013).
Tan et al. "Superhumanized" antibodies: reduction of immunogenic potential by complementarity-determining region grafting with human germline sequences: application to an anti-CD28. J Immunol 169:1119-1125 (2002).
Tang et al. A human single-domain antibody elicits potent antitumor activity by targeting an epitope in mesothelin close to the cancer cell surface. Mol. Cancer Thera 12(4):416-426 (2013).
Tassev et al. Retargeting NK92 cells using an HLA-A2-restricted, EBNA3C-specific chimeric antigen receptor. Cancer Gene Ther 19(2):84-100 (2012).
Ten Berg et al. Selective expansion of a peripheral blood CD8+ memory T cell subset expressing both granzyme B and L-selectin during primary viral infection in renal allograft recipients. Transplant Proc 30(8):3975-3977 (1998).
Thomas et al. Mesothelin-specific CD8(+) T cell responses provide evidence of in vivo cross-priming by antigen-presenting cells in vaccinated pancreatic cancer patients. J Exp Med 200:297-306 (2004).
Tijink et al. Improved tumor targeting of anti-epidermal growth factor receptor nanobodies through albumin binding: taking advantage of modular Nanobody technology. Mol. Cancer Ther. 7(8):2288-97 (2008).
Tiller et al. Facile Affinity Maturation of Antibody Variable Domains Using Natural Diversity Mutagenesis. Front. Immunol. 8:986 (2017).
Tutt et al. Trispecific F(ab')3 derivatives that use cooperative signaling via the TCR/CD3 complex and CD2 to activate and redirect resting cytotoxic T cells. J Immunol. 147(1):60-69 (Jul. 1, 1991).
Ui-Tei et al. Sensitive assay of RNA interference in Drosophila and Chinese hamster cultured cells using firefly luciferase gene as target. FEBS Letters 479: 79-82 (2000).
U.S. Appl. No. 15/160,984 Office Action dated Feb. 24, 2017.
U.S. Appl. No. 15/160,984 Office Action dated Sep. 22, 2016.
U.S. Appl. No. 15/600,264 Office Action dated Apr. 25, 2019.
U.S. Appl. No. 15/600,264 Office Action dated Apr. 26, 2018.
U.S. Appl. No. 15/600,264 Office Action dated Nov. 27, 2018.
U.S. Appl. No. 15/600,264 Office Action dated Oct. 3, 2017.
U.S. Appl. No. 15/600,582 Office Action dated Nov. 16, 2017.
U.S. Appl. No. 15/630,259 Office Action dated Dec. 30, 2019.
U.S. Appl. No. 15/704,620 Office Action dated Oct. 26, 2017.
U.S. Appl. No. 15/821,498 Office Action dated May 3, 2019.
U.S. Appl. No. 15/821,498 Office Action dated Oct. 26, 2018.
U.S. Appl. No. 15/821,530 Office Action dated Apr. 3, 2019.
U.S. Appl. No. 15/821,530 Office Action dated Sep. 25, 2018.
U.S. Appl. No. 15/977,968 Office Action dated Feb. 21, 2019.
U.S. Appl. No. 15/977,988 Office Action dated Aug. 20, 2019.
U.S. Appl. No. 15/977,988 Office Action dated Mar. 26, 2019.
U.S. Appl. No. 15/977,988 Preinterview First Office Action dated Jan. 25, 2019.
U.S. Appl. No. 16/159,545 Office Action dated Aug. 6, 2019.
U.S. Appl. No. 16/159,545 Office Action dated Dec. 2, 2019.
U.S. Appl. No. 16/159,554 Office Action dated Jun. 7, 2019.
U.S. Appl. No. 16/159,554 Office Action dated Oct. 1, 2019.
Vajdos et al. Comprehensive functional maps of the antigen-binding site of an anti-ErbB2 antibody obtained with shotgun scanning mutagenesis. J Mol Biol 320:415-428 (2002).
Van Den Beuchken et al. Building novel binding ligands to B7.1 and B7.2 based on human antibody single variable light chain domains. J Mol biol 310:591-601 (2001).
Van Der Linden et al. Induction of immune responses and molecular cloning of the heavy chain antibody repertoire of Lama glama. J Immunol Methods 240:185-195 (2000).
Vaughan et al. Human antibodies by design. Nature Biotech 16:535-539 (1998).
Verhoeyen et al. Reshaping human antibodies: Grafting an antilysozyme activity. Science 239:1534-1536 (1988).
Verma et al. TCR mimic monoclonal antibody targets a specific peptide/HLA class I complex and significantly impedes tumor growth in vivo using breast cancer models. J Immunol 184(4):2156-2165 (2010).
Vincke et al. General strategy to humanize a camelid single-domain antibody and identification of a universal humanized nanobody scaffold. J. Biol. Chem. 284(5):3273-3284 (2009).
Wang et al. A New Recombinant Single Chain Trispecific Antibody Recruits T Lymphocytes to Kill CEA (Carcinoma Embryonic Antigen) Positive Tumor Cells In Vitro Efficiently. Journal Of Biochemistry 135(4):555-565 (2004).
Willemsen et al. A phage display selected fab fragment with MHC class I-restricted specificity for MAGE-A1 allows for retargeting of primary human T lymphocytes. Gene Ther 8(21):1601-1608 (2001).
Winkler et al. Changing the antigen binding specificity by single point mutations of an anti-p24 (HIV-1) antibody. J Immunol. 165(8):4505-4514 (2000).
Wu et al. Humanization of a murine monoclonal antibody by simultaneous optimization of framework and CDR residues. J.Mol. Biol. 294:151-162 (1999).
Yan et al. Engineering upper hinge improves stability and effector function of a human IgG1. J. Biol. Chem. 287:5891 (2012).
Yee et al. Adoptive T cell therapy using antigen-specific CD8+ T cell clones for the treatment of patients with metastatic melanoma: in vivo persistence, migration, and antitumor effect of transferred T cells. PNAS USA 99(25):16168-16173 (2002).
Yoshinaga et al. Ig L-chain shuffling for affinity maturation of phage library-derived human anti-human MCP-1 antibody blocking its chemotactic activity. J Biochem 143(5):593-601 (2008).
Yu et al. Rationalization and design of the complementarity determining region sequences in an antibody-antigen recognition interface. PLoS One 7(3):e33340 (2012).
Zare et al. Production of nanobodies against prostate-specific membrane antigen (PSMA) recognizing LnCaP cells. Int. J. Biol. Markers 29(2):e169-e179 (2014).
Zhu et al. COMBODY: one-domain antibody multimer with improved avidity. Immunology and Cell Biology 88(6):667-675 (2010).
Balzar et al. The biology of the 17-1A antigen (Ep-CAM). J. Mol. Med. 77:699-712 (1999).
Chaubal et al. Ep-CAM—a marker for the detection of disseminated tumor cells in patients suffering from SCCHN. Anticancer Res 19:2237-2242 (1999).
Davé et al. Fab-dsFv: A bispecific antibody format with extended serum half-life through albumin binding. MAbs 8(7):1319-1335 (2016).
Eyvazi et al. Antibody Based EpCAM Targeted Therapy of Cancer, Review and Update. Curr Cancer Drug Targets. 18(9):857-868 (2018).
Gastl et al. Ep-CAM overexpression in breast cancer as a predictor of survival. Lancet. 356:1981-1982 (2000).
Goettlinger et al. The epithelial cell surface antigen 17-1A, a target for antibody-mediated tumor therapy: its biochemical nature, tissue distribution and recognition by different monoclonal antibodies. Int J Cancer. 38:47-53 (1986).
Kim et al. Strategies and 1-17 Advancement in Antibody-Drug Conjugate Optimization for Targeted Cancer Therapeutics. Biomol Ther (Seoul) 23(6):493-509 (2015).
Koprowski et al. Colorectal carcinoma antigens detected by hybridoma antibodies. Somatic Cell Genet. 5:957-971 (1979).
Lehmann et al. Stability engineering of anti-EGFR scFv antibodies by rational design of a lambda-to-kappa swap of the VL framework using a structure-guided approach. MAbs 7(6):1058-1071 (2015).

(56) References Cited

OTHER PUBLICATIONS

Lin et al. Improved affinity of a chicken single-chain antibody to avian infectious bronchitis virus by site-directed mutagenesis of complementarity-determining region H3. African Journal of Biotechnology 10(79):18294-18302 (2011).
Litvinov et al. Epithelial cell adhesion molecule (Ep-CAM) modulates cell-cell interactions mediated by classic cadherins. J Cell Biol. 139:1337-1348 (1997).
Litvinov et al. Expression of Ep-CAM in cervical squamous epithelia correlates with an increased proliferation and the disappearance of markers for terminal differentiation. Am. J. Pathol. 148:865-75 (1996).
Lucchi et al. The Masking Game: Design of Activatable Antibodies and Mimetics for Selective Thera-peutics Cell Control. ACS Cent Sci 7(5):724-738 (2021).
McCall et al. Isolation and characterization of an anti-CD16 single-chain Fv fragment and construction of an anti-HER2/neu/anti-CD16 bispecific scFv that triggers CD16-dependent tumor cytolysis Mol Immunol. 36(7):433-46 (1999).
McCarthy et al. Altering the fine specificity of an anti-Legionella single chain antibody by a single amino acid insertion. J Immunol Methods 251(1-2):137-49 (2001).
Osta et al. EpCAM is overexpressed in breast cancer and is a potential target for breast cancer gene therapy. Cancer Res 64:5818-24 (2004).
PCT/US2021/058108 International Search Report and Written Opinion dated Apr. 1, 2022.
Piyathilake et al. The expression of Ep-CAM (17-1A) in squamous cell cancers of the lung. Hum Pathol. 31:482-487 (2000).
Quak et al. Production of a monoclonal antibody (K 931) to a squamous cell carcinoma associated antigen identified as the 17-1A antigen. Hybridoma 9:377-387 (1990).
Simon et al. Epithelial glycoprotein is a member of a family of epithelial cell surface antigens homologous to nidogen, a matrix adhesion protein. PNAS USA 87:2755-2759 (1990).
Trail et al. Antibody drug 1-17 conjugates for treatment of breast cancer: Novel targets and diverse approaches in ADC design. Pharmacol Ther 181:126-142 (2018).
Trebak et al. Oligomeric state of the colon carcinoma-associated glycoprotein GA733-2 (Ep-CAM/EGP40) and its role in GA733-mediated homotypic cell-cell adhesion. J Biol Chem. 276:2299-2309 (2001).
U.S. Appl. No. 16/339,263 Office Action dated Jan. 11, 2022.
U.S. Appl. No. 16/489,523 Office Action dated Feb. 14, 2022.
U.S. Appl. No. 16/773,843 Office Action dated Feb. 8, 2022.
Zhang et al. New High Affinity Monoclonal Antibodies Recognize Non-Overlapping Epitopes on Mesothelin for Monitoring and Treating Mesothelioma. Sci Rep 5:9928 (2015).
Allard et al., The ectonucleotidases CD39 and CD73: Novel checkpoint inhibitor targets. Immunol Rev., 276(1):121-144 (2018).
Altenhofer et al., The NOX toolbox: validating the role of NADPH oxidases in physiology and disease. Cell Mol Life Sciences 69(14):2327-2343 (2012).
Austin et al. TriTACs, a Novel Class of T-Cell-Engaging Protein Constructs Designed for the Treatment of Solid Tumors. Mol Cancer Ther 20(1):109-120 (2021).
Ayers et al. IFN-γ-related mRNA profile predicts clinical response to PD-1 blockade. The Journal of Clinical Investigation 127(8):2930-2940 (Aug. 2017).
Balzar et al. Epidermal growth factor-like repeats mediate lateral and reciprocal interactions of Ep-CAM molecules in homophilic adhesions. Mol Cell Biol. 21(7):2570-80 (2001).
Bluemel et al. Epitope distance to the target cell membrane and antigen size determine the potency of T cell-mediated lysis by BiTE antibodies specific for a large melanoma surface antigen. Cancer Immunol Immunother 59(8):1197-209 (2010).
Cheong et al., A patent review of IDO1 inhibitors for cancer. Expert Opin Ther Pat. 28(4):317-330 (2018).
Croso et al., Real-time detection of mesothelin in pancreatic cancer cell line supernatant using an acoustic wave immunosensor. Cancer Detect. Prev. 30:180-187 (2006).
Dickopf et al. Format and geometries matter: Structure-based design defines the functionality of bispecific antibodies. Comput Struct Biotechnol J 18:1221-1227 (2020).
Fang et al. Characterization of an anti-human ovarian carcinomaxantihuman CD3 bispecific single-chain antibody with an albumin-original interlinker. Gynecol Oncol 92(1):135-146 (2004).
Gautam et al., Dual Inhibition of NOX2 and Receptor Tyrosine Kinase by BJ-1301 Enhances Anticancer Therapy Efficacy via Suppression of Autocrine-Stimulatory Factors in Lung Cancer. Mol Cancer Ther 16(10):2144-2156 (2017).
Gianni et al., A novel and specific NADPH oxidase-1 (Nox1) small-molecule inhibitor blocks the formation of functional invadopodia in human colon cancer cells. ACS Chem Biol 5(10):981-93 (2010).
Gorshkova et al. Single domain antibodies and bioengineering drugs on their basis: new opportunities for diagnostics and therapy. Medical Immunology (Russia) 18(6):505-520 (2016) (English Abstract).
Harris et al. A bispecific antibody agonist of the IL-2 heterodimeric receptor preferentially promotes in vivo expansion of CD8 and NK cells. Sci Rep. 11(1):10592 (2021).
Jang et al. Human 4-1 Bb (CD137) signals are mediated by TRAF2 and activate nuclear factorkappa B. Biochem. Biophys. Res. Commun. 242 (3):613-20 (1998).
Kakkad et al. Collagen 1 fiber content may predict for recurrence in non-small cell lung cancer. Cancer Research 78(13 Supplement):3691-3691 (2018).
Kauder et al., ALX148 blocks CD47 and enhances innate and adaptive antitumor immunity with a favorable safety profile. PLoS One 13(8):e0201832 (2019).
Kim et al., 2077—An oral dual inhibitor of IDO and TDO enhances anti-cancer immunity and synergizes with immune checkpoint blockade. Annals Oncol 29 (suppl_8):viii400-viii441 (2018) (Poster Abstract).
Lin et al. ProTriTAC: A Protease-Activatable T Cell Engager Platform that Links Half-Life Extension to Functional Masking Society for Immunotherapy of Cancer (SITC) Annual Meeting. Nov. 2018, Available at https://www.harpoontx.com/file.cfm/43/docs/SITC_2018_ProTriTAC_Poster.pdf.
Lu et al., Characterization of potent and selective iodonium-class inhibitors of NADPH oxidases. Biochem Pharmacol 143:25-38 (2017).
Lv et al. Mesothelin as a biomarker for targeted therapy. Biomark Res 7:18 (2019).
Ma et al. Combination therapy with T cell engager and PD-L1 blockade enhances the antitumor potency of T cells as predicted by a QSP model. J Immunother Cancer. 8(2):e001141 (2020).
Magiera-Mularz et al. Bioactive macrocyclic inhibitors of the PD-1/PD-L1 immune checkpoint Angew. Chem. Int. Ed. 56(44):13732-13735 (2017).
Monney et al. Th1-specific cell surface protein Tim-3 regulates macrophage activation and severity of an autoimmune disease. Nature 415:536-41 (2002).
Nakae et al. Phenotypic differences between Th1 and Th17 cells and negative regulation of Th1 cell differentiation by IL-17. J Leukoc Biol 81:1258-68 (2007).
Nicolaou et al. Calicheamicin Θ'1 : a rationally designed molecule with extremely potent and selective DNA cleaving properties and apoptosis inducing activity. Angew. Chem. Intl. Ed. Engl., 33:183-186 (1994).
PCT/US2022/019302 International Search Report and Written Opinion dated Jun. 27, 2022.
PCT/US2022/022871 International Search Report and Written Opinion dated Aug. 3, 2022.
PCT/US2022/031916 International Search Report and Written Opinion dated Sep. 29, 2022.
Perrot et al., Blocking Antibodies Targeting the CD39/CD73 Immunosuppressive Pathway Unleash Immune Responses in Combination Cancer Therapies. Cell Reports 8:2411-2425.E9 (2019).
Poczatek et al. Ep-Cam levels in prostatic adenocarcinoma and prostatic intraepithelial neoplasia. J Urol. 162:1462-1464 (1999).

(56) References Cited

OTHER PUBLICATIONS

Popoli et al., Effects of SCH 58261, an Adenosine A2A receptor antagonist, on quinpirole-induced turning in 6-Hydroxydopamine-lesioned rats: lack of tolerance after chronic caffeine intake. Neuropsychopharm 22:522-529 (2000).

Roda-Navarro et al. Understanding the Spatial Topology of Artificial Immunological Synapses Assembled in T Cell-Redirecting Strategies: A Major Issue in Cancer Immunotherapy. Front Cell Dev Biol 7:370 (2020).

Schaer et al. Modulation of GITR for cancer immunotherapy. Curr Opin Immunol. 24(2): 217-224 (2012).

Sheridan. IDO inhibitors move center stage in immuno-oncology. Nat Biotechnol 33:321-322 (2015).

Stasi et al., Animal models of Parkinson's disease: Effects of two adenosine A2A receptor antagonists ST4206 and ST3932, metabolites of 2-n-Butyl-9-methyl-8-[1,2,3]triazol-2-yl-9H-purin-6-ylamine (ST1535). Europ J Pharmacol 761:353-361 (2015).

Tang et al., NOX4, a new genetic target for anti-cancer therapy in digestive system cancer. J Dig Dis 19(10):578-585 (2018).

U.S. Appl. No. 16/339,263 Office Action dated May 3, 2022.

U.S. Appl. No. 16/773,843 Office Action dated Aug. 11, 2022.

U.S. Appl. No. 16/802,007 Office Action dated Sep. 29, 2022.

Wang et al., A Small Molecule Antagonist of PD-1/PD-L1 Interactions Acts as an Immune Checkpoint Inhibitor for NSCLC and Melanoma Immunotherapy. Front. Immunol. 12:654463.

Wang et al., In vitro characterization of the anti-PD-1 antibody nivolumab, BMS-936558, and in vivo toxicology in non-human primates. Cancer Immunol. Res. 2(9):846-856 (2014).

Watt et al., Homophilic adhesion of human CEACAM1 involves N-terminal domain interactions: structural analysis of the binding site. Blood 98:1469-1479 (2001).

Weir et al., Colony stimulating factor-1 plays a role in osteoclast formation and function in bone resorption induced by parathyroid hormone and parathyroid hormone-related protein. J Bone Mineral Res 11:1474-1481 (1996).

Co-pending U.S. Appl. No. 16/773,843, filed Jan. 27, 2020.

Co-pending U.S. Appl. No. 16/802,007, filed Feb. 26, 2020.

Bendell et al. Abstract 5552: First-in-human phase 1 study of HPN424, a tri-specific half-life extended PSMA-targeting T-cell engager in patients with metastatic castration-resistant prostate cancer (mCRPC). J Clin Oncol 38(15):5552 (May 2020).

PCT/US/2020/032985 International Search Report and Written Opinion dated Oct. 15, 2020.

U.S. Appl. No. 15/630,259 Office Action dated Sep. 30, 2020.

U.S. Appl. No. 16/159,554 Office Action dated Oct. 5, 2020.

Co-pending U.S. Appl. No. 16/999,773, inventors WESCHE; Holger et al., filed Aug. 21, 2020.

Co-pending U.S. Appl. No. 17/030,118, inventors DUBRIDGE; Robert et al., filed Sep. 23, 2020.

Co-pending U.S. Appl. No. 17/072,370, inventors BAEUERLE; Patrick et al., filed Oct. 16, 2020.

FIG. 2

EVQLVESGGGLVQPGGSLKLSCAASGFTFNKYAMNWVRQ
APGKGLEWVARIRSKYNNYATYYADSVKDRFTISRDDSKN
TAYLQMNNLKTEDTAVYYCVRHGNFGNSYISYWAYWGQ
GTLVTVSSGGGGSGGGGSGGGGSQTVVTQEPSLTVSPGGT
VTLTCGSSTGAVTSGNYPNWVQQKPGQAPRGLIGGTKFLA
PGTPARFSGSLLGGKAALTLSGVQPEDEAEYYCVLWYSNR
WVFGGGTKLTVL

FIG. 3

| anti-CD3e scFv | KD (nM) hum CD3e | kon(1/Ms) | kdis(1/s) | KD (nM) cyno CD3e | kon(1/Ms) | kdis(1/s) | cyno/hum ratio |
|---|---|---|---|---|---|---|---|
| wt | 4.4 | 4.71E+05 | 2.07E-03 | 3.9 | 4.63E+05 | 1.83E-03 | 0.9 |
| 2B2 | 3.8 | 6.08E+05 | 2.32E-03 | 3.5 | 5.57E+05 | 1.93E-03 | 0.9 |
| 9F2 | 4.1 | 3.61E+05 | 1.33E-03 | 3.4 | 3.38E+05 | 1.05E-03 | 0.8 |
| 5A2 | 4.3 | 5.66E+05 | 2.36E-03 | 4.2 | 4.75E+05 | 1.93E-03 | 1.0 |
| 6A2 | 4.7 | 5.22E+05 | 2.48E-03 | 4.9 | 4.56E+05 | 2.22E-03 | 1.0 |
| 2D2 | 6.4 | 5.27E+05 | 3.38E-03 | 6.6 | 4.71E+05 | 3.09E-03 | 1.0 |
| 3F2 | 8.0 | 7.04E+05 | 5.02E-03 | 6.6 | 7.12E+05 | 4.38E-03 | 0.8 |
| 2E4 | 14.4 | 4.16E+05 | 5.99E-03 | 13.2 | 4.04E+05 | 5.32E-03 | 0.9 |
| 2H2 | 16.0 | 5.87E+05 | 9.06E-03 | 16.0 | 5.25E+05 | 8.37E-03 | 1.0 |
| 10B2 | 17.9 | 4.90E+05 | 8.74E-03 | 16.6 | 4.93E+05 | 8.15E-03 | 0.9 |
| 1A2 | 19.9 | 5.99E+05 | 1.19E-02 | 17 | 5.31E+05 | 9.03E-03 | 0.9 |
| 1C2 | 36.8 | 6.63E+05 | 2.44E-02 | 30 | 6.69E+05 | 1.97E-02 | 0.8 |
| 2A4 | 46.3 | 3.64E+05 | 1.66E-02 | 43.4 | 3.53E+05 | 1.53E-02 | 0.9 |
| 10E4 | 49.8 | 5.22E+05 | 2.60E-02 | 46.8 | 5.08E+05 | 2.38E-02 | 0.9 |
| 8A5 | 109 | 7.46E+05 | 8.10E-02 | 103 | 7.23E+05 | 7.44E-02 | 0.9 |
| 2G5 | 117 | 9.94E+05 | 1.15E-01 | 115 | 9.64E+05 | 1.11E-01 | 1.0 |
| 1G4 | 132.9 | 1.67E+05 | 2.20E-02 | 133.7 | 1.64E+05 | 2.19E-02 | 1.0 |

FIG. 4

| Anti-huCD3ε variants | $T_h$ (°C) |
|---|---|
| WT | 59.2 |
| 2B2 | 57.4 |
| 3F2 | 52.2 |
| 2E4 | 55 |
| 2H2 | 53 |
| 10B2 | 51.5 |
| 2A4 | 56.2 |
| 2G5 | 58 |
| 1G4 | 60.3 | a

SEQUENCE LISTING

<160> NUMBER OF SEQ ID NOS: 105

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Gly Gly Gly Ser Gly Gly Gly Ser Gly Gly Gly Gly Ser
1               5                   10                  15

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Phe or Asn
<220> FEATURE:
<221> NAME/KEY: MOD_RES
<222> LOCATION: (3)..(3)
<223> OTHER INFORMATION: Thr, Glu or Met
<220> FEATURE:
<221> NAME/KEY: MOD_RES
<222> LOCATION: (4)..(4)
<223> OTHER INFORMATION: Phe or Tyr

```
<220> FEATURE:
<221> NAME/KEY: MOD_RES
<222> LOCATION: (6)..(6)
<223> OTHER INFORMATION: Lys, Thr, Gly, Asn or Glu
<220> FEATURE:
<221> NAME/KEY: MOD_RES
<222> LOCATION: (8)..(8)
<223> OTHER INFORMATION: Ala or Pro
<220> FEATURE:
<221> NAME/KEY: MOD_RES
<222> LOCATION: (9)..(9)
<223> OTHER INFORMATION: Met, Leu, Val or Ile

<400> SEQUENCE: 2

Gly Xaa Xaa Xaa Asn Xaa Tyr Xaa Xaa Asn
1               5                   10

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Lys or Gly
<220> FEATURE:
<221> NAME/KEY: MOD_RES
<222> LOCATION: (6)..(6)
<223> OTHER INFORMATION: Tyr or Ser
<220> FEATURE:
<221> NAME/KEY: MOD_RES
<222> LOCATION: (8)..(8)
<223> OTHER INFORMATION: Asn or Lys
<220> FEATURE:
<221> NAME/KEY: MOD_RES
<222> LOCATION: (10)..(10)
<223> OTHER INFORMATION: Ala or Glu
<220> FEATURE:
<221> NAME/KEY: MOD_RES
<222> LOCATION: (12)..(12)
<223> OTHER INFORMATION: Tyr or Glu
<220> FEATURE:
<221> NAME/KEY: MOD_RES
<222> LOCATION: (14)..(14)
<223> OTHER INFORMATION: Ala or Lys
<220> FEATURE:
<221> NAME/KEY: MOD_RES
<222> LOCATION: (16)..(16)
<223> OTHER INFORMATION: Ser, Glu, Asp, Ala or Gln

<400> SEQUENCE: 3

Arg Ile Arg Ser Xaa Xaa Asn Xaa Tyr Xaa Thr Xaa Tyr Xaa Asp Xaa
1               5                   10                  15

Val Lys

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gly, Ala or Thr
<220> FEATURE:
<221> NAME/KEY: MOD_RES
<222> LOCATION: (5)..(5)
<223> OTHER INFORMATION: Gly or Asn
<220> FEATURE:
```

```
<221> NAME/KEY: MOD_RES
<222> LOCATION: (6)..(6)
<223> OTHER INFORMATION: Asn or Asp
<220> FEATURE:
<221> NAME/KEY: MOD_RES
<222> LOCATION: (8)..(8)
<223> OTHER INFORMATION: Tyr, His, Pro, Gln, Leu or Gly
<220> FEATURE:
<221> NAME/KEY: MOD_RES
<222> LOCATION: (14)..(14)
<223> OTHER INFORMATION: Tyr or Thr

<400> SEQUENCE: 4

His Xaa Asn Phe Xaa Xaa Ser Xaa Ile Ser Tyr Trp Ala Xaa
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly or Ala
<220> FEATURE:
<221> NAME/KEY: MOD_RES
<222> LOCATION: (2)..(2)
<223> OTHER INFORMATION: Ser or Glu
<220> FEATURE:
<221> NAME/KEY: MOD_RES
<222> LOCATION: (3)..(3)
<223> OTHER INFORMATION: Ser or Tyr
<220> FEATURE:
<221> NAME/KEY: MOD_RES
<222> LOCATION: (4)..(4)
<223> OTHER INFORMATION: Thr, Phe, Lys or Ser
<220> FEATURE:
<221> NAME/KEY: MOD_RES
<222> LOCATION: (6)..(6)
<223> OTHER INFORMATION: Ala or Tyr
<220> FEATURE:
<221> NAME/KEY: MOD_RES
<222> LOCATION: (8)..(8)
<223> OTHER INFORMATION: Thr or Val
<220> FEATURE:
<221> NAME/KEY: MOD_RES
<222> LOCATION: (9)..(9)
<223> OTHER INFORMATION: Ser, Asp, Lys, His or Val
<220> FEATURE:
<221> NAME/KEY: MOD_RES
<222> LOCATION: (11)..(11)
<223> OTHER INFORMATION: Asn or Tyr

<400> SEQUENCE: 5

Xaa Xaa Xaa Xaa Gly Xaa Val Xaa Xaa Gly Xaa Tyr Pro Asn
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Thr or Ile
<220> FEATURE:
<221> NAME/KEY: MOD_RES
<222> LOCATION: (3)..(3)
<223> OTHER INFORMATION: Lys, Glu, Tyr, Asn or Ser
```

```
<220> FEATURE:
<221> NAME/KEY: MOD_RES
<222> LOCATION: (4)..(4)
<223> OTHER INFORMATION: Phe, Leu, Glu, Ile, Met or Val
<220> FEATURE:
<221> NAME/KEY: MOD_RES
<222> LOCATION: (5)..(5)
<223> OTHER INFORMATION: Ile, Asn or Gly
<220> FEATURE:
<221> NAME/KEY: MOD_RES
<222> LOCATION: (6)..(6)
<223> OTHER INFORMATION: Ala or Val

<400> SEQUENCE: 6

Gly Xaa Xaa Xaa Xaa Xaa Pro
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Val, Thr or Ala
<220> FEATURE:
<221> NAME/KEY: MOD_RES
<222> LOCATION: (5)..(5)
<223> OTHER INFORMATION: Ser, Asp or Ala
<220> FEATURE:
<221> NAME/KEY: MOD_RES
<222> LOCATION: (7)..(7)
<223> OTHER INFORMATION: Arg or Ser
<220> FEATURE:
<221> NAME/KEY: MOD_RES
<222> LOCATION: (9)..(9)
<223> OTHER INFORMATION: Val, Ile or Ala

<400> SEQUENCE: 7

Xaa Leu Trp Tyr Xaa Asn Xaa Trp Xaa
1               5

<210> SEQ ID NO 8
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Ile Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Gln Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Ala Asn Phe Gly Asn Ser Tyr Ile Ser Tyr Trp
            100                 105                 110
```

```
Ala Tyr Trp Gly Gln Gly Thr Leu Val Thr Val Ser Ser Gly Gly Gly
            115                 120                 125
Gly Ser Gly Gly Gly Gly Ser Gly Gly Gly Ser Gln Thr Val Val
        130                 135                 140
Thr Gln Glu Pro Ser Leu Thr Val Ser Pro Gly Gly Thr Val Thr Leu
145                 150                 155                 160
Thr Cys Ala Ser Ser Thr Gly Ala Val Thr Ser Gly Asn Tyr Pro Asn
                165                 170                 175
Trp Val Gln Gln Lys Pro Gly Gln Ala Pro Arg Gly Leu Ile Gly Gly
                180                 185                 190
Thr Lys Phe Leu Val Pro Gly Thr Pro Ala Arg Phe Ser Gly Ser Leu
            195                 200                 205
Leu Gly Gly Lys Ala Ala Leu Thr Leu Ser Gly Val Gln Pro Glu Asp
        210                 215                 220
Glu Ala Glu Tyr Tyr Cys Thr Leu Trp Tyr Ser Asn Arg Trp Val Phe
225                 230                 235                 240
Gly Gly Gly Thr Lys Leu Thr Val Leu
                245

<210> SEQ ID NO 9
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Val Glu Ser Gly Gly Gly Leu Val Gln Pro Gly Gly
1               5                   10                  15
Ser Leu Lys Leu Ser Cys Ala Ala Ser Gly Phe Glu Phe Asn Lys Tyr
            20                  25                  30
Ala Met Asn Trp Val Arg Gln Ala Pro Gly Lys Gly Leu Glu Trp Val
        35                  40                  45
Ala Arg Ile Arg Ser Lys Tyr Asn Lys Tyr Ala Thr Tyr Tyr Ala Asp
    50                  55                  60
Ser Val Lys Asp Arg Phe Thr Ile Ser Arg Asp Asp Ser Lys Asn Thr
65                  70                  75                  80
Ala Tyr Leu Gln Met Asn Asn Leu Lys Thr Glu Asp Thr Ala Val Tyr
                85                  90                  95
Tyr Cys Val Arg His Gly Asn Phe Gly Asn Ser Tyr Ile Ser Tyr Trp
            100                 105                 110
Ala Tyr Trp Gly Gln Gly Thr Leu Val Thr Val Ser Ser Gly Gly Gly
            115                 120                 125
Gly Ser Gly Gly Gly Gly Ser Gly Gly Gly Ser Gln Thr Val Val
        130                 135                 140
Thr Gln Glu Pro Ser Leu Thr Val Ser Pro Gly Gly Thr Val Thr Leu
145                 150                 155                 160
Thr Cys Gly Ser Ser Phe Gly Ala Val Thr Ser Gly Asn Tyr Pro Asn
                165                 170                 175
Trp Val Gln Gln Lys Pro Gly Gln Ala Pro Arg Gly Leu Ile Gly Gly
                180                 185                 190
Thr Lys Phe Leu Ala Pro Gly Thr Pro Ala Arg Phe Ser Gly Ser Leu
            195                 200                 205
```

Leu Gly Gly Lys Ala Ala Leu Thr Leu Ser Gly Val Gln Pro Glu Asp
            210                 215                 220

Glu Ala Glu Tyr Tyr Cys Val Leu Trp Tyr Asp Asn Arg Trp Val Phe
225                 230                 235                 240

Gly Gly Gly Thr Lys Leu Thr Val Leu
            245

<210> SEQ ID NO 10
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser His Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Tyr Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Ser Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Ile Phe
225                 230                 235                 240

Gly Gly Gly Thr Lys Leu Thr Val Leu
            245

<210> SEQ ID NO 11
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Met Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Thr Trp Gly Gln Gly Thr Leu Val Thr Val Ser Ser Gly Gly Gly
        115                 120                 125

Gly Ser Gly Gly Gly Ser Gly Gly Gly Ser Gln Thr Val Val
130                 135                 140

Thr Gln Glu Pro Ser Leu Thr Val Ser Pro Gly Gly Thr Val Thr Leu
145                 150                 155                 160

Thr Cys Gly Ser Ser Phe Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Leu Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Ser Trp Val Phe
225                 230                 235                 240

Gly Gly Gly Thr Lys Leu Thr Val Leu
                245
```

<210> SEQ ID NO 12
<211> LENGTH: 249
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Lys Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95
```

Tyr Cys Val Arg His Gly Asn Phe Gly Asn Ser Pro Ile Ser Tyr Trp
                100                 105                 110

Ala Tyr Trp Gly Gln Gly Thr Leu Val Thr Val Ser Ser Gly Gly Gly
            115                 120                 125

Gly Ser Gly Gly Gly Gly Ser Gly Gly Gly Ser Gln Thr Val Val
130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Val Ser Gly Asn Tyr Pro Asn
                165                 170                 175

Trp Val Gln Gln Lys Pro Gly Gln Ala Pro Arg Gly Leu Ile Gly Gly
                180                 185                 190

Thr Glu Phe Leu Ala Pro Gly Thr Pro Ala Arg Phe Ser Gly Ser Leu
            195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245

<210> SEQ ID NO 13
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Tyr Asn Lys Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
    50                  55                  60

Glu Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Pro Ile Ser Tyr Trp
                100                 105                 110

Ala Tyr Trp Gly Gln Gly Thr Leu Val Thr Val Ser Ser Gly Gly Gly
            115                 120                 125

Gly Ser Gly Gly Gly Gly Ser Gly Gly Gly Ser Gln Thr Val Val
130                 135                 140

Thr Gln Glu Pro Ser Leu Thr Val Ser Pro Gly Gly Thr Val Thr Leu
145                 150                 155                 160

Thr Cys Gly Ser Ser Lys Gly Ala Val Thr Ser Gly Asn Tyr Pro Asn
                165                 170                 175

Trp Val Gln Gln Lys Pro Gly Gln Ala Pro Arg Gly Leu Ile Gly Gly
                180                 185                 190

Thr Lys Glu Leu Ala Pro Gly Thr Pro Ala Arg Phe Ser Gly Ser Leu
            195                 200                 205

Leu Gly Gly Lys Ala Ala Leu Thr Leu Ser Gly Val Gln Pro Glu Asp
    210                 215                 220

Glu Ala Glu Tyr Tyr Cys Thr Leu Trp Tyr Ser Asn Arg Trp Val Phe
225                 230                 235                 240

Gly Gly Gly Thr Lys Leu Thr Val Leu
                245

<210> SEQ ID NO 14
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Val Gln Leu Val Glu Ser Gly Gly Gly Leu Val Gln Pro Gly Gly
1               5                   10                  15

Ser Leu Lys Leu Ser Cys Ala Ala Ser Gly Asn Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Glu Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Thr Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Tyr Tyr Pro Asn
                165                 170                 175

Trp Val Gln Gln Lys Pro Gly Gln Ala Pro Arg Gly Leu Ile Gly Gly
            180                 185                 190

Thr Tyr Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245

<210> SEQ ID NO 15
<211> LENGTH: 249
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 15

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Asn Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ala Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Gln Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Asp Gly Asn Tyr Pro Asn
                165                 170                 175

Trp Val Gln Gln Lys Pro Gly Gln Ala Pro Arg Gly Leu Ile Gly Gly
            180                 185                 190

Ile Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245

<210> SEQ ID NO 16
<211> LENGTH: 249
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 16

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Val Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

```
Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Glu Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Ile Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245

<210> SEQ ID NO 17
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Pro Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Asn Glu Asp Thr Ala Val Tyr
                85                  90                  95

Tyr Cys Val Arg His Gly Asn Phe Asn Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Lys Gly Asn Tyr Pro Asn
                165                 170                 175

Trp Val Gln Gln Lys Pro Gly Gln Ala Pro Arg Gly Leu Ile Gly Gly
            180                 185                 190
```

```
Thr Lys Met Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
210                 215                 220

Glu Ala Glu Tyr Tyr Cys Ala Leu Trp Tyr Ser Asn Arg Trp Val Phe
225                 230                 235                 240

Gly Gly Gly Thr Lys Leu Thr Val Leu
                245

<210> SEQ ID NO 18
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Gly Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Glu Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Pro Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Val Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Glu Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245

<210> SEQ ID NO 19
<211> LENGTH: 249
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 19

Glu Val Gln Leu Val Glu Ser Gly Gly Gly Leu Val Gln Pro Gly Gly
1               5                   10                  15

Ser Leu Lys Leu Ser Cys Ala Ala Ser Gly Asn Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asp Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr His Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Val Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245

<210> SEQ ID NO 20
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Asn Tyr
            20                  25                  30

Ala Met Asn Trp Val Arg Gln Ala Pro Gly Lys Gly Leu Glu Trp Val
        35                  40                  45

Ala Arg Ile Arg Ser Gly Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

```
Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Tyr Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Asn Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ala Asn Arg Trp Val Phe
225                 230                 235                 240

Gly Gly Gly Thr Lys Leu Thr Val Leu
                245

<210> SEQ ID NO 21
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Glu Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Glu Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Leu Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Ser Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190
```

```
Thr Lys Phe Gly Ala Pro Gly Thr Pro Ala Arg Phe Ser Gly Ser Leu
            195                 200                 205

Leu Gly Gly Lys Ala Ala Leu Thr Leu Ser Gly Val Gln Pro Glu Asp
        210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245
```

<210> SEQ ID NO 22
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245
```

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic -continued

```
      peptide

<400> SEQUENCE: 23

Gly Phe Thr Phe Asn Lys Tyr Ala Met Asn
1               5                   10

<210> SEQ ID NO 24
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Ile Arg Ser Lys Tyr Asn Asn Tyr Ala Thr Tyr Tyr Ala Asp Ser
1               5                   10                  15

Val Lys

<210> SEQ ID NO 25
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

His Gly Asn Phe Gly Asn Ser Tyr Ile Ser Tyr Trp Ala Tyr
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Ser Ser Thr Gly Ala Val Thr Ser Gly Asn Tyr Pro Asn
1               5                   10

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Thr Lys Phe Leu Ala Pro
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Val Leu Trp Tyr Ser Asn Arg Trp Val
1               5
```

```
<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Asn Thr Phe Asn Lys Tyr Ala Met Asn
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Phe Glu Phe Asn Lys Tyr Ala Met Asn
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Phe Met Phe Asn Lys Tyr Ala Met Asn
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Phe Thr Tyr Asn Lys Tyr Ala Met Asn
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Phe Thr Phe Asn Asn Tyr Ala Met Asn
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 34

Gly Phe Thr Phe Asn Gly Tyr Ala Met Asn
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Phe Thr Phe Asn Thr Tyr Ala Met Asn
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Phe Thr Phe Asn Glu Tyr Ala Met Asn
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Phe Thr Phe Asn Lys Tyr Pro Met Asn
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Phe Thr Phe Asn Lys Tyr Ala Val Asn
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Phe Thr Phe Asn Lys Tyr Ala Ile Asn
1               5                   10

<210> SEQ ID NO 40
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 40

Gly Phe Thr Phe Asn Lys Tyr Ala Leu Asn
1               5                   10

<210> SEQ ID NO 41
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Ile Arg Ser Gly Tyr Asn Asn Tyr Ala Thr Tyr Tyr Ala Asp Ser
1               5                   10                  15

Val Lys

<210> SEQ ID NO 42
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Ile Arg Ser Lys Ser Asn Asn Tyr Ala Thr Tyr Tyr Ala Asp Ser
1               5                   10                  15

Val Lys

<210> SEQ ID NO 43
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Ile Arg Ser Lys Tyr Asn Lys Tyr Ala Thr Tyr Tyr Ala Asp Ser
1               5                   10                  15

Val Lys

<210> SEQ ID NO 44
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Ile Arg Ser Lys Tyr Asn Asn Tyr Glu Thr Tyr Tyr Ala Asp Ser
1               5                   10                  15

Val Lys

<210> SEQ ID NO 45
<211> LENGTH: 18
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 45

Arg Ile Arg Ser Lys Tyr Asn Asn Tyr Ala Thr Glu Tyr Ala Asp Ser
1               5                   10                  15

Val Lys

<210> SEQ ID NO 46
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Ile Arg Ser Lys Tyr Asn Asn Tyr Ala Thr Tyr Tyr Lys Asp Ser
1               5                   10                  15

Val Lys

<210> SEQ ID NO 47
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Arg Ile Arg Ser Lys Tyr Asn Asn Tyr Ala Thr Tyr Tyr Ala Asp Glu
1               5                   10                  15

Val Lys

<210> SEQ ID NO 48
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Arg Ile Arg Ser Lys Tyr Asn Asn Tyr Ala Thr Tyr Tyr Ala Asp Ala
1               5                   10                  15

Val Lys

<210> SEQ ID NO 49
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Arg Ile Arg Ser Lys Tyr Asn Asn Tyr Ala Thr Tyr Tyr Ala Asp Gln
1               5                   10                  15

Val Lys

<210> SEQ ID NO 50
<211> LENGTH: 18
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 50

Arg Ile Arg Ser Lys Tyr Asn Asn Tyr Ala Thr Tyr Tyr Ala Asp Asp
1               5                   10                  15

Val Lys

<210> SEQ ID NO 51
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

His Ala Asn Phe Gly Asn Ser Tyr Ile Ser Tyr Trp Ala Tyr
1               5                   10

<210> SEQ ID NO 52
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

His Thr Asn Phe Gly Asn Ser Tyr Ile Ser Tyr Trp Ala Tyr
1               5                   10

<210> SEQ ID NO 53
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

His Gly Asn Phe Asn Asn Ser Tyr Ile Ser Tyr Trp Ala Tyr
1               5                   10

<210> SEQ ID NO 54
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

His Gly Asn Phe Gly Asp Ser Tyr Ile Ser Tyr Trp Ala Tyr
1               5                   10

<210> SEQ ID NO 55
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

His Gly Asn Phe Gly Asn Ser His Ile Ser Tyr Trp Ala Tyr
1               5                   10

<210> SEQ ID NO 56
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

His Gly Asn Phe Gly Asn Ser Pro Ile Ser Tyr Trp Ala Tyr
1               5                   10

<210> SEQ ID NO 57
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

His Gly Asn Phe Gly Asn Ser Gln Ile Ser Tyr Trp Ala Tyr
1               5                   10

<210> SEQ ID NO 58
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

His Gly Asn Phe Gly Asn Ser Leu Ile Ser Tyr Trp Ala Tyr
1               5                   10

<210> SEQ ID NO 59
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

His Gly Asn Phe Gly Asn Ser Gly Ile Ser Tyr Trp Ala Tyr
1               5                   10

<210> SEQ ID NO 60
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

His Gly Asn Phe Gly Asn Ser Tyr Ile Ser Tyr Trp Ala Thr
1               5                   10

<210> SEQ ID NO 61
<211> LENGTH: 14

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ala Ser Ser Thr Gly Ala Val Thr Ser Gly Asn Tyr Pro Asn
1               5                   10

<210> SEQ ID NO 62
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Glu Ser Thr Gly Ala Val Thr Ser Gly Asn Tyr Pro Asn
1               5                   10

<210> SEQ ID NO 63
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Ser Tyr Thr Gly Ala Val Thr Ser Gly Asn Tyr Pro Asn
1               5                   10

<210> SEQ ID NO 64
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Ser Ser Phe Gly Ala Val Thr Ser Gly Asn Tyr Pro Asn
1               5                   10

<210> SEQ ID NO 65
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gly Ser Ser Lys Gly Ala Val Thr Ser Gly Asn Tyr Pro Asn
1               5                   10

<210> SEQ ID NO 66
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 66

Gly Ser Ser Ser Gly Ala Val Thr Ser Gly Asn Tyr Pro Asn
1               5                   10

<210> SEQ ID NO 67
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Ser Ser Thr Gly Tyr Val Thr Ser Gly Asn Tyr Pro Asn
1               5                   10

<210> SEQ ID NO 68
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Ser Ser Thr Gly Ala Val Val Ser Gly Asn Tyr Pro Asn
1               5                   10

<210> SEQ ID NO 69
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Ser Ser Thr Gly Ala Val Thr Asp Gly Asn Tyr Pro Asn
1               5                   10

<210> SEQ ID NO 70
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Ser Ser Thr Gly Ala Val Thr Lys Gly Asn Tyr Pro Asn
1               5                   10

<210> SEQ ID NO 71
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Ser Ser Thr Gly Ala Val Thr His Gly Asn Tyr Pro Asn
1               5                   10

<210> SEQ ID NO 72
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Ser Ser Thr Gly Ala Val Thr Val Gly Asn Tyr Pro Asn
1               5                   10

<210> SEQ ID NO 73
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Ser Ser Thr Gly Ala Val Thr Ser Gly Tyr Tyr Pro Asn
1               5                   10

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Ile Lys Phe Leu Ala Pro
1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Thr Glu Phe Leu Ala Pro
1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Thr Tyr Phe Leu Ala Pro
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 77

Gly Thr Ser Phe Leu Ala Pro
1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Thr Asn Phe Leu Ala Pro
1               5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Thr Lys Leu Leu Ala Pro
1               5

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Thr Lys Glu Leu Ala Pro
1               5

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Thr Lys Ile Leu Ala Pro
1               5

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gly Thr Lys Met Leu Ala Pro
1               5

<210> SEQ ID NO 83
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Thr Lys Val Leu Ala Pro
1               5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Thr Lys Phe Asn Ala Pro
1               5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Thr Lys Phe Gly Ala Pro
1               5

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gly Thr Lys Phe Leu Val Pro
1               5

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Thr Leu Trp Tyr Ser Asn Arg Trp Val
1               5

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 88

Ala Leu Trp Tyr Ser Asn Arg Trp Val
1               5

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Val Leu Trp Tyr Asp Asn Arg Trp Val
1               5

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Val Leu Trp Tyr Ala Asn Arg Trp Val
1               5

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Val Leu Trp Tyr Ser Asn Ser Trp Val
1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Val Leu Trp Tyr Ser Asn Arg Trp Ile
1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Val Leu Trp Tyr Ser Asn Arg Trp Ala
1               5

<210> SEQ ID NO 94
<211> LENGTH: 249
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Leu Asn Trp Val Arg Gln Ala Pro Gly Lys Gly Leu Glu Trp Val
        35                  40                  45

Ala Arg Ile Arg Ser Lys Tyr Asn Asn Tyr Ala Thr Glu Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Pro Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Asn Phe Leu Ala Pro Gly Thr Pro Glu Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Ala Phe
225                 230                 235                 240

Gly Gly Gly Thr Lys Leu Thr Val Leu
                245

<210> SEQ ID NO 95
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Glu Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60
```

```
Asp Val Lys Asp Arg Phe Thr Ile Ser Arg Asp Ser Lys Asn Thr
 65                  70                  75                  80

Ala Tyr Leu Gln Met Asn Asn Leu Lys Thr Glu Asp Thr Ala Val Tyr
             85                  90                  95

Tyr Cys Val Arg His Gly Asn Phe Gly Asn Ser Gly Ile Ser Tyr Trp
        100                 105                 110

Ala Tyr Trp Gly Gln Gly Thr Leu Val Thr Val Ser Gly Gly Gly
        115                 120                 125

Gly Ser Gly Gly Gly Ser Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Val Gly Asn Tyr Pro Asn
                165                 170                 175

Trp Val Gln Gln Lys Pro Gly Gln Ala Pro Arg Gly Leu Ile Gly Gly
                180                 185                 190

Thr Glu Phe Leu Ala Pro Gly Thr Pro Ala Arg Phe Ser Gly Ser Leu
            195                 200                 205

Leu Gly Gly Lys Ala Ala Leu Thr Leu Ser Gly Val Gln Pro Glu Asp
210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245

<210> SEQ ID NO 96
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 1-10 "Gly Ser"
      repeating units

<400> SEQUENCE: 96

Gly Ser Gly Ser Gly Ser Gly Ser Gly Ser Gly Ser Gly Ser
1               5                   10                  15

Gly Ser Gly Ser
            20

<210> SEQ ID NO 97
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(30)
<223> OTHER INFORMATION: This sequence may encompass 1-10 "Gly Gly Ser"
      repeating units

<400> SEQUENCE: 97

Gly Gly Ser Gly Gly Ser Gly Gly Ser Gly Gly Ser Gly
1               5                   10                  15

Gly Ser Gly Gly Ser Gly Gly Ser Gly Gly Ser
            20                  25                  30
```

<210> SEQ ID NO 98
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(40)
<223> OTHER INFORMATION: This sequence may encompass 1-10 "Gly Gly Gly
      Ser" repeating units

<400> SEQUENCE: 98

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40

<210> SEQ ID NO 99
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(40)
<223> OTHER INFORMATION: This sequence may encompass 1-10 "Gly Gly Ser
      Gly" repeating units

<400> SEQUENCE: 99

Gly Gly Ser Gly Gly Gly Ser Gly Gly Gly Ser Gly Gly Gly Ser Gly
1               5                   10                  15

Gly Gly Ser Gly Gly Gly Ser Gly Gly Gly Ser Gly Gly Gly Ser Gly
            20                  25                  30

Gly Gly Ser Gly Gly Gly Ser Gly
        35                  40

<210> SEQ ID NO 100
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(50)
<223> OTHER INFORMATION: This sequence may encompass 1-10 "Gly Gly Ser
      Gly Gly" repeating units

<400> SEQUENCE: 100

Gly Gly Ser Gly Gly Gly Gly Ser Gly Gly Gly Gly Ser Gly Gly Gly
1               5                   10                  15

Gly Ser Gly Gly Gly Gly Ser Gly Gly Gly Gly Ser Gly Gly Gly Gly
            20                  25                  30

Ser Gly Gly Gly Gly Ser Gly Gly Gly Gly Ser Gly Gly Gly Gly Ser
        35                  40                  45

Gly Gly
    50

```
<210> SEQ ID NO 101
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(50)
<223> OTHER INFORMATION: This sequence may encompass 1-10 "Gly Gly Gly
      Gly Ser" repeating units

<400> SEQUENCE: 101

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50

<210> SEQ ID NO 102
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(50)
<223> OTHER INFORMATION: This sequence may encompass 1-10 "Gly Gly Gly
      Gly Gly" repeating units

<400> SEQUENCE: 102

Gly Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly Gly
        35                  40                  45

Gly Gly
    50

<210> SEQ ID NO 103
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gly Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly
            20                  25                  30

<210> SEQ ID NO 104
<211> LENGTH: 20
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 104

Gly Gly Gly Gly Ser Gly Gly Gly Gly Ser Gly Gly Gly Gly Ser Gly
1               5                   10                  15

Gly Gly Gly Ser
            20

<210> SEQ ID NO 105
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 105

His His His His His His
1               5
```

SINGLE CHAIN VARIABLE FRAGMENT CD3 BINDING PROTEINS

CROSS-REFERENCE

This is a continuation application of U.S. application Ser. No. 15/600,264, filed May 19, 2017, and claims the benefit of U.S. Provisional Application No. 62/339,685 filed May 20, 2016, all of which are incorporated by reference herein in its entirety.

SEQUENCE LISTING

The instant application contains a Sequence Listing which has been submitted electronically in ASCII format and is hereby incorporated by reference in its entirety. Said ASCII copy, created on May 19, 2017, is named 47517-704_201_SL.TXT and is 66,042 bytes in size.

INCORPORATION BY REFERENCE

All publications, patents, and patent applications mentioned in this specification are herein incorporated by reference to the same extent as if each individual publication, patent, or patent application was specifically and individually indicated to be incorporated by reference, and as if set forth in their entireties.

BACKGROUND OF THE INVENTION

CD3 is a homodimeric or heterodimeric antigen expressed on T cells in association with the T cell receptor complex (TCR) and is required for T cell activation. Anti-CD3 antibodies have therapeutic purposes involving the activation of T cells. Present disclosure provides single chain variable fragment CD3 binding proteins, including multi-specific antibodies containing the same.

SUMMARY OF THE INVENTION

In one embodiment is disclosed a single chain variable fragment CD3 binding protein, comprising a variable heavy chain region (VH), a variable light chain region (VL), and a linker, wherein VH comprises complementarity determining regions HC CDR1, HC CDR2, and HC CDR3, wherein VL comprises complementarity determining regions LC CDR1, LC CDR2, and LC CDR3, wherein (a) the amino acid sequence of HC CDR1 is as set forth in $GX_1X_2X_3NX_4YX_5X_6N$ (SEQ ID NO. 2), $X_1$ is phenylalanine or asparagine, $X_2$ is threonine, glutamic acid or methionine, $X_3$ is phenylalanine or tyrosine, $X_4$ is lysine, threonine, glycine, asparagine or glutamic acid, $X_5$ is alanine or proline, $X_6$ is methionine, leucine, valine or isoleucine; (b) the amino acid sequence of HC CDR2 is as set forth in $RIRSX_7X_8NX_9YX_{10}TX_{11}YX_{12}DX_{13}VK$ (SEQ ID NO. 3), $X_7$ is lysine or glycine, $X_8$ is tyrosine or serine, $X_9$ is asparagine or lysine, $X_{10}$ is alanine or glutamic acid, $X_{11}$ is tyrosine or glutamic acid, $X_{12}$ is alanine or lysine, $X_{13}$ is serine, glutamic acid, aspartic acid, alanine, or glutamine; (c) the amino acid sequence of HC CDR3 is as set forth in $HX_{14}NFX_{15}X_{16}SX_{17}ISYWAX_{18}$ (SEQ ID NO. 4), $X_{14}$ is glycine, alanine, or threonine, $X_{15}$ is glycine or asparagine, $X_{16}$ is asparagine or aspartic acid, $X_{17}$ is tyrosine, histidine, proline, glutamine, leucine or glycine, $X_{18}$ is tyrosine or threonine; (d) the amino acid sequence of LC CDR1 is as set forth in $X_{19}X_{20}X_{21}X_{22}GX_{23}VX_{24}X_{25}GX_{26}YPN$ (SEQ ID NO. 5), $X_{19}$ is glycine or alanine, $X_{20}$ is serine or glutamic acid, $X_{21}$ is serine or tyrosine, $X_{22}$ is threonine, phenylalanine, lysine, or serine, $X_{23}$ is alanine or tyrosine, $X_{24}$ is threonine or valine, $X_{25}$ is serine, aspartic acid, lysine, histidine or valine, $X_{26}$ asparagine or tyrosine; (e) the amino acid sequence of LC CDR2 is as set forth in $GX_{27}X_{28}X_{29}X_{30}X_{31}P$ (SEQ ID NO. 6), $X_{27}$ is threonine or isoleucine, $X_{28}$ is lysine, glutamic acid, tyrosine, asparagine or serine, $X_{29}$ is phenylalanine, leucine, glutamic acid, isoleucine, methionine, or valine, $X_{30}$ is leucine, asparagine, or glycine, $X_{31}$ is alanine or valine; and (f) the amino acid sequence of LC CDR3 is as set forth in $X_{32}LWYX_{33}NX_{34}WX_{35}$ (SEQ ID NO. 7), $X_{32}$ is valine, threonine or alanine, $X_{33}$ is serine, aspartic acid or alanine, $X_{34}$ is arginine or serine, $X_{35}$ is valine, isoleucine or alanine, wherein $X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, $X_{16}$, $X_{17}$, $X_{18}$, $X_{19}$, $X_{20}$, $X_{21}$, $X_{22}$, $X_{23}$, $X_{24}$, $X_{25}$, $X_{26}$, $X_{27}$, $X_{28}$, $X_{29}$, $X_{30}$, $X_{31}$, $X_{32}$, $X_{33}$, $X_{34}$ and $X_{35}$ are not simultaneously phenylalanine, threonine, phenylalanine, lysine, alanine, methionine, lysine, tyrosine, asparagine, alanine, tyrosine, alanine, serine, glycine, glycine, asparagine, tyrosine, tyrosine, glycine, serine, serine, threonine, alanine, threonine, serine, asparagine, threonine, lysine, phenylalanine, leucine, alanine, valine, serine, arginine, and valine respectively.

In some embodiments, the single chain variable fragment CD3 binding protein comprises the following formula: f1-r1-f2-r2-f3-r3-f4-r4-f5-r5-f6-r6-f7, wherein, r1 is SEQ ID NO: 2; r2 is SEQ ID NO: 3; r3 is SEQ ID NO: 4; r4 is SEQ ID NO:5; r5 is SEQ ID NO:6; and r6 is SEQ ID NO:7; and wherein $f_1$, $f_2$, $f_3$, $f_4$, and $f_5$ are framework residues selected so that said protein is at least eighty percent identical to the amino acid sequence set forth in SEQ ID NO: 22.

In some embodiments, the single chain variable fragment CD3 binding protein comprises an amino acid sequence wherein r1 comprises SEQ ID NO. 29, SEQ ID NO. 30, SEQ ID NO. 31, SEQ ID NO. 32, SEQ ID NO. 33, SEQ ID NO. 34, SEQ ID NO. 35, SEQ ID NO. 36, SEQ ID NO. 37, SEQ ID NO. 38, SEQ ID NO. 39, or SEQ ID NO. 40. In some embodiments, the single chain variable fragment CD3 binding protein comprises an amino acid sequence wherein r2 comprises SEQ ID NO. 41, SEQ ID NO. 42, SEQ ID NO. 43, SEQ ID NO. 44, SEQ ID NO. 45, SEQ ID NO. 46, SEQ ID NO. 47, SEQ ID NO. 48, SEQ ID NO. 49, or SEQ ID NO. 50. In some embodiments, the single chain variable fragment CD3 binding protein comprises an amino acid sequence wherein r3 comprises SEQ ID NO. 51, SEQ ID NO. 52, SEQ ID NO. 53, SEQ ID NO. 54, SEQ ID NO. 55, SEQ ID NO. 56, SEQ ID NO. 57, SEQ ID NO. 58, SEQ ID NO. 50, or SEQ ID NO. 60. In some embodiments, the single chain variable fragment CD3 binding protein comprises an amino acid sequence wherein r4 comprises SEQ ID NO. 61, SEQ ID NO. 62, SEQ ID NO. 63, SEQ ID NO. 64, SEQ ID NO. 65, SEQ ID NO. 66, SEQ ID NO. 67, SEQ ID NO. 68, SEQ ID NO. 69, SEQ ID NO. 70, SEQ ID NO. 71, SEQ ID NO. 72, or SEQ ID NO. 73 In some embodiments, the single chain variable fragment CD3 binding protein comprises an amino acid sequence wherein r5 comprises SEQ ID NO. 74, SEQ ID NO. 75, SEQ ID NO. 76, SEQ ID NO. 77, SEQ ID NO. 78, SEQ ID NO. 79, SEQ ID NO. 80, SEQ ID NO. 81, SEQ ID NO. 82, SEQ ID NO. 83, SEQ ID NO. 84, SEQ ID NO. 85, or SEQ ID NO. 86. In some embodiments, the single chain variable fragment CD3 binding protein comprises an amino acid sequence wherein r6 comprises SEQ ID NO. 87, SEQ ID NO. 88, SEQ ID NO. 89, SEQ ID NO. 90, SEQ ID NO. 91, SEQ ID NO. 92, or SEQ ID NO. 93. In some embodiments, the single chain variable fragment CD3 binding protein comprises an amino acid sequence wherein r1 is SEQ ID NO. 39, r2 is SEQ ID NO. 49, r3 is SEQ ID NO. 51, r4 is SEQ ID NO. 61, r5 is SEQ ID NO. 86, and r6 is SEQ ID NO. 87. In some embodiments, the single chain variable fragment CD3 binding protein comprises an amino acid sequence wherein r1 is SEQ ID NO. 30, r2 is SEQ ID NO. 43, r4 is SEQ ID NO. 64, and r6 is SEQ ID NO. 89. In some embodiments, the single chain variable fragment CD3 binding protein comprises an amino acid sequence wherein r3 is SEQ ID NO. 55, r4 is SEQ ID NO. 67, r5 is SEQ ID NO. 77, and r6 is SEQ ID NO. 92. In some embodiments, the single chain variable fragment CD3 binding protein comprises an amino acid sequence wherein r1 is SEQ ID NO. 31, r2 is SEQ ID NO. 42, r3 is SEQ ID NO. 60, r4 is SEQ ID NO. 64, r5 is SEQ ID NO. 79, and r6 is SEQ ID NO. 91. In some embodiments, the single chain variable fragment CD3 binding protein comprises an amino acid sequence wherein r1 is SEQ ID NO. 35, r2 is SEQ ID NO. 46, r3 is SEQ ID NO. 56, r4 is SEQ ID NO. 68, and r5 is SEQ ID NO. 75. In some embodiments, the single chain variable fragment CD3 binding protein comprises an amino acid sequence wherein r1 is SEQ ID NO. 32, r2 is SEQ ID NO. 47, r3 is SEQ ID NO. 56, r4 is SEQ ID NO. 65, r5 is SEQ ID NO. 80, and r6 is SEQ ID NO. 87. In some embodiments, the single chain variable fragment CD3 binding protein comprises an amino acid sequence wherein r1 is SEQ ID NO. 29, r2 is SEQ ID NO. 44, r3 is SEQ ID NO. 52, r4 is SEQ ID NO. 73, and r5 is SEQ ID NO. 76. In some embodiments, the single chain variable fragment CD3 binding protein comprises an amino acid sequence wherein r1 is SEQ ID NO. 33, r2 is SEQ ID NO. 48, r3 is SEQ ID NO. 57, r4 is SEQ ID NO. 69, and r5 is SEQ ID NO. 74. In some embodiments, the single chain variable fragment CD3 binding protein comprises an amino acid sequence wherein r1 is SEQ ID NO. 38, r4 is SEQ ID NO. 62, and r5 is SEQ ID NO. 81. In some embodiments, the single chain variable fragment CD3 binding protein comprises an amino acid sequence wherein r1 is SEQ ID NO. 37, r3 is SEQ ID NO. 53, r4 is SEQ ID NO. 70, r5 is SEQ ID NO. 82, and r6 is SEQ ID NO. 88. In some embodiments, the single chain variable fragment CD3 binding protein comprises an amino acid sequence wherein r1 is SEQ ID NO. 34, r2 is SEQ ID NO. 47, r3 is SEQ ID NO. 56, r4 is SEQ ID NO. 68 and r5 is SEQ ID NO. 75. In some embodiments, the single chain variable fragment CD3 binding protein comprises an amino acid sequence wherein r1 is SEQ ID NO. 29, r3 is SEQ ID NO. 54, r4 is SEQ ID NO. 71 and r5 is SEQ ID NO. 83. In some embodiments, the single chain variable fragment CD3 binding protein comprises an amino acid sequence wherein r1 is SEQ ID NO. 33, r2 is SEQ ID NO. 41, r4 is SEQ ID NO. 63, r5 is SEQ ID NO. 84 and r6 is SEQ ID NO. 90. In some embodiments, the single chain variable fragment CD3 binding protein comprises an amino acid sequence wherein r1 is SEQ ID NO. 30, r2 is SEQ ID NO. 44, r3 is SEQ ID NO. 58, r4 is SEQ ID NO. 66 and r5 is SEQ ID NO. 85. In some embodiments, the single chain variable fragment CD3 binding protein comprises an amino acid sequence wherein r1 is SEQ ID NO. 40, r2 is SEQ ID NO. 45, r3 is SEQ ID NO. 56, r5 is SEQ ID NO. 78 and r6 is SEQ ID NO. 93. In some embodiments, the single chain variable fragment CD3 binding protein comprises an amino acid sequence wherein r1 is SEQ ID NO. 36, r2 is SEQ ID NO. 50, r3 is SEQ ID NO. 59, r4 is SEQ ID NO. 72 and r5 is SEQ ID NO. 75.

In some embodiments, the single chain variable fragment CD3 binding protein has an amino acid sequence selected from SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 94, and SEQ ID NO. 95. In some embodiments, the single chain variable fragment CD3 binding protein has the amino acid sequence set forth as SEQ ID NO. 8. In some embodiments, the single chain variable fragment CD3 binding protein has the amino acid sequence set forth as SEQ ID NO. 9. In some embodiments, the single chain variable fragment CD3 binding protein has the amino acid sequence set forth as SEQ ID NO. 14. In some embodiments, the single chain variable fragment CD3 binding protein has the amino acid sequence set forth as SEQ ID NO. 19. In some embodiments, the single chain variable fragment CD3 binding protein has the amino acid sequence set forth as SEQ ID NO. 94. In some embodiments, the single chain variable fragment CD3 binding protein comprises an amino acid sequence comprising a linker, wherein said linker comprises the amino acid sequence as set forth in GGGGSGGGGSGGGGS (SEQ ID NO: 1). In some embodiments, the single chain variable fragment CD3 binding protein binds to CD3 selected from human CD3 and cynomolgus CD3. In some embodiments, the single chain variable fragment CD3 binding protein binds to human CD3 and cynomolgus CD3 with comparable binding affinity (Kd). In some embodiments, the single chain variable fragment CD3 binding protein binds to human CD3 with a human Kd (hKd) between about 1 nM and about 200 nM and to cynomolgus CD3 with a cynomolgus Kd (cKd) between about 1 nM and about 300 nM. In some embodiments, the hKd and the cKd are between about 3 nM to about 5 nM, about 6 nM to about 10 nM, about 11 nM to about 20 nM, about 25 nM to about 40 nM, about 40 nM to about 60 nM, about 70 nM to about 90 nM, about 100 nM to about 120 nM, about 125 nM to about 140 nM, about 145 nM to about 160 nM, about 170 nM and to about 200 nM, about 210 nM to about 250 nM, about 260 nM to about 300 nM.

In some embodiments, the single chain variable fragment CD3 binding protein binds to human CD3 with a human Kd (hKd), binds to cynomolgus CD3 with a cynomolgus Kd (cKd), and the hKd and the cKd are about the same as the binding affinity towards CD3 of a protein which has the sequence as set forth in wt anti-CD3 (SEQ ID NO. 22). In some embodiments, the single chain variable fragment CD3 binding protein binds to human CD3 with a human Kd (hKd), binds to cynomolgus CD3 with a cynomolgus Kd (cKd), and the hKd and the cKd are between about 1.5-fold to about 2-fold higher than the binding affinity towards CD3 of a protein which has the sequence as set forth in wt anti-CD3 (SEQ ID NO. 22). In some embodiments, the single chain variable fragment CD3 binding protein binds to human CD3 with a human Kd (hKd), binds to cynomolgus CD3 with a cynomolgus Kd (cKd), and the hKd and the cKd are between about 3-fold to about 5-fold higher than the binding affinity towards CD3 of a protein which has the sequence as set forth in wt anti-CD3 (SEQ ID NO. 22). In some embodiments, the single chain variable fragment CD3 binding protein binds to human CD3 with a human Kd (hKd), binds to cynomolgus CD3 with a cynomolgus Kd (cKd), and the hKd and the cKd are between about 6-fold to about 15-fold higher than the binding affinity towards CD3 of a protein which has the sequence as set forth in wt anti-CD3 (SEQ ID NO. 22). In some embodiments, the single chain variable fragment CD3 binding protein binds to human CD3 with a human Kd (hKd), binds to cynomolgus CD3 with a cynomolgus Kd (cKd), and the hKd and the cKd are between about 20-fold to about 50-fold higher than the binding affinity towards CD3 of a protein which has the sequence as set forth in wt anti-CD3 (SEQ ID NO. 22).

In some embodiments, the single chain variable fragment CD3 binding protein has the amino acid sequence set forth as SEQ ID NO. 8, and the hKd and cKd are about the same as the binding affinity towards CD3 of a protein which has the sequence as set forth in wt anti-CD3 (SEQ ID NO. 22). In some embodiments, the single chain variable fragment CD3 binding protein has the amino acid sequence set forth as SEQ ID NO. 8, and the hKd and the cKd are between about 3 nM and about 5 nM. In some embodiments, the single chain variable fragment CD3 binding protein has the amino acid sequence set forth as SEQ ID NO. 9, and the hKd and the cKd are about the same as the binding affinity towards CD3 of a protein which has the sequence as set forth in wt anti-CD3 (SEQ ID NO. 22). In some embodiments, the single chain variable fragment CD3 binding protein has the amino acid sequence set forth as SEQ ID NO. 9, and the hKd and the cKd are between about 3 nM and about 5 nM. In some embodiments, the single chain variable fragment CD3 binding protein has the amino acid sequence set forth as SEQ ID NO. 10, and the hKd and cKd are about the same as the binding affinity towards CD3 of a protein which has the sequence as set forth in wt anti-CD3 (SEQ ID NO. 22). In some embodiments, the single chain variable fragment CD3 binding protein has the amino acid sequence set forth as SEQ ID NO. 10, and the hKd and the cKd are between about 3 nM and about 5 nM. In some embodiments, the single chain variable fragment CD3 binding protein has the amino acid sequence set forth as SEQ ID NO. 11, and wherein the hKd and cKd are about about the same as the binding affinity towards CD3 of a protein which has the sequence as set forth in wt anti-CD3 (SEQ ID NO. 22). In some embodiments, the single chain variable fragment CD3 binding protein has the amino acid sequence set forth as SEQ ID NO. 11, and the hKd and the cKd are between about 3 nM and about 5 nM. In some embodiments, the single chain variable fragment CD3 binding protein has the amino acid sequence set forth as SEQ ID NO. 12, and the hKd and cKd are between about 1.5-fold to about 2-fold higher than the binding affinity towards CD3 of a protein which has the sequence as set forth in wt anti-CD3 (SEQ ID NO. 22). In some embodiments, the single chain variable fragment CD3 binding protein has the amino acid sequence set forth as SEQ ID NO. 12, and the hKd and the cKd are between about 6 nM and about 10 nM. In some embodiments, the single chain variable fragment CD3 binding protein has the amino acid sequence set forth as SEQ ID NO. 13, and the hKd and the cKd are between about 1.5-fold to about 2-fold higher than the binding affinity towards CD3 of a protein which has the sequence as set forth in wt anti-CD3 (SEQ ID NO. 22). In some embodiments, the single chain variable fragment CD3 binding protein has the amino acid sequence set forth as SEQ ID NO. 13, and the hKd and the cKd are between about 6 nM and about 10 nM. In some embodiments, the single chain variable fragment CD3 binding protein has the amino acid sequence set forth as SEQ ID NO. 14, and the hKd and the cKd are about 3-fold to about 5-fold higher than the binding affinity towards CD3 of a protein which has the sequence as set forth in wt anti-CD3 (SEQ ID NO. 22). In some embodiments, the single chain variable fragment CD3 binding protein has the amino acid sequence set forth as SEQ ID NO. 14, and the hKd and the cKd are between about 11 nM and 20 nM. In some embodiments, the single chain variable fragment CD3 binding protein has the amino acid sequence set forth as SEQ ID NO. 15, and the hKd and cKd are about 6-fold to about 15-fold higher than the binding affinity towards CD3 of a protein which has the sequence as set forth in wt anti-CD3 (SEQ ID NO. 22). In some embodiments, the single chain variable fragment CD3 binding protein has the amino acid sequence set forth as SEQ ID NO. 15, and the hKd and the cKd are between about 25 nM and about 40 nM. In some embodiments, the single chain variable fragment CD3 binding protein has the amino acid sequence set forth as SEQ ID NO. 16, and the hKd and the cKd are about 3-fold to about 5-fold higher than the binding affinity towards CD3 of a protein which has the sequence as set forth in wt anti-CD3 (SEQ ID NO. 22). In some embodiments, the single chain variable fragment CD3 binding protein has the amino acid sequence set forth as SEQ ID NO. 16, and the hKd iand the cKd are between about 11 nM and 20 nM. In some embodiments, the single chain variable fragment CD3 binding protein has the amino acid sequence set forth as SEQ ID NO. 17, and the hKd and cKd are about 6-fold to about 15-fold higher than the binding affinity towards CD3 of a protein which has the sequence as set forth in wt anti-CD3 (SEQ ID NO. 22). In some embodiments, the single chain variable fragment CD3 binding protein has the amino acid sequence set forth as SEQ ID NO. 17, and the hKd and the cKd are between about 40 nM and about 60 nM. In some embodiments, the single chain variable fragment CD3 binding protein has the amino acid sequence set forth as SEQ ID NO. 18, and the hKd and cKd are about 3-fold to about 5-fold higher than the binding affinity towards CD3 of a protein which has the sequence as set forth in wt anti-CD3 (SEQ ID NO. 22). In some embodiments, the single chain variable fragment CD3 binding protein has the amino acid sequence set forth as SEQ ID NO. 18, and the hKd and the cKd are between about 11 nM and 20 nM. In some embodiments, the single chain variable fragment CD3 binding protein has the amino acid sequence set forth as SEQ ID NO. 19, and the hKd and cKd are about 6-fold to about 15-fold higher than the binding affinity towards CD3 of a protein which has the sequence as set forth in wt anti-CD3 (SEQ ID NO. 22). In some embodiments, the single chain variable fragment CD3 binding protein has the amino acid sequence set forth as SEQ ID NO. 19, and the hKd and the cKd are between about 40 nM and 60 nM. In some embodiments, the single chain variable fragment CD3 binding protein has the amino acid sequence set forth as SEQ ID NO. 20, and the hKd and the cKd are about 3-fold to about 5-fold higher than the binding affinity towards CD3 of a protein which has the sequence as set forth in wt anti-CD3 (SEQ ID NO. 22). In some embodiments, the single chain variable fragment CD3 binding protein has the amino acid sequence set forth as SEQ ID NO. 20, and the hKd and the cKd are between about 11 nM and about 20 nM. In some embodiments, the single chain variable fragment CD3 binding protein has the amino acid sequence set forth as SEQ ID NO. 21, and the hKd and the cKd are about 20-fold to about 50-fold higher than the binding affinity towards CD3 of a protein which has the sequence as set forth in wt anti-CD3 (SEQ ID NO. 22). In some embodiments, the single chain variable fragment CD3 binding protein has the amino acid sequence set forth as SEQ ID NO. 21, and the hKd and the cKd are between about 125 nM and about 140 nM. In some embodiments, the single chain variable fragment CD3 binding protein has the amino acid sequence set forth as SEQ ID NO. 94, and wherein the hKd and the cKd are about 20-fold to about 50-fold higher than the binding affinity towards CD3 of a protein which has the sequence as set forth in wt anti-CD3 (SEQ ID NO. 22). In some embodiments, the single chain variable fragment CD3 binding protein has the amino acid sequence set forth as SEQ ID NO. 94, and the hKd and the cKd are between about 100 nM and about 120 nM. In some embodiments, the single chain variable fragment CD3 binding protein has the amino acid sequence set forth as SEQ ID NO. 95, and the hKd and the cKd are about 20-fold to about 50-fold higher than the binding affinity towards CD3 of a protein which has the sequence as set forth in wt anti-CD3 (SEQ ID NO. 22). In some embodiments, the single chain variable fragment CD3 binding protein has the amino acid sequence set forth as SEQ ID NO. 95, and the hKd and the cKd are between about 100 nM and about 120 nM.

Provided herein in another embodiment is a single chain variable fragment CD3 binding protein comprising the sequence set forth as SEQ ID NO. 22 (wt anti-CD3) wherein one or more amino acid residues selected from amino acid positions 27, 28, 29, 31, 33, 34, 54, 55, 57, 59, 61, 63, 65, 102, 105, 106, 108, 114, 163, 164, 165, 166, 168, 170, 171, 173, 193, 194, 195, 196, 197, 231, 235, 237, and 239 are substituted, wherein amino acid position 27 is substituted with asparagine, amino acid position 28 is substituted with glutamic acid, or methionine, amino acid position 29 is substituted with tyrosine, amino acid position 31 is substituted with asparagine, glycine, glutamic acid or threonine, amino acid position 33 is substituted with proline, amino acid position 34 is substituted with valine, leucine or isoleucine, amino acid position 54 is substituted with glycine, amino acid position 55 is substituted with serine, amino acid position 57 is substituted with lysine, amino acid position 59 is substituted with glutamic acid, amino acid position 61 is substituted with glutamic acid, amino acid position 63 is substituted with lysine, amino acid position 65 is substituted with aspartic acid, glutamic acid, alanine, or glutamine, amino acid position 102 is substituted with alanine or threonine, amino acid position 105 is substituted with asparagine, amino acid position 106 is substituted with aspartic acid, amino acid position 108 is substituted with histidine, proline, glutamine, glycine, or leucine, amino acid position 114 is substituted with threonine, amino acid position 163 is substituted with alanine, amino acid position 164 is substituted with glutamic acid, amino acid position 165 is substituted with tyrosine, amino acid position 166 is substituted with phenylalanine, lysine, or serine, amino acid position 168 is substituted with tyrosine, amino acid position 170 is substituted with valine, amino acid position 171 is substituted with aspartic acid, lysine, valine, or histidine, amino acid position 173 is substituted with tyrosine, amino acid position 193 is substituted with isoleucine, amino acid position 194 is substituted with glutamic acid, tyrosine, asparagine, or serine, amino acid position 195 is substituted with leucine, glutamic acid, isoleucine, methionine, or valine, amino acid position 196 is substituted with asparagine, or glycine, amino acid position 197 is substituted with valine, amino acid position 231 is substituted with threonine, or alanine, amino acid position 235 is substituted with aspartic acid, or alanine, amino acid position 237 is substituted with serine, and amino acid position 239 is substituted with alanine, or isoleucine. In some embodiments, the single chain variable fragment CD3 binding protein comprises one or more additional substitutions in amino acid positions other than positions 27, 28, 29, 31, 33, 34, 54, 55, 57, 59, 61, 63, 65, 102, 105, 106, 108, 114, 163, 164, 165, 166, 168, 170, 171, 173, 193, 194, 195, 196, 197, 231, 235, 237, and 239. In some embodiments, the single chain variable fragment CD3 binding protein comprises a substitution in position 27. In some embodiments, the single chain variable fragment CD3 binding protein comprises a substitution in position 28. In some embodiments, the single chain variable fragment CD3 binding protein comprises a substitution in position 29. In some embodiments, the single chain variable fragment CD3 binding protein comprises a substitution in position 31. In some embodiments, the single chain variable fragment CD3 binding protein comprises a substitution in position 33. In some embodiments, the single chain variable fragment CD3 binding protein comprises a substitution in position 34. In some embodiments, the single chain variable fragment CD3 binding protein comprises a substitution in position 54. In some embodiments, the single chain variable fragment CD3 binding protein comprises a substitution in position 55. In some embodiments, the single chain variable fragment CD3 binding protein comprises a substitution in position 57. In some embodiments, the single chain variable fragment CD3 binding protein comprises a substitution in position 59. In some embodiments, the single chain variable fragment CD3 binding protein comprises a substitution in position 61. In some embodiments, the single chain variable fragment CD3 binding protein comprises a substitution in position 63. In some embodiments, the single chain variable fragment CD3 binding protein comprises a substitution in position 65. In some embodiments, the single chain variable fragment CD3 binding protein comprises a substitution in position 102. In some embodiments, the single chain variable fragment CD3 binding protein comprises a substitution in position 105. In some embodiments, the single chain variable fragment CD3 binding protein comprises a substitution in position 106. In some embodiments, the single chain variable fragment CD3 binding protein comprises a substitution in position 108. In some embodiments, the single chain variable fragment CD3 binding protein comprises a substitution in position 114. In some embodiments, the single chain variable fragment CD3 binding protein comprises a substitution in position 163. In some embodiments, the single chain variable fragment CD3 binding protein comprises a substitution in position 164. In some embodiments, the single chain variable fragment CD3 binding protein comprises a substitution in position 165. In some embodiments, the single chain variable fragment CD3 binding protein comprises a substitution in position 166. In some embodiments, the single chain variable fragment CD3 binding protein comprises a substitution in position 168. In some embodiments, the single chain variable fragment CD3 binding protein comprises a substitution in position 170. In some embodiments, the single chain variable fragment CD3 binding protein comprises a substitution in position 171. In some embodiments, the single chain variable fragment CD3 binding protein comprises a substitution in position 173. In some embodiments, the single chain variable fragment CD3 binding protein comprises a substitution in position 193. In some embodiments, the single chain variable fragment CD3 binding protein comprises a substitution in position 194. In some embodiments, the single chain variable fragment CD3 binding protein comprises a substitution in position 195. In some embodiments, the single chain variable fragment CD3 binding protein comprises a substitution in position 196. In some embodiments, the single chain variable fragment CD3 binding protein comprises a substitution in position 197. In some embodiments, the single chain variable fragment CD3 binding protein comprises a substitution in position 231. In some embodiments, the single chain variable fragment CD3 binding protein comprises a substitution in position 235. In some embodiments, the single chain variable fragment CD3 binding protein comprises a substitution in position 237. In some embodiments, the single chain variable fragment CD3 binding protein comprises a substitution in position 239. In some embodiments, the single chain variable fragment CD3 binding protein comprises substitutions in positions 34, 65, 102, 163, 197, and 231. In some embodiments, the single chain variable fragment CD3 binding protein comprises substitutions in positions 28, 57, 166, and 235. In some embodiments, the single chain variable fragment CD3 binding protein comprises substitutions in positions 108, 168, 194, and 239. In some embodiments, the single chain variable fragment CD3 binding protein comprises substitutions in positions 28, 55, 114, 166, 195, and 237. In some embodiments, the single chain variable fragment CD3 binding protein comprises substitutions in positions 31, 63, 108, 170, and 194. In some embodiments, the single chain variable fragment CD3 binding protein comprises substitutions in positions 29, 65, 108, 166, 195, and 231. In some embodiments, the single chain variable fragment CD3 binding protein comprises substitutions in positions 27, 59, 102, 173, and 194. In some embodiments, the single chain variable fragment CD3 binding protein comprises substitutions in positions 31, 65, 108, 171, and 193. In some embodiments, the single chain variable fragment CD3 binding protein comprises substitutions in positions 34, 164, and 195. In some embodiments, the single chain variable fragment CD3 binding protein comprises substitutions in positions 33, 105, 171, 195, and 231. In some embodiments, the single chain variable fragment CD3 binding protein comprises substitutions in positions 31, 65, 108, 170, and 194. In some embodiments, the single chain variable fragment CD3 binding protein comprises substitutions in positions 27, 106, 171, and 195. In some embodiments, the single chain variable fragment CD3 binding protein comprises substitutions in positions 31, 54, 165, 196, and 235. In some embodiments, the single chain variable fragment CD3 binding protein comprises substitutions in positions 28, 59, 108, 166, and 196. In some embodiments, the single chain variable fragment CD3 binding protein comprises substitutions in positions 34, 61, 108, 194, and 239. In some embodiments, the single chain variable fragment CD3 binding protein comprises substitutions in positions 31, 65, 108, 171, and 194.

In some embodiments, the single chain variable fragment CD3 binding protein comprises a sequence wherein amino acid positions 34, 65, 102, 163, 197, and 231 are substituted, and wherein the hKd and the cKd are about the same as the binding affinity towards CD3 of a protein which has the sequence as set forth in wt anti-CD3 (SEQ ID NO. 22). In some embodiments, the single chain variable fragment CD3 binding protein comprises a sequence wherein amino acid positions 34, 65, 102, 163, 197, and 231 are substituted, and wherein the hKd and the cKd are between about 3 nM and about 5 nM. In some embodiments, the single chain variable fragment CD3 binding protein comprises a sequence wherein amino acid positions 28, 57, 166, and 235 are substituted, and wherein the hKd and the cKd are about the same as the binding affinity towards CD3 of a protein which has the sequence as set forth in wt anti-CD3 (SEQ ID NO. 22). In some embodiments, the single chain variable fragment CD3 binding protein comprises a sequence wherein amino acid positions 28, 57, 166, and 235 are substituted, and wherein the hKd and the cKd are between about 3 nM and about 5 nM.

In some embodiments, the single chain variable fragment CD3 binding protein comprises a sequence wherein amino acid positions 108, 168, 194, and 239 are substituted, and wherein the hKd and the cKd are about the same as the binding affinity towards CD3 of a protein which has the sequence as set forth in wt anti-CD3 (SEQ ID NO. 22). In some embodiments, the single chain variable fragment CD3 binding protein comprises a sequence wherein amino acid positions 108, 168, 194, and 239 are substituted, and wherein the hKd and the cKd are between about 3 nM and about 5 nM. In some embodiments, the single chain variable fragment CD3 binding protein comprises a sequence wherein amino acid positions 28, 55, 114, 166, 195, and 237 are substituted, and wherein the hKd and the cKd are about the same as the binding affinity towards CD3 of a protein which has the sequence as set forth in wt anti-CD3 (SEQ ID NO. 22). In some embodiments, the single chain variable fragment CD3 binding protein comprises a sequence wherein amino acid positions 28, 55, 114, 166, 195, and 237 are substituted, and wherein the hKd and the cKd are between about 3 nM and about 5 nM. In some embodiments, the single chain variable fragment CD3 binding protein comprises a sequence wherein amino acid positions 31, 63, 108, 170, and 194 are substituted, and wherein the hKd and the cKd are between about 1.5-fold to about 2-fold higher than the binding affinity towards CD3 of a protein which has the sequence as set forth in wt anti-CD3 (SEQ ID NO. 22). In some embodiments, the single chain variable fragment CD3 binding protein comprises a sequence wherein amino acid positions 31, 63, 108, 170, and 194 are substituted, and wherein the hKd and the cKd are between about 6 nM and about 10 nM. In some embodiments, the single chain variable fragment CD3 binding protein comprises a sequence wherein amino acid positions 29, 65, 108, 166, 195, and 231 are substituted, and wherein the hKd and the cKd are between about 1.5-fold to about 2-fold higher than the binding affinity towards CD3 of a protein which has the sequence as set forth in wt anti-CD3 (SEQ ID NO. 22). In some embodiments, the single chain variable fragment CD3 binding protein comprises a sequence wherein amino acid positions 29, 65, 108, 166, 195, and 231 are substituted, and wherein the hKd and the cKd are between about 6 nM and about 10 nM. In some embodiments, the single chain variable fragment CD3 binding protein comprises a sequence wherein amino acid positions 27, 59, 102, 173, and 194 are substituted, and wherein the hKd and the cKd are about 3-fold to about 5-fold higher than the binding affinity towards CD3 of a protein which has the sequence as set forth in wt anti-CD3 (SEQ ID NO. 22). In some embodiments, the single chain variable fragment CD3 binding protein comprises a sequence wherein amino acid positions 27, 59, 102, 173, and 194 are substituted, and wherein the hKd and the cKd are between about 11 nM and 20 nM. In some embodiments, the single chain variable fragment CD3 binding protein comprises a sequence wherein amino acid positions 31, 65, 108, 171, and 193 are substituted, and wherein the hKd and the cKd are about 6-fold to about 15-fold higher than the binding affinity towards CD3 of a protein which has the sequence as set forth in wt anti-CD3 (SEQ ID NO. 22). In some embodiments, the single chain variable fragment CD3 binding protein comprises a sequence wherein amino acid positions 31, 65, 108, 171, and 193 are substituted, and wherein the hKd and the cKd are between about 25 nM and about 40 nM. In some embodiments, the single chain variable fragment CD3 binding protein comprises a sequence wherein amino acid positions 34, 164, and 195 are substituted, and wherein the hKd and the cKd are about 3-fold to about 5-fold higher than the binding affinity towards CD3 of a protein which has the sequence as set forth in wt anti-CD3 (SEQ ID NO. 22). In some embodiments, the single chain variable fragment CD3 binding protein comprises a sequence wherein amino acid positions 34, 164, and 195 are substituted, and wherein the hKd and the cKd are between about 11 nM and 20 nM. In some embodiments, the single chain variable fragment CD3 binding protein comprises a sequence wherein amino acid positions 33, 105, 171, 195, and 231 are substituted, and wherein the hKd and the cKd are about 6-fold to about 15-fold higher than the binding affinity towards CD3 of a protein which has the sequence as set forth in wt anti-CD3 (SEQ ID NO. 22). In some embodiments, the single chain variable fragment CD3 binding protein comprises a sequence wherein amino acid positions 33, 105, 171, 195, and 231 are substituted, and wherein the hKd and the cKd are between about 40 nM and about 60 nM. In some embodiments, the single chain variable fragment CD3 binding protein comprises a sequence wherein amino acid positions 31, 65, 108, 170, and 194 are substituted, and wherein the hKd and the cKd are about 3-fold to about 5-fold higher than the binding affinity towards CD3 of a protein which has the sequence as set forth in wt anti-CD3 (SEQ ID NO. 22). In some embodiments, the single chain variable fragment CD3 binding protein comprises a sequence wherein amino acid positions 31, 65, 108, 170, and 194 are substituted, and wherein the hKd and the cKd are between about 11 nM and 20 nM. In some embodiments, the single chain variable fragment CD3 binding protein comprises a sequence wherein amino acid positions 27, 106, 171, and 195 are substituted, and wherein the hKd and the cKd are about 6-fold to about 15-fold higher than the binding affinity towards CD3 of a protein which has the sequence as set forth in wt anti-CD3 (SEQ ID NO. 22). In some embodiments, the single chain variable fragment CD3 binding protein comprises a sequence wherein amino acid positions 27, 106, 171, and 195 are substituted, and wherein the hKd and the cKd are between about 40 nM and 60 nM. In some embodiments, the single chain variable fragment CD3 binding protein comprises a sequence wherein amino acid positions 31, 54, 165, 196, and 235 are substituted, and wherein the hKd and the cKd are about 3-fold to about 5-fold higher than the binding affinity towards CD3 of a protein which has the sequence as set forth in wt anti-CD3 (SEQ ID NO. 22). In some embodiments, the single chain variable fragment CD3 binding protein comprises a sequence wherein amino acid positions 31, 54, 165, 196, and 235 are substituted (10B2), and wherein the hKd and the cKd are between about 11 nM and about 20 nM. In some embodiments, the single chain variable fragment CD3 binding protein comprises a sequence wherein amino acid positions 28, 59, 108, 166, and 196 are substituted, and wherein the hKd and the cKd are about 25-fold to about 50-fold higher than the binding affinity towards CD3 of a protein which has the sequence as set forth in wt anti-CD3 (SEQ ID NO. 22). In some embodiments, the single chain variable fragment CD3 binding protein comprises a sequence wherein amino acid positions 28, 59, 108, 166, and 196 are substituted, and wherein the hKd and the cKd are between about 125 nM and about 140 nM. In some embodiments, the single chain variable fragment CD3 binding protein comprises a sequence wherein amino acid positions 34, 61, 108, 194, and 239 are substituted, and wherein the hKd and the cKd are about 20-fold to about 50-fold higher than the binding affinity towards CD3 of a protein which has the sequence as set forth in wt anti-CD3 (SEQ ID NO. 22). In some embodiments, the single chain variable fragment CD3 binding protein comprises a sequence wherein amino acid positions 34, 61, 108, 194, and 239 are substituted, and wherein the hKd and the cKd are between about 100 nM and about 120 nM. In some embodiments, the single chain variable fragment CD3 binding protein comprises a sequence wherein amino acid positions 31, 65, 108, 171, and 194 are substituted, and wherein the hKd and the cKd are about 20-fold to about 50-fold higher than the binding affinity towards CD3 of a protein which has the sequence as set forth in wt anti-CD3 (SEQ ID NO. 22). In some embodiments, the single chain variable fragment CD3 binding protein comprises a sequence wherein amino acid positions 31, 65, 108, 171, and 194 are substituted, and wherein the hKd and the cKd are between about 100 nM and about 120 nM.

Provided herein in a further embodiment is a single chain variable fragment CD3 binding protein comprising an amino acid sequence as set forth in wt anti-CD3 (SEQ ID NO: 22), comprising a variable heavy chain region (VH), a variable light chain region (VL), a linker comprising the amino acid sequence as set forth in GGGGSGGGGSGGGGS (SEQ ID NO: 1), wherein VH comprises complementarity determining regions CDR1, CDR2, and CDR3, wherein VL comprises complementarity determining regions LC CDR1, LC CDR2, and LC CDR3, comprising at least one mutation in CDR1, CDR2 or CDR3 of VH, and LC CDR1, LC CDR2 or LC CDR3 of VL, wherein the at least one mutation is not in amino acid positions 26, 30, 32, 35, 50, 51, 52, 53, 56, 58, 60, 62, 64, 66, 67, 101, 103, 104, 107, 109, 110, 111, 112, 113, 167, 169, 172, 174, 175, 176, 192, 198, 232, 233, 234, 236, or 238. In some embodiments, the single chain variable fragment CD3 binding protein comprises at least one mutation in amino acid position selected from 27, 28, 29, 31, 33, 34, 54, 55, 57, 59, 61, 63, 65, 102, 105, 106, 108, 114, 163, 164, 165, 166, 168, 170, 171, 173, 193, 194, 195, 196, 197, 231, 235, 237, and 239. In some embodiments, amino acid position 34 is mutated to isoleucine, position 65 is mutated to glutamine, position 102 is mutated to alanine, position 163 is mutated to alanine, position 197 is mutated to valine, and position 231 is mutated to threonine. In some embodiments, amino acid position 28 is mutated to glutamic acid, position 57 is mutated to lysine, position 166 is mutated to phenylalanine, and position 235 is mutated to aspartic acid. In some embodiments, amino acid position 108 is mutated to histidine, position 168 is mutated to tyrosine, position 194 is mutated to serine, and position 239 is mutated to isoleucine. In some embodiments, amino acid position 28 is mutated to methionine, position 55 is mutated to serine, position 114 is mutated to threonine, position 166 is mutated to phenylalanine, position 195 is mutated to leucine, and position 237 is mutated to serine. In some embodiments, amino acid position 31 is mutated to threonine, position 63 is mutated to lysine, position 108 is mutated to proline, position 170 is mutated to valine, and position 194 is mutated to glutamic acid. In some embodiments, amino acid position 29 is mutated to tyrosine, position 65 is mutated to glutamic acid, position 108 is mutated to proline, position 166 is mutated to lysine, position 195 is mutated to glutamic acid, and position 231 is mutated to threonine. In some embodiments, amino acid position 27 is mutated to asparagine, position 59 is mutated to glutamic acid, position 102 is mutated to threonine, position 173 is mutated to tyrosine, and position 194 is mutated to tyrosine. In some embodiments, amino acid position amino acid position 31 is mutated to asparagine, position 65 is mutated to alanine, position 108 is mutated to glutamine, position 171 is mutated to aspartic acid, and position 193 is mutated to isoleucine. In some embodiments, amino acid position 34 is mutated to valine, position 164 is mutated to glutamic acid, and position 195 is mutated to isoleucine. In some embodiments, amino acid position 33 is mutated to proline, position 105 is mutated to asparagine, position 171 is mutated to lysine, position 195 is mutated to methionine, and position 231 is mutated to alanine. In some embodiments, amino acid position 31 is mutated to glycine, position 65 is mutated to glutamic acid, position 108 is mutated to proline, position 170 is mutated to valine, and position 194 is mutated to glutamic acid. In some embodiments, amino acid position 27 is mutated to asparagine, position 106 is mutated to aspartic acid, position 171 is mutated to histidine, and position 195 is mutated to valine. In some embodiments, amino acid position 31 is mutated to asparagine, position 54 is mutated to glycine, position 165 is mutated to tyrosine, position 196 is mutated to asparagine, and position 235 is mutated to alanine. In some embodiments, amino acid position 28 is mutated to glutamic acid, position 59 is mutated to glutamic acid, position 108 is mutated to leucine, position 166 is mutated to serine, and position 196 is mutated to glycine. In some embodiments, amino acid position 34 is substituted with leucine, amino acid position 61 is substituted with glutamic acid, amino acid position 108 is substituted with proline, amino acid position 194 is substituted with asparagine, and amino acid position 239 is substituted with alanine. In some embodiments, amino acid position 31 is substituted with glutamic acid, amino acid position 65 is substituted with aspartic acid, amino acid position 108 is substituted with glycine, amino acid position 171 is substituted with valine, and amino acid position 194 is substituted with glutamic acid.

In some embodiments, the single chain variable fragment CD3 binding protein comprises a sequence wherein amino acid position 34 is mutated to isoleucine, position 65 is mutated to glutamine, position 102 is mutated to alanine, position 163 is mutated to alanine, position 197 is mutated to valine, and position 231 is mutated to threonine, and wherein the hKd and the cKd are about the same as the binding affinity towards CD3 of a protein which has the sequence as set forth in wt anti-CD3 (SEQ ID NO. 22). In some embodiments, the single chain variable fragment CD3 binding protein comprises a sequence wherein amino acid position 34 is mutated to isoleucine, position 65 is mutated to glutamine, position 102 is mutated to alanine, position 163 is mutated to alanine, position 197 is mutated to valine, and position 231 is mutated to threonine, wherein the hKd and the cKd are between about 3 nM and 5 nM. In some embodiments, the single chain variable fragment CD3 binding protein comprises a sequence wherein amino acid position 28 is mutated to glutamic acid, position 57 is mutated to lysine, position 166 is mutated to phenylalanine, and position 235 is mutated to aspartic acid, and wherein the hKd and the cKd are about the same as the binding affinity towards CD3 of a protein which has the sequence as set forth in wt anti-CD3 (SEQ ID NO. 22). In some embodiments, the single chain variable fragment CD3 binding protein comprises a sequence wherein amino acid position 28 is mutated to glutamic acid, position 57 is mutated to lysine, position 166 is mutated to phenylalanine, and position 235 is mutated to aspartic acid, wherein the hKd and the cKd are between about 3 nM and about 5 nM. In some embodiments, the single chain variable fragment CD3 binding protein comprises a sequence wherein amino acid position 108 is mutated to histidine, position 168 is mutated to tyrosine, position 194 is mutated to serine, and position 239 is mutated to isoleucine, and wherein the hKd and the cKd are about the same as the binding affinity towards CD3 of a protein which has the sequence as set forth in wt anti-CD3 (SEQ ID NO. 22). In some embodiments, the single chain variable fragment CD3 binding protein comprises a sequence wherein amino acid position 108 is mutated to histidine, position 168 is mutated to tyrosine, position 194 is mutated to serine, and position 239 is mutated to isoleucine, wherein the hKd and the cKd are between about 3 nM and about 5 nM. In some embodiments, the single chain variable fragment CD3 binding protein comprises a sequence wherein amino acid position 28 is mutated to methionine, position 55 is mutated to serine, position 114 is mutated to threonine, position 166 is mutated to phenylalanine, position 195 is mutated to leucine, and position 237 is mutated to serine, and wherein the hKd and the cKd are about the same as the binding affinity towards CD3 of a protein which has the sequence as set forth in wt anti-CD3 (SEQ ID NO. 22). In some embodiments, the single chain variable fragment CD3 binding protein comprises a sequence wherein amino acid position 28 is mutated to methionine, position 55 is mutated to serine, position 114 is mutated to threonine, position 166 is mutated to phenylalanine, position 195 is mutated to leucine, and position 237 is mutated to serine, wherein the hKd and the cKd are between about 3 nM and about 5 nM. In some embodiments, the single chain variable fragment CD3 binding protein comprises a sequence wherein amino acid position 31 is mutated to threonine, position 63 is mutated to lysine, position 108 is mutated to proline, position 170 is mutated to valine, and position 194 is mutated to glutamic acid, and wherein the hKd and the cKd are between about 1.5-fold to about 2-fold higher than the binding affinity towards CD3 of a protein which has the sequence as set forth in wt anti-CD3 (SEQ ID NO. 22). In some embodiments, the single chain variable fragment CD3 binding protein comprises a sequence wherein amino acid position 31 is mutated to threonine, position 63 is mutated to lysine, position 108 is mutated to proline, position 170 is mutated to valine, and position 194 is mutated to glutamic acid, wherein the hKd and the cKd are between about 6 nM and about 10 nM. In some embodiments, the single chain variable fragment CD3 binding protein comprises a sequence wherein amino acid position 29 is mutated to tyrosine, position 65 is mutated to glutamic acid, position 108 is mutated to proline, position 166 is mutated to lysine, position 195 is mutated to glutamic acid, and position 231 is mutated to threonine, and wherein the hKd and the cKd are between about 1.5-fold to about 2-fold higher than the binding affinity towards CD3 of a protein which has the sequence as set forth in wt anti-CD3 (SEQ ID NO. 22). In some embodiments, the single chain variable fragment CD3 binding protein comprises a sequence wherein amino acid position 29 is mutated to tyrosine, position 65 is mutated to glutamic acid, position 108 is mutated to proline, position 166 is mutated to lysine, position 195 is mutated to glutamic acid, and position 231 is mutated to threonine, wherein the hKd and the cKd are between about 6 nM and about 10 nM. In some embodiments, the single chain variable fragment CD3 binding protein comprises a sequence wherein amino acid position 27 is mutated to asparagine, position 59 is mutated to glutamic acid, position 102 is mutated to threonine, position 173 is mutated to tyrosine, and position 194 is mutated to tyrosine, and wherein the hKd and the cKd are about 3-fold to about 5-fold higher than the binding affinity towards CD3 of a protein which has the sequence as set forth in wt anti-CD3 (SEQ ID NO. 22). In some embodiments, the single chain variable fragment CD3 binding protein comprises a sequence wherein amino acid position 27 is mutated to asparagine, position 59 is mutated to glutamic acid, position 102 is mutated to threonine, position 173 is mutated to tyrosine, and position 194 is mutated to tyrosine, wherein the hKd and the cKd are between about 11 nM and 20 nM. In some embodiments, the single chain variable fragment CD3 binding protein comprises a sequence wherein amino acid position 31 is mutated to asparagine, position 65 is mutated to alanine, position 108 is mutated to glutamine, position 171 is mutated to aspartic acid, and position 193 is mutated to isoleucine, and wherein the hKd and the cKd are about 6-fold to about 15-fold higher than the binding affinity towards CD3 of a protein which has the sequence as set forth in wt anti-CD3 (SEQ ID NO. 22). In some embodiments, the single chain variable fragment CD3 binding protein comprises a sequence wherein amino acid position 31 is mutated to asparagine, position 65 is mutated to alanine, position 108 is mutated to glutamine, position 171 is mutated to aspartic acid, and position 193 is mutated to isoleucine, wherein the hKd and the cKd are between about 25 nM and about 40 nM. In some embodiments, the single chain variable fragment CD3 binding protein comprises a sequence wherein amino acid position 34 is mutated to valine, position 164 is mutated to glutamic acid, and position 195 is mutated to isoleucine, and wherein the hKd and the cKd are about 3-fold to about 5-fold higher than the binding affinity towards CD3 of a protein which has the sequence as set forth in wt anti-CD3 (SEQ ID NO. 22). In some embodiments, the single chain variable fragment CD3 binding protein comprises a sequence wherein amino acid position 34 is mutated to valine, position 164 is mutated to glutamic acid, and position 195 is mutated to isoleucine, wherein the hKd and the cKd are between about 11 nM and 20 nM. In some embodiments, the single chain variable fragment CD3 binding protein comprises a sequence wherein amino acid position 33 is mutated to proline, position 90 is mutated to asparagine, position 105 is mutated to asparagine, position 171 is mutated to lysine, position 195 is mutated to methionine, and position 231 is mutated to alanine, and wherein the hKd and the cKd are about 6-fold to about 15-fold higher than the binding affinity towards CD3 of a protein which has the sequence as set forth in wt anti-CD3 (SEQ ID NO. 22). In some embodiments, the single chain variable fragment CD3 binding protein comprises a sequence wherein amino acid position 33 is mutated to proline, position 90 is mutated to asparagine, position 105 is mutated to asparagine, position 171 is mutated to lysine, position 195 is mutated to methionine, and position 231 is mutated to alanine, wherein the hKd and the cKd are between about 40 nM and 60 nM. In some embodiments, the single chain variable fragment CD3 binding protein comprises a sequence wherein amino acid position 31 is mutated to glycine, position 65 is mutated to glutamic acid, position 108 is mutated to proline, position 170 is mutated to valine, and position 194 is mutated to glutamic acid, and wherein the hKd and the cKd are about 3-fold to about 5-fold higher than the binding affinity towards CD3 of a protein which has the sequence as set forth in wt anti-CD3 (SEQ ID NO. 22). In some embodiments, the single chain variable fragment CD3 binding protein comprises a sequence wherein amino acid position 31 is mutated to glycine, position 65 is mutated to glutamic acid, position 108 is mutated to proline, position 170 is mutated to valine, and position 194 is mutated to glutamic acid, wherein the hKd and the cKd are between about 11 nM and 20 nM. In some embodiments, the single chain variable fragment CD3 binding protein comprises a sequence wherein amino acid position 27 is mutated to asparagine, position 106 is mutated to aspartic acid, position 171 is mutated to histidine, and position 195 is mutated to valine, and wherein the hKd and the cKd are about 6-fold to about 15-fold higher than the binding affinity towards CD3 of a protein which has the sequence as set forth in wt anti-CD3 (SEQ ID NO. 22). In some embodiments, the single chain variable fragment CD3 binding protein comprises a sequence wherein amino acid position 27 is mutated to asparagine, position 106 is mutated to aspartic acid, position 171 is mutated to histidine, and position 195 is mutated to valine, wherein the hKd and the cKd are between about 40 nM and 60 nM. In some embodiments, the single chain variable fragment CD3 binding protein comprises a sequence wherein amino acid position 31 is mutated to asparagine, position 54 is mutated to glycine, position 165 is mutated to tyrosine, position 196 is mutated to asparagine, and position 235 is mutated to alanine, and wherein the hKd and the cKd are about 3-fold to about 5-fold higher than the binding affinity towards CD3 of a protein which has the sequence as set forth in wt anti-CD3 (SEQ ID NO. 22). In some embodiments, the single chain variable fragment CD3 binding protein comprises a sequence wherein amino acid position 31 is mutated to asparagine, position 54 is mutated to glycine, position 165 is mutated to tyrosine, position 196 is mutated to asparagine, and position 235 is mutated to alanine, wherein the hKd and the cKd are between about 11 nM and about 20 nM. In some embodiments, the single chain variable fragment CD3 binding protein comprises a sequence wherein amino acid position 28 is mutated to glutamic acid, position 59 is mutated to glutamic acid, position 108 is mutated to leucine, position 166 is mutated to serine, and position 196 is mutated to glycine, and wherein the hKd and the cKd are about 20-fold to about 50-fold higher than the binding affinity towards CD3 of a protein which has the sequence as set forth in wt anti-CD3 (SEQ ID NO. 22). In some embodiments, the single chain variable fragment CD3 binding protein comprises a sequence wherein amino acid position 28 is mutated to glutamic acid, position 59 is mutated to glutamic acid, position 108 is mutated to leucine, position 166 is mutated to serine, and position 196 is mutated to glycine, wherein the hKd and the cKd are between about 125 nM and about 140 nM. In some embodiments, the single chain variable fragment CD3 binding protein comprises a sequence wherein amino acid position 34 is mutated to leucine, amino acid position 61 is mutated to glutamic acid, amino acid position 108 is mutated to proline, amino acid position 194 is mutated to asparagine, amino acid position 239 is mutated to alanine, and wherein the hKd and the cKd are about 20-fold to about 50-fold higher than the binding affinity towards CD3 of a protein which has the sequence as set forth in wt anti-CD3 (SEQ ID NO. 22). In some embodiments, the single chain variable fragment CD3 binding protein comprises a sequence wherein amino acid position 34 is mutated to leucine, amino acid position 61 is mutated to glutamic acid, amino acid position 108 is mutated to proline, amino acid position 194 is mutated to asparagine, amino acid position 239 is mutated to alanine, wherein the hKd and the cKd are between about 100 nM and about 120 nM. In some embodiments, the single chain variable fragment CD3 binding protein comprises a sequence wherein amino acid position 31 is mutated to glutamic acid, amino acid position 65 is mutated to aspartic acid, amino acid position 108 is mutated to glycine, amino acid position 171 is mutated to valine, and amino acid position 194 is mutated to glutamic acid, and wherein the hKd and the cKd are about 20-fold to about 50-fold higher than the binding affinity towards CD3 of a protein which has the sequence as set forth in wt anti-CD3 (SEQ ID NO. 22). In some embodiments, the single chain variable fragment CD3 binding protein comprises a sequence wherein amino acid position 31 is mutated to glutamic acid, amino acid position 65 is mutated to aspartic acid, amino acid position 108 is mutated to glycine, amino acid position 171 is mutated to valine, and amino acid position 194 is mutated to glutamic acid, and wherein the hKd and the cKd are between about 100 nM and about 120 nM.

In some embodiments, the single chain variable fragment CD3 binding protein does not bind to mouse CD3.

In one embodiment is provided a polynucleotide encoding a single chain variable fragment CD3 binding protein according to the present disclosure. In one embodiment is provided a vector comprising the polynucleotide described herein. In one embodiment is provided a host cell transformed with the vector described herein. In a further embodiment is provided a pharmaceutical composition comprising (i) a single chain variable fragment CD3 binding protein according to the present disclosure, the polynucleotide according to present disclosure, the vector according to present disclosure or the host cell according to present disclosure, and (ii) a pharmaceutically acceptable carrier.

In another embodiment is provided a process for the production of a single chain variable fragment CD3 binding protein according to the present disclosure, said process comprising culturing a host transformed or transfected with a vector comprising a nucleic acid sequence encoding single chain variable fragment CD3 binding protein according to the present disclosure under conditions allowing the expression of the single chain variable fragment CD3 binding protein and recovering and purifying the produced protein from the culture.

In another embodiment is provided a method for the treatment or amelioration of a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease comprising the administration of the single chain variable fragment CD3 binding protein according to the present disclosure, to a subject in need thereof. In some embodiments, the subject is human. In some embodiments, the method further comprises administration of an agent in combination with the single chain variable fragment CD3 binding protein according to the present disclosure.

Provided herein in one embodiment is a multispecific binding protein comprising the single chain variable fragment CD3 binding protein according the present disclosure. One embodiment describes an antibody comprising the single chain variable fragment CD3 binding protein according to the present disclosure. A further embodiment provides a multispecific antibody, a bispecific antibody, a single domain antibody, a variable heavy domain, a peptide, or a ligand, comprising the single chain variable fragment CD3 binding protein according to the present disclosure. Described herein in one embodiment is an antibody comprising the single chain variable fragment CD3 binding protein according to the present disclosure, wherein said antibody is a scFv antibody. Another embodiment describes a multispecific binding protein or antibody comprising the single chain variable fragment CD3 binding protein according to the present disclosure and a serum albumin binding domain.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

BRIEF DESCRIPTION OF THE DRAWINGS

FIG. 2 illustrates the amino acid sequence of the human CD3 binding protein (SEQ ID NO: 22). HC CDR1 is indicated in the first shaded sequence (GFTFNKYAMN (SEQ ID NO: 23)), HC CDR2 is indicated in the second shaded sequence (RIRSKYNNYATYYADSVK (SEQ ID NO: 24)), HC CDR3 is indicated in the third shaded sequence (HGNFGNSYISYWAY (SEQ ID NO: 25)), LC CDR1 is indicated in the fourth shaded sequence (GSSTGAVTSGNYPN (SEQ ID NO: 26)), LC CDR2 is indicated in the fifth shaded sequence (GTKFLAP (SEQ ID NO: 27)), and CDR3 is indicated in the sixth shaded sequence (VLWYSNRWV (SEQ ID NO: 28)).

FIG. 3 illustrates the profiles of the sixteen clones selected for more precise $K_d$ determinations.

FIG. 4 illustrates the temperature of hydrophobic exposure ($T_h°$ C.) for several anti-huCD3ε scFv variants.

DETAILED DESCRIPTION OF THE INVENTION

Figure 1:
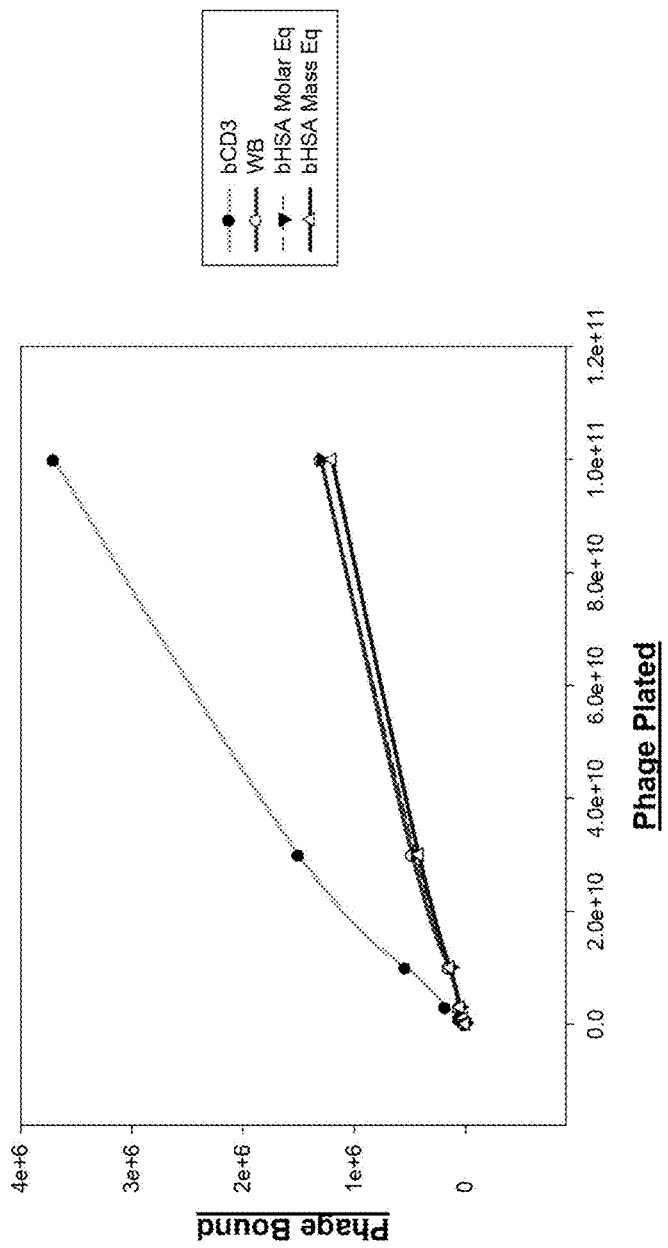
FIG. 1 illustrates phage titration on biotin-CD3ε and biotin-HSA.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby Certain Definitions The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the given value. Where particular values are described in the application and claims, unless otherwise stated the term "about" should be assumed to mean an acceptable error range for the particular value.

The terms "individual," "patient," or "subject" are used interchangeably. None of the terms require or are limited to situation characterized by the supervision (e.g. constant or intermittent) of a health care worker (e.g. a doctor, a registered nurse, a nurse practitioner, a physician's assistant, an orderly, or a hospice worker).

As used herein, "elimination half-time" is used in its ordinary sense, as is described in Goodman and Gillman's The Pharmaceutical Basis of Therapeutics 21-25 (Alfred Goodman Gilman, Louis S. Goodman, and Alfred Gilman, eds., 6th ed. 1980). Briefly, the term is meant to encompass a quantitative measure of the time course of drug elimination. The elimination of most drugs is exponential (i.e., follows first-order kinetics), since drug concentrations usually do not approach those required for saturation of the elimination process. The rate of an exponential process may be expressed by its rate constant, k, which expresses the fractional change per unit of time, or by its half-time, $t_{1/2}$ the time required for 50% completion of the process. The units of these two constants are time$^{-1}$ and time, respectively. A first-order rate constant and the half-time of the reaction are simply related ($k \times t_{1/2} = 0.693$) and may be interchanged accordingly. Since first-order elimination kinetics dictates that a constant fraction of drug is lost per unit time, a plot of the log of drug concentration versus time is linear at all times following the initial distribution phase (i.e. after drug absorption and distribution are complete). The half-time for drug elimination can be accurately determined from such a graph.

As used herein, the term "Percent (%) amino acid sequence identity" with respect to a sequence is defined as the percentage of amino acid residues in a candidate sequence that are identical with the amino acid residues in the specific sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

The term "Framework" or "FR" residues (or regions) refer to variable domain residues other than the CDR or hypervariable region residues as herein defined. A "human consensus framework" is a framework which represents the most commonly occurring amino acid residue in a selection of human immunoglobulin VL or VH framework sequences.

As used herein, "Variable region" or "variable domain" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the βsheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity. "Variable domain residue numbering as in Kabat" or "amino acid position numbering as in Kabat," and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence. It is not intended that CDRs of the present disclosure necessarily correspond to the Kabat numbering convention.

As used herein, the term "binding affinity" refers to the affinity of the proteins described in the disclosure to their binding targets, and is expressed numerically using "Kd" values. If two or more proteins are indicated to have comparable binding affinities towards their binding targets, then the Kd values for binding of the respective proteins towards their binding targets, are within +2-fold of each other. If two or more proteins are indicated to have comparable binding affinities towards single binding target, then the Kd values for binding of the respective proteins towards said single binding target, are within +2-fold of each other. If a protein is indicated to bind two or more targets with comparable binding affinities, then the Kd values for binding of said protein to the two or more targets are within +2-fold of each other. In general, a higher Kd value corresponds to a weaker binding. In some embodiments, the "Kd" is measured by a radiolabeled antigen binding assay (RIA) or surface plasmon resonance assays using a BIAcore™-2000 or a BIAcore™-3000 (BIAcore, Inc., Piscataway, N.J.). In certain embodiments, an "on-rate" or "rate of association" or "association rate" or "kon" and an "off-rate" or "rate of dissociation" or "dissociation rate" or "koff" are also determined with the surface plasmon resonance technique using a BIAcore™-2000 or a BIAcore™-3000 (BIAcore, Inc., Piscataway, N.J.). In additional embodiments, the "Kd", "kon", and "koff" are measured using the Octet® Systems (Pall Life Sciences).

Described herein are single chain variable fragment CD3 binding proteins, pharmaceutical compositions as well as nucleic acids, recombinant expression vectors, and host cells for making such single chain variable fragment CD3 binding proteins. Also provided are methods of using the disclosed single chain variable fragment CD3 binding proteins in the prevention, and/or treatment of diseases, conditions and disorders. In some embodiments, the single chain variable fragment CD3 binding proteins are capable of specifically binding to a CD 3 domain, as well as a target antigen and a half-life extension domain, such as a single domain binding antibody to human serum albumin (HSA).

CD3 Binding Domain

The specificity of the response of T cells is mediated by the recognition of antigen (displayed in context of a major histocompatibility complex, MHC) by the T cell receptor complex. As part of the T cell receptor complex, CD3 is a protein complex that includes a CD3γ (gamma) chain, a CD3δ (delta) chain, and two CD3ε (epsilon) chains which are present on the cell surface. CD3 associates with the a (alpha) and β (beta) chains of the T cell receptor (TCR) as well as and CD3 ζ (zeta) altogether to comprise the T cell receptor complex. Clustering of CD3 on T cells, such as by immobilized anti-CD3 antibodies leads to T cell activation similar to the engagement of the T cell receptor but independent of its clone-typical specificity.

In one aspect, the single chain variable fragment CD3 binding proteins described herein comprise a domain which specifically binds to CD3. In one aspect, the single chain variable fragment CD3 binding proteins described herein comprise a domain which specifically binds to human CD3. In one aspect, the single chain variable fragment CD3 binding proteins described herein comprise a domain which specifically binds to cynomolgus CD3. In one aspect, the single chain variable fragment CD3 binding proteins described herein comprise a domain which binds to human CD3 and cynomolgus CD3. In some embodiments, the single chain variable fragment CD3 binding proteins described herein comprise a domain which specifically binds to CD3γ. In some embodiments, the single chain variable fragment CD3 binding proteins described herein comprise a domain which specifically binds to CD3δ. In some embodiments, the single chain variable fragment CD3 binding proteins described herein comprise a domain which specifically binds to CD3ε.

In another aspect is provided a multispecific binding protein comprising a single chain variable fragment CD3 binding protein according to the present disclosure. In some embodiments, the multispecific protein comprising a single chain variable fragment CD3 binding protein according to the present disclosure specifically binds to the T cell receptor (TCR). In certain instances, the multispecific protein comprising a single chain variable fragment CD3 binding protein according to the present disclosure binds the α chain of the TCR. In certain instances, multispecific protein comprising a single chain variable fragment CD3 binding protein according to the present disclosure binds the β chain of the TCR.

In certain embodiments, the CD3 binding domain of the single chain variable fragment CD3 binding proteins described herein exhibit not only potent CD3 binding affinities with human CD3, but show also excellent crossreactivity with the respective cynomolgus monkey CD3 proteins. In some instances, the CD3 binding domain of the single chain variable fragment CD3 binding proteins are crossreactive with CD3 from cynomolgus monkey. In certain instances, the Kd for binding human CD3 (hKd) is about the same as the Kd for binding cynomolgus CD3 (cKd). In certain instances, the ratio between hKd and cKd (hKd:cKd) is between about 20:1 to about 1:2.

In some embodiments, the CD3 binding domain of the single chain variable fragment CD3 binding protein can be any domain that binds to CD3 including but not limited to domains from a monoclonal antibody, a polyclonal antibody, a recombinant antibody, a human antibody, a humanized antibody. In some instances, it is beneficial for the CD3 binding domain to be derived from the same species in which the single chain variable fragment CD3 binding protein will ultimately be used. For example, for use in humans, it may be beneficial for the CD3 binding domain of the single chain variable fragment CD3 binding protein to comprise human or humanized residues from the antigen binding domain of an antibody or antibody fragment.

Thus, in one aspect, the antigen-binding domain comprises a humanized or human antibody or an antibody fragment, or a murine antibody or antibody fragment. In one embodiment, the humanized or human anti-CD3 binding domain comprises one or more (e.g., all three) light chain complementary determining region 1 (LC CDR1), light chain complementary determining region 2 (LC CDR2), and light chain complementary determining region 3 (LC CDR3) of a humanized or human anti-CD3 binding domain described herein, and/or one or more (e.g., all three) heavy chain complementary determining region 1 (HC CDR1), heavy chain complementary determining region 2 (CDR2), and heavy chain complementary determining region 3 (CDR3) of a humanized or human anti-CD3 binding domain described herein, e.g., a humanized or human anti-CD3 binding domain comprising one or more, e.g., all three, LC CDRs and one or more, e.g., all three, HC CDRs.

In some embodiments, the humanized or human anti-CD3 binding domain comprises a humanized or human light chain variable region specific to CD3 where the light chain variable region specific to CD3 comprises human or non-human light chain CDRs in a human light chain framework region. In certain instances, the light chain framework region is a λ (lambda) light chain framework. In other instances, the light chain framework region is a κ (kappa) light chain framework.

In some embodiments, the humanized or human anti-CD3 binding domain comprises a humanized or human heavy chain variable region specific to CD3 where the heavy chain variable region specific to CD3 comprises human or non-human heavy chain CDRs in a human heavy chain framework region.

In certain instances, the complementary determining regions of the heavy chain and/or the light chain are derived from known anti-CD3 antibodies, such as, for example, muromonab-CD3 (OKT3), otelixizumab (TRX4), teplizumab (MGA031), visilizumab (Nuvion), SP34, TR-66 or X35-3, VIT3, BMA030 (BW264/56), CLB-T3/3, CRIS7, YTH12.5, F111-409, CLB-T3.4.2, TR-66, WT32, SPv-T3b, 11D8, XIII-141, XIII-46, XIII-87, 12F6, T3/RW2-8C8, T3/RW2-4B6, OKT3D, M-T301, SMC2, F101.01, UCHT-1 and WT-31.

In one embodiment, the anti-CD3 binding domain is a single chain variable fragment (scFv) comprising a light chain and a heavy chain of an amino acid sequence provided herein. As used herein, "single chain variable fragment" or "scFv" refers to an antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single polypeptide chain, and wherein the scFv retains the specificity of the intact antibody from which it is derived. In an embodiment, the anti-CD3 binding domain comprises: a light chain variable region comprising an amino acid sequence having at least one, two or three modifications (e.g., substitutions) but not more than 30, 20 or 10 modifications (e.g., substitutions) of an amino acid sequence of a light chain variable region provided herein, or a sequence with 95-99% identity with an amino acid sequence provided herein; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided herein, or a sequence with 95-99% identity to an amino acid sequence provided herein. In one embodiment, the humanized or human anti-CD3 binding domain is a scFv, and a light chain variable region comprising an amino acid sequence described herein, is attached to a heavy chain variable region comprising an amino acid sequence described herein, via a scFv linker. The light chain variable region and heavy chain variable region of a scFv can be, e.g., in any of the following orientations: light chain variable region-scFv linker-heavy chain variable region or heavy chain variable region-scFv linker-light chain variable region.

In some instances, scFvs which bind to CD3 are prepared according to known methods. For example, scFv molecules can be produced by linking VH and VL regions together using flexible polypeptide linkers. The scFv molecules comprise a scFv linker (e.g., a Ser-Gly linker) with an optimized length and/or amino acid composition. Accordingly, in some embodiments, the length of the scFv linker is such that the VH or VL domain can associate intermolecularly with the other variable domain to form the CD3 binding site. In certain embodiments, such scFv linkers are "short", i.e. consist of 0, 1, 2, 3, 4, 5, 6, 7, 8, 9, 10, 11 or 12 amino acid residues. Thus, in certain instances, the scFv linkers consist of about 12 or less amino acid residues. In the case of 0 amino acid residues, the scFv linker is a peptide bond. In some embodiments, these scFv linkers consist of about 3 to about 15, for example 8, 10 or 15 contiguous amino acid residues. Regarding the amino acid composition of the scFv linkers, peptides are selected that confer flexibility, do not interfere with the variable domains as well as allow interchain folding to bring the two variable domains together to form a functional CD3 binding site. For example, scFv linkers comprising glycine and serine residues generally provide protease resistance. In some embodiments, linkers in a scFv comprise glycine and serine residues. The amino acid sequence of the scFv linkers can be optimized, for example, by phage-display methods to improve the CD3 binding and production yield of the scFv. Examples of peptide scFv linkers suitable for linking a variable light chain domain and a variable heavy chain domain in a scFv include but are not limited to $(GS)_n$ (SEQ ID NO: 96), $(GGS)_n$ (SEQ ID NO: 97), $(GGGS)_n$ (SEQ ID NO: 98), $(GGSG)_n$ (SEQ ID NO: 99), $(GGSGG)_n$ (SEQ ID NO: 100), $(GGGGS)_n$ (SEQ ID NO: 101), $(GGGGG)_n$ (SEQ ID NO: 102), or $(GGG)_n$ (SEQ ID NO: 103), wherein n is 1, 2, 3, 4, 5, 6, 7, 8, 9, or 10. In one embodiment, the scFv linker can be $(GGGGS)_4$ (SEQ ID NO: 104) or $(GGGGS)_3$ (SEQ ID NO: 1). Variation in the linker length may retain or enhance activity, giving rise to superior efficacy in activity studies.

In some embodiments, CD3 binding domain of a single chain variable fragment CD3 binding protein has an affinity to CD3 on CD3 expressing cells with a $K_d$ of 1000 nM or less, 500 nM or less, 200 nM or less, 100 nM or less, 80 nM or less, 50 nM or less, 20 nM or less, 10 nM or less, 5 nM or less, 1 nM or less, or 0.5 nM or less. In some embodiments, the CD3 binding domain of a single chain variable fragment CD3 binding protein has an affinity to CD3ε, γ, or δ with a $K_d$ of 1000 nM or less, 500 nM or less, 200 nM or less, 100 nM or less, 80 nM or less, 50 nM or less, 20 nM or less, 10 nM or less, 5 nM or less, 1 nM or less, or 0.5 nM or less. In further embodiments, CD3 binding domain of a single chain variable fragment CD3 binding protein has low affinity to CD3, i.e., about 100 nM or greater.

In certain embodiments, the single chain variable fragment CD3 binding proteins described herein bind to human CD3 with a human Kd (hKd) and to cynomolgus CD3 with a cyno Kd (cKd). In some embodiments, hKd and cKd are between about between about 1 nM to about 2 nM, about 3 nM to about 5 nM, about 6 nM to about 10 nM, about 11 nM to about 20 nM, about 25 nM to about 40 nM, about 40 nM to about 60 nM, about 70 nM to about 90 nM, about 100 nM to about 120 nM, about 125 nM to about 140 nM, about 145 nM to about 160 nM, about 170 nM and to about 200 nM, about 210 nM to about 250 nM, about 260 nM to about 300 nM.

In some embodiments, the hKd and cKd of the single chain variable fragment CD3 binding proteins is about the same as the Kd of a CD3 binding protein having the sequence as set forth is SEQ ID NO. 22. In some embodiments, the hKd and cKd of the single chain variable fragment CD3 binding proteins is about 1.1 fold to about 1.5 fold the Kd of a CD3 binding protein having the sequence as set forth is SEQ ID NO. 22. In some embodiments, the hKd and cKd of the single chain variable fragment CD3 binding proteins is about 1.5 fold to about 2 fold the Kd of a CD3 binding protein having the sequence as set forth is SEQ ID NO. 22. In some embodiments, the hKd and cKd of the single chain variable fragment CD3 binding proteins is about 2.5 fold to about 3 fold the Kd of a CD3 binding protein having the sequence as set forth is SEQ ID NO. 22. In some embodiments, the hKd and cKd of the single chain variable fragment CD3 binding proteins is about 3 fold to about 5 fold the Kd of a CD3 binding protein having the sequence as set forth is SEQ ID NO. 22. In some embodiments, the hKd and cKd of the single chain variable fragment CD3 binding proteins is about 6 fold to about 15 fold the Kd of a CD3 binding protein having the sequence as set forth is SEQ ID NO. 22. In some embodiments, the hKd and cKd of the single chain variable fragment CD3 binding proteins is about 15 fold to about 20 fold the Kd of a CD3 binding protein having the sequence as set forth is SEQ ID NO. 22. In some embodiments, the hKd and cKd of the single chain variable fragment CD3 binding proteins is about 20 fold to about 50 fold the Kd of a CD3 binding protein having the sequence as set forth is SEQ ID NO. 22. In some embodiments, the hKd and cKd of the single chain variable fragment CD3 binding proteins is about 55 fold to about 70 fold the Kd of a CD3 binding protein having the sequence as set forth is SEQ ID NO. 22. In some embodiments, the hKd and cKd of the single chain variable fragment CD3 binding proteins is about 75 fold to about 100 fold the Kd of a CD3 binding protein having the sequence as set forth is SEQ ID NO. 22. In some embodiments, the hKd and cKd of the single chain variable fragment CD3 binding proteins is about 120 fold to about 200 fold the Kd of a CD3 binding protein having the sequence as set forth is SEQ ID NO. 22.

In some embodiments, the ratio between the hKd and cKd (hKd:cKd) ranges from about 20:1 to about 1:2. The affinity to bind to CD3 can be determined, for example, by the ability of the single chain variable fragment CD3 binding protein itself or its CD3 binding domain to bind to CD3 coated on an assay plate; displayed on a microbial cell surface; in solution; etc. The binding activity of the single chain variable fragment CD3 binding protein itself or its CD3 binding domain of the present disclosure to CD3 can be assayed by immobilizing the ligand (e.g., CD3) or the single chain variable fragment CD3 binding protein itself or its CD3 binding domain, to a bead, substrate, cell, etc. Agents can be added in an appropriate buffer and the binding partners incubated for a period of time at a given temperature. After washes to remove unbound material, the bound protein can be released with, for example, SDS, buffers with a high or low pH, and the like and analyzed, for example, by Surface Plasmon Resonance (SPR).

In some embodiments, the single chain variable fragment CD3 binding protein has an amino acid sequence selected from SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 94), and SEQ ID NO. 95.

In some embodiments, the single chain variable fragment CD3 binding protein has an amino acid sequence set forth as SEQ ID NO. 8, wherein the hKd is about 3.8 nM, and wherein the cKd is about 3.5 nM. In some embodiments, the single chain variable fragment CD3 binding protein has an amino acid sequence set forth as SEQ ID NO. 9, wherein the hKd is about 4.1 nM, and wherein the cKd is about 3.4 nM. In some embodiments, the single chain variable fragment CD3 binding protein has an amino acid sequence set forth as SEQ ID NO. 10, wherein the hKd is about 4.3 nM, and wherein the cKd is about 4.2 nM. In some embodiments, the single chain variable fragment CD3 binding protein has an amino acid sequence set forth as SEQ ID NO. 11, wherein the hKd is about 4.7 nM, and wherein the cKd is about 4.9 nM. In some embodiments, the single chain variable fragment CD3 binding protein has an amino acid sequence set forth as SEQ ID NO. 12, wherein the hKd is about 6.4 nM, and wherein the cKd is about 6.6 nM. In some embodiments, the single chain variable fragment CD3 binding protein has an amino acid sequence set forth as SEQ ID NO. 13, wherein the hKd is about 8 nM, and wherein the cKd is about 6.6 nM. In some embodiments, the single chain variable fragment CD3 binding protein has an amino acid sequence set forth as SEQ ID NO. 14, wherein the hKd is about 20 nM, and wherein the cKd is about 17 nM. In some embodiments, the single chain variable fragment CD3 binding protein has an amino acid sequence set forth as SEQ ID NO. 15, wherein the hKd is about 37 nM, and wherein the cKd is about 30 nM. In some embodiments, the single chain variable fragment CD3 binding protein has an amino acid sequence set forth as SEQ ID NO. 16, wherein the hKd is about 14 nM, and wherein the cKd is about 13 nM. In some embodiments, the single chain variable fragment CD3 binding protein has an amino acid sequence set forth as SEQ ID NO. 17, wherein the hKd is about 50 nM, and wherein the cKd is about 47 nM. In some embodiments, the single chain variable fragment CD3 binding protein has an amino acid sequence set forth as SEQ ID NO. 18, wherein the hKd is about 16 nM, and wherein the cKd is about 16 nM. In some embodiments, the single chain variable fragment CD3 binding protein has an amino acid sequence set forth as SEQ ID NO. 19, wherein the hKd is about 46 nM, and wherein the cKd is about 43 nM. In some embodiments, the single chain variable fragment CD3 binding protein has an amino acid sequence set forth as SEQ ID NO. 20, wherein the hKd is about 18 nM, and wherein the cKd is about 17 nM. In some embodiments, the single chain variable fragment CD3 binding protein has an amino acid sequence set forth as SEQ ID NO. 21, wherein the hKd is about 133 nM, and wherein the cKd is about 134 nM. In some embodiments, the single chain variable fragment CD3 binding protein has an amino acid sequence set forth as SEQ ID NO. 94, wherein the hKd is about 117 nM, and wherein the cKd is about 115 nM. In some embodiments, the single chain variable fragment CD3 binding protein has an amino acid sequence set forth as SEQ ID NO. 95, wherein the hKd is about 109 nM, and wherein the cKd is about 103 nM.

In some embodiments, the single chain variable fragment CD3 binding protein has an amino acid sequence set forth as SEQ ID NO. 8, wherein the hKd and cKd are about the same as the Kd towards CD3 of a protein which has the sequence as set forth in wt anti-CD3 (SEQ ID NO. 22). In some embodiments, the single chain variable fragment CD3 binding protein has an amino acid sequence set forth as SEQ ID NO. 9, wherein the hKd and cKd are about the same as the Kd towards CD3 of a protein which has the sequence as set forth in wt anti-CD3 (SEQ ID NO. 22). In some embodiments, the single chain variable fragment CD3 binding protein has an amino acid sequence set forth as SEQ ID NO. 10, wherein the hKd and cKd are about the same as the Kd towards CD3 of a protein which has the sequence as set forth in wt anti-CD3 (SEQ ID NO. 22). In some embodiments, the single chain variable fragment CD3 binding protein has an amino acid sequence set forth as SEQ ID NO. 11, wherein the hKd and cKd are about the same as the Kd towards CD3 of a protein which has the sequence as set forth in wt anti-CD3 (SEQ ID NO. 22). In some embodiments, the single chain variable fragment CD3 binding protein has an amino acid sequence set forth as SEQ ID NO. 12, wherein the hKd and cKd are about the same as the Kd towards CD3 of a protein which has the sequence as set forth in wt anti-CD3 (SEQ ID NO. 22). In some embodiments, the single chain variable fragment CD3 binding protein has an amino acid sequence set forth as SEQ ID NO. 13, wherein the hKd and cKd are about the same as the Kd towards CD3 of a protein which has the sequence as set forth in wt anti-CD3 (SEQ ID NO. 22). In some embodiments, the single chain variable fragment CD3 binding protein has an amino acid sequence set forth as SEQ ID NO. 14, wherein the hKd and cKd are about 3-fold to about 5-fold higher than the Kd towards CD3 of a protein which has the sequence as set forth in wt anti-CD3 (SEQ ID NO. 22). In some embodiments, the single chain variable fragment CD3 binding protein has an amino acid sequence set forth as SEQ ID NO. 15, wherein the hKd and cKd are about 3-fold to about 5-fold higher than the Kd towards CD3 of a protein which has the sequence as set forth in wt anti-CD3 (SEQ ID NO. 22). In some embodiments, the single chain variable fragment CD3 binding protein has an amino acid sequence set forth as SEQ ID NO. 16, wherein the hKd and cKd are about 3-fold to about 5-fold higher than the Kd towards CD3 of a protein which has the sequence as set forth in wt anti-CD3 (SEQ ID NO. 22). In some embodiments, the single chain variable fragment CD3 binding protein has an amino acid sequence set forth as SEQ ID NO. 17, wherein the hKd and cKd are about 6-fold to about 15-fold higher than the Kd towards CD3 of a protein which has the sequence as set forth in wt anti-CD3 (SEQ ID NO. 22). In some embodiments, the single chain variable fragment CD3 binding protein has an amino acid sequence set forth as SEQ ID NO. 18, wherein the hKd and cKd are about 3-fold to about 5-fold higher than the Kd towards CD3 of a protein which has the sequence as set forth in wt anti-CD3 (SEQ ID NO. 22). In some embodiments, the single chain variable fragment CD3 binding protein has an amino acid sequence set forth as SEQ ID NO. 19 (2A4), wherein the hKd and cKd are about 6-fold to about 15-fold higher than the Kd towards CD3 of a protein which has the sequence as set forth in wt anti-CD3 (SEQ ID NO. 22). In some embodiments, the single chain variable fragment CD3 binding protein has an amino acid sequence set forth as SEQ ID NO. 20, wherein the hKd and cKd are about 3-fold to about 5-fold higher than the Kd towards CD3 of a protein which has the sequence as set forth in wt anti-CD3 (SEQ ID NO. 22). In some embodiments, the single chain variable fragment CD3 binding protein has an amino acid sequence set forth as SEQ ID NO. 21, wherein the hKd and cKd are about 20-fold to about 50-fold higher than the Kd towards CD3 of a protein which has the sequence as set forth in wt anti-CD3 (SEQ ID NO. 22). In some embodiments, the single chain variable fragment CD3 binding protein has an amino acid sequence set forth as SEQ ID NO. 94, wherein the hKd and cKd are about 20-fold to about 50-fold higher than the Kd towards CD3 of a protein which has the sequence as set forth in wt anti-CD3 (SEQ ID NO. 22). In some embodiments, the single chain variable fragment CD3 binding protein has an amino acid sequence set forth as SEQ ID NO. 95, wherein the hKd and cKd are about 20-fold to about 50-fold higher than the Kd towards CD3 of a protein which has the sequence as set forth in wt anti-CD3 (SEQ ID NO. 22).

Half-Life Extension Domain

Human serum albumin (HSA) (molecular mass ~67 kDa) is the most abundant protein in plasma, present at about 50 mg/ml (600 µM), and has a half-life of around 20 days in humans. HSA serves to maintain plasma pH, contributes to colloidal blood pressure, functions as carrier of many metabolites and fatty acids, and serves as a major drug transport protein in plasma.

Noncovalent association with albumin extends the elimination half-time of short lived proteins. For example, a recombinant fusion of an albumin binding domain to a Fab fragment resulted in a decrease in in vivo clearance of 25- and 58-fold and a half-life extension of 26- and 37-fold when administered intravenously to mice and rabbits respectively as compared to the administration of the Fab fragment alone. In another example, when insulin is acylated with fatty acids to promote association with albumin, a protracted effect was observed when injected subcutaneously in rabbits or pigs. Together, these studies demonstrate a linkage between albumin binding and prolonged action.

In one aspect is provided a multispecific binding protein comprising a single chain variable fragment CD3 binding protein according to the present disclosure and further comprising a half-life extension domain, for example a domain which specifically binds to serum albumin. In some embodiments, the serum albumin binding domain of a single chain variable fragment CD3 binding protein can be any domain that binds to serum albumin including but not limited to domains from a monoclonal antibody, a polyclonal antibody, a recombinant antibody, a human antibody, a humanized antibody. In some embodiments, the serum albumin binding domain is a single chain variable fragments (scFv), single-domain antibody such as a heavy chain variable domain (VH), a light chain variable domain (VL) and a variable domain (VHH) of camelid derived sdAb, or antigen binding fragments of the HSA binding antibodies, such as Fab, Fab', F(ab)2, and Fv fragments, fragments comprised of one or more CDRs, single-chain antibodies (e.g., single chain Fv fragments (scFv)), disulfide stabilized (dsFv) Fv fragments, heteroconjugate antibodies (e.g., bispecific antibodies), pFv fragments, heavy chain monomers or dimers, light chain monomers or dimers, and dimers consisting of one heavy chain and one light chain, peptide, ligand or small molecule entity specific for serum albumin. In certain embodiments, the HSA binding domain is a single-domain antibody. In other embodiments, the serum albumin binding domain is a peptide. In further embodiments, the serum albumin binding domain is a small molecule. It is contemplated that the serum albumin binding domain of the multispecific binding protein comprising a single chain variable fragment CD3 binding protein is fairly small and no more than 25 kD, no more than 20 kD, no more than 15 kD, or no more than 10 kD in some embodiments. In certain instances, the serum albumin binding is 5 kD or less if it is a peptide or small molecule entity.

The half-life extension domain of a multispecific binding protein comprising a single chain variable fragment CD3 binding protein provides for altered pharmacodynamics and pharmacokinetics of the single chain variable fragment CD3 binding protein itself. As above, the half-life extension domain extends the elimination half-time. The half-life extension domain also alters pharmacodynamic properties including alteration of tissue distribution, penetration, and diffusion of the single chain variable fragment CD3 binding protein. In some embodiments, the half-life extension domain provides for improved tissue (including tumor) targeting, tissue distribution, tissue penetration, diffusion within the tissue, and enhanced efficacy as compared with a protein without a half-life extension domain. In one embodiment, therapeutic methods effectively and efficiently utilize a reduced amount of the multispecific binding protein comprising a single chain variable fragment CD3 binding protein, resulting in reduced side effects, such as reduced non-tumor cell cytotoxicity.

Further, the binding affinity of the half-life extension domain can be selected so as to target a specific elimination half-time in a particular multispecific binding protein comprising a single chain variable fragment CD3 binding protein. Thus, in some embodiments, the half-life extension domain has a high binding affinity. In other embodiments, the half-life extension domain has a medium binding affinity. In yet other embodiments, the half-life extension domain has a low or marginal binding affinity. Exemplary binding affinities include $K_d$ of 10 nM or less (high), between 10 nM and 100 nM (medium), and greater than 100 nM (low). As above, binding affinities to serum albumin are determined by known methods such as Surface Plasmon Resonance (SPR).

Target Antigen Binding Domain

In addition to the described CD3 and half-life extension domains, the multispecific binding proteins described herein in certain embodiments also comprise a domain that binds to a target antigen. A target antigen is involved in and/or associated with a disease, disorder or condition. In particular, a target antigen associated with a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease. In some embodiments, a target antigen is a tumor antigen expressed on a tumor cell. Alternatively in some embodiments, a target antigen is associated with a pathogen such as a virus or bacterium.

In some embodiments, a target antigen is a cell surface molecule such as a protein, lipid or polysaccharide. In some embodiments, a target antigen is a on a tumor cell, virally infected cell, bacterially infected cell, damaged red blood cell, arterial plaque cell, or fibrotic tissue cell.

The design of the multispecific binding protein comprising a single chain variable fragment CD3 binding protein described herein allows the binding domain to a target antigen to be flexible in that the binding domain to a target antigen can be any type of binding domain, including but not limited to, domains from a monoclonal antibody, a polyclonal antibody, a recombinant antibody, a human antibody, a humanized antibody. In some embodiments, the binding domain to a target antigen is a single chain variable fragments (scFv), single-domain antibody such as a heavy chain variable domain (VH), a light chain variable domain (VL) and a variable domain (VHH) of camelid derived sdAb. In other embodiments, the binding domain to a target antigen is a non-Ig binding domain, i.e., antibody mimetic, such as anticalins, affilins, affibody molecules, affimers, affitins, alphabodies, avimers, DARPins, fynomers, kunitz domain peptides, and monobodies. In further embodiments, the binding domain to a target antigen is a ligand or peptide that binds to or associates with a target antigen. In yet further embodiments, the binding domain to a target antigen is a knottin. In yet further embodiments, the binding domain to a target antigen is a small molecular entity.

Single Chain Variable Fragment CD3 Binding Protein Modifications

The single chain variable fragment CD3 binding proteins described herein encompass derivatives or analogs in which (i) an amino acid is substituted with an amino acid residue that is not one encoded by the genetic code, (ii) the mature polypeptide is fused with another compound such as polyethylene glycol, or (iii) additional amino acids are fused to the protein, such as a leader or secretory sequence or a sequence to block an immunogenic domain and/or for purification of the protein.

Typical modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Modifications are made anywhere in single chain variable fragment CD3 binding proteins described herein, including the peptide backbone, the amino acid side-chains, and the amino or carboxyl termini. Certain common peptide modifications that are useful for modification of single chain variable fragment CD3 binding proteins include glycosylation, lipid attachment, sulfation, gamma-carboxylation of glutamic acid residues, hydroxylation, blockage of the amino or carboxyl group in a polypeptide, or both, by a covalent modification, and ADP-ribosylation.

Polynucleotides Encoding Single Chain Variable Fragment CD3 Binding Proteins

Also provided, in some embodiments, are polynucleotide molecules encoding a single chain variable fragment CD3 binding protein or a multispecific binding protein comprising a single chain variable fragment CD3 binding protein according to the present disclosure. In some embodiments, the polynucleotide molecules are provided as a DNA construct. In other embodiments, the polynucleotide molecules are provided as a messenger RNA transcript.

The polynucleotide molecules are constructed by known methods such as by combining the genes encoding the three binding domains either separated by peptide linkers or, in other embodiments, directly linked by a peptide bond, into a single genetic construct operably linked to a suitable promoter, and optionally a suitable transcription terminator, and expressing it in bacteria or other appropriate expression system such as, for example CHO cells. In the embodiments where the target antigen binding domain is a small molecule, the polynucleotides contain genes encoding the CD3 binding domain and the half-life extension domain. In the embodiments where the half-life extension domain is a small molecule, the polynucleotides contain genes encoding the domains that bind to CD3 and the target antigen. Depending on the vector system and host utilized, any number of suitable transcription and translation elements, including constitutive and inducible promoters, may be used. The promoter is selected such that it drives the expression of the polynucleotide in the respective host cell.

In some embodiments, the polynucleotide is inserted into a vector, preferably an expression vector, which represents a further embodiment. This recombinant vector can be constructed according to known methods. Vectors of particular interest include plasmids, phagemids, phage derivatives, virii (e.g., retroviruses, adenoviruses, adeno-associated viruses, herpes viruses, lentiviruses, and the like), and cosmids.

A variety of expression vector/host systems may be utilized to contain and express the polynucleotide encoding the polypeptide of the described single chain variable fragment CD3 binding protein. Examples of expression vectors for expression in *E. coli* are pSKK (Le Gall et al., J Immunol Methods. (2004) 285(1): 111-27) or pcDNA5 (Invitrogen) for expression in mammalian cells, PICHIAPINK™ Yeast Expression Systems (Invitrogen), BACUVANCE™ Baculovirus Expression System (GenScript).

Thus, the single chain variable fragment CD3 binding proteins as described herein, in some embodiments, are produced by introducing a vector encoding the protein as described above into a host cell and culturing said host cell under conditions whereby the protein domains are expressed, may be isolated and, optionally, further purified.

Production of Single Chain Variable Fragment CD3 Binding Proteins

Disclosed herein, in some embodiments, is a process for the production of a single chain variable fragment CD3 binding protein. In some embodiments, the process comprises culturing a host transformed or transfected with a vector comprising a nucleic acid sequence encoding a single chain variable fragment CD3 binding protein under conditions allowing the expression of the single chain variable fragment CD3 binding protein and recovering and purifying the produced protein from the culture.

In additional embodiment is provided a process directed to improving one or more properties, e.g. affinity, stability, heat tolerance, cross-reactivity, etc., of the single chain variable fragment CD3 binding protein and/or the multispecific binding proteins comprising a single chain variable fragment CD3 binding protein as described herein, compared to a reference binding compound. In some embodiments, a plurality of single-substitution libraries is provided each corresponding to a different domain, or amino acid segment of the single chain variable fragment CD3 binding protein or reference binding compound such that each member of the single-substitution library encodes only a single amino acid change in its corresponding domain, or amino acid segment. (This allows all of the potential substitutions in a large protein or protein binding site to be probed with a few small libraries.) In some embodiments, the plurality of domains forms or covers a contiguous sequence of amino acids of the single chain variable fragment CD3 binding protein or a reference binding compound. Nucleotide sequences of different single-substitution libraries overlap with the nucleotide sequences of at least one other single-substitution library. In some embodiments, a plurality of single-substitution libraries are designed so that every member overlaps every member of each single-substitution library encoding an adjacent domain.

Binding compounds expressed from such single-substitution libraries are separately selected to obtain a subset of variants in each library which has properties at least as good as those of the reference binding compound and whose resultant library is reduced in size. (That is, the number of nucleic acids encoding the selected set of binding compounds is smaller than the number of nucleic acids encoding members of the original single-substitution library) Such properties include, but are not limited to, affinity to a target compound, stability with respect to various conditions such as heat, high or low pH, enzymatic degradation, cross-reactivity to other proteins and the like. The selected compounds from each single-substitution library are referred to herein interchangeably as "pre-candidate compounds," or "pre-candidate proteins." Nucleic acid sequences encoding the pre-candidate compounds from the separate single-substitution libraries are then shuffled in a PCR to generate a shuffled library, using PCR-based gene shuffling techniques.

An exemplary work flow of the screening process is described herein. Libraries of pre-candidate compounds are generated from single substitution libraries and selected for binding to the target protein(s), after which the pre-candidate libraries are shuffled to produce a library of nucleic acids encoding candidate compounds which, in turn, are cloned into a convenient expression vector, such as a phagemid expression system. Phage expressing candidate compounds then undergo one or more rounds of selection for improvements in desired properties, such as binding affinity to a target molecule. Target molecules may be adsorbed or otherwise attached to a surface of a well or other reaction container, or target molecules may be derivatized with a binding moiety, such as biotin, which after incubation with candidate binding compounds may be captured with a complementary moiety, such as streptavidin, bound to beads, such as magnetic beads, for washing. In exemplary selection regimens, the candidate binding compounds undergo a prolonged wash step so that only candidate compounds with very low dissociation rates from a target molecule are selected. Exemplary wash times for such embodiments are at least 8 hours; or in other embodiments, at least 24 hours; or in other embodiments, at least 48 hours; or in other embodiments, at least 72 hours. Isolated clones after selection are amplified and subjected to an additional cycle of selection or analyzed, for example by sequencing and by making comparative measurements of binding affinity, for example, by ELISA, surface plasmon resonance binding, bio-layer interferometry (e.g. Octet system, ForteBio, Menlo Park, Calif.) or the like.

In some embodiments, the process is implemented to identify one or more single chain variable fragment CD3 binding protein and/or a multispecific binding protein comprising a single chain variable fragment CD3 binding protein with improved thermal stability, improved cross reactivity to a selected set of binding targets compared to that of a reference CD3 binding protein, such as a protein having the amino acid sequence of SEQ ID NO. 22. Single substitution libraries are prepared by varying codons in the VH and VL regions of the reference CD3 binding protein, including both codons in framework regions and in CDRs; in another embodiment, the locations where codons are varied comprise the CDRs of the heavy and light chains of the reference CD3 binding protein, or a subset of such CDRs, such as solely CDR1, solely CDR2, solely CDR3, or pairs thereof. In another embodiment, locations where codons are varied occur solely in framework regions. In some embodiments, a library comprises single codon changes solely from a reference CD3 binding protein solely in framework regions of both VH and VL numbering in the range of from 10 to 250. In another embodiment, the locations where codons are varied comprise the CDR3s of the heavy and light chains of the reference CD3 binding protein, or a subset of such CDR3 s. In another embodiment, the number of locations where codons of VH and VL encoding regions are varied are in the range of from 10 to 250, such that up to 100 locations are in framework region. After preparation of the single substitution library, as outlined above, the following steps are carried out: (a) expressing separately each member of each single substitution library as a pre-candidate protein; (b) selecting members of each single substitution library which encode pre-candidate proteins which bind to a binding partner that differs from the original binding target [e.g. a desired cross-reaction target(s)]; (c) shuffling members of the selected libraries in a PCR to produce a combinatorial shuffled library; (d) expressing members of the shuffled library as candidate CD3 binding proteins; and (e) selecting members of the shuffled library one or more times for candidate CD3 binding proteins which bind the original binding partner and (f) further selecting the candidate proteins for binding to the desired cross-reactive target(s) thereby providing a nucleic acid encoded CD3 binding protein with increased cross reactivity for the one or more substances with respect to the reference CD3 binding protein without loss of affinity for the original ligand. In additional embodiments, the method may be implemented for obtaining a single chain variable fragment CD3 binding protein with decreased reactivity to a selected cross-reactive substance(s) or compound(s) or epitope(s) by substituting step (f) with the following step: depleting candidate binding compounds one or more times from the subset of candidate single chain variable fragment CD3 binding protein which bind to the undesired cross-reactive compound.

Pharmaceutical Compositions

Also provided, in some embodiments, are pharmaceutical compositions comprising a single chain variable fragment CD3 binding protein described herein, a vector comprising the polynucleotide encoding the polypeptide of the single chain variable fragment CD3 binding protein or a host cell transformed by this vector and at least one pharmaceutically acceptable carrier. The term "pharmaceutically acceptable carrier" includes, but is not limited to, any carrier that does not interfere with the effectiveness of the biological activity of the ingredients and that is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at a suitable dose. Preferably, the compositions are sterile. These compositions may also contain adjuvants such as preservative, emulsifying agents and dispersing agents. Prevention of the action of microorganisms may be ensured by the inclusion of various antibacterial and antifungal agents.

In some embodiments of the pharmaceutical compositions, the single chain variable fragment CD3 binding protein described herein is encapsulated in nanoparticles. In some embodiments, the nanoparticles are fullerenes, liquid crystals, liposome, quantum dots, superparamagnetic nanoparticles, dendrimers, or nanorods. In other embodiments of the pharmaceutical compositions, the single chain variable fragment CD3 binding protein is attached to liposomes. In some instances, the single chain variable fragment CD3 binding protein are conjugated to the surface of liposomes. In some instances, the single chain variable fragment CD3 binding protein are encapsulated within the shell of a liposome. In some instances, the liposome is a cationic liposome.

The single chain variable fragment CD3 binding proteins described herein are contemplated for use as a medicament. Administration is effected by different ways, e.g. by intravenous, intraperitoneal, subcutaneous, intramuscular, topical or intradermal administration. In some embodiments, the route of administration depends on the kind of therapy and the kind of compound contained in the pharmaceutical composition. The dosage regimen will be determined by the attending physician and other clinical factors. Dosages for any one patient depends on many factors, including the patient's size, body surface area, age, sex, the particular compound to be administered, time and route of administration, the kind of therapy, general health and other drugs being administered concurrently. An "effective dose" refers to amounts of the active ingredient that are sufficient to affect the course and the severity of the disease, leading to the reduction or remission of such pathology and may be determined using known methods.

Methods of Treatment

Also provided herein, in some embodiments, are methods and uses for stimulating the immune system of an individual in need thereof comprising administration of a single chain variable fragment CD3 binding protein described herein. In some instances, the administration of a single chain variable fragment CD3 binding protein described herein induces and/or sustains cytotoxicity towards a cell expressing a target antigen. In some instances, the cell expressing a target antigen is a cancer or tumor cell, a virally infected cell, a bacterially infected cell, an autoreactive T or B cell, damaged red blood cells, arterial plaques, or fibrotic tissue.

Also provided herein are methods and uses for a treatment of a disease, disorder or condition associated with a target antigen comprising administering to an individual in need thereof a single chain variable fragment CD3 binding protein described herein. Diseases, disorders or conditions associated with a target antigen include, but are not limited to, viral infection, bacterial infection, auto-immune disease, transplant rejection, atherosclerosis, or fibrosis. In other embodiments, the disease, disorder or condition associated with a target antigen is a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease. In one embodiment, the disease, disorder or condition associated with a target antigen is cancer. In one instance, the cancer is a hematological cancer. In another instance, the cancer is a solid tumor cancer.

As used herein, in some embodiments, "treatment" or "treating" or "treated" refers to therapeutic treatment wherein the object is to slow (lessen) an undesired physiological condition, disorder or disease, or to obtain beneficial or desired clinical results. For the purposes described herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. In other embodiments, "treatment" or "treating" or "treated" refers to prophylactic measures, wherein the object is to delay onset of or reduce severity of an undesired physiological condition, disorder or disease, such as, for example is a person who is predisposed to a disease (e.g., an individual who carries a genetic marker for a disease such as breast cancer).

In some embodiments of the methods described herein, the single chain variable fragment CD3 binding proteins are administered in combination with an agent for treatment of the particular disease, disorder or condition. Agents include but are not limited to, therapies involving antibodies, small molecules (e.g., chemotherapeutics), hormones (steroidal, peptide, and the like), radiotherapies (γ-rays, X-rays, and/or the directed delivery of radioisotopes, microwaves, UV radiation and the like), gene therapies (e.g., antisense, retroviral therapy and the like) and other immunotherapies. In some embodiments, the single chain variable fragment CD3 binding proteins are administered in combination with anti-diarrheal agents, anti-emetic agents, analgesics, opioids and/or non-steroidal anti-inflammatory agents. In some embodiments, the single chain variable fragment CD3 binding proteins are administered before, during, or after surgery.

EXAMPLES

Example 1: Identification of Anti-CD3 scFv Variants with Varying Affinities for Human CD3ε

Characterization of Parental Anti-CD3ε Phage

The parental anti-CD3ε showed good binding to biotin-CD3ε and low binding to biotin-HSA (FIG. 1).

Anti-CD3ε scFv Phage Libraries

A single substitution library was provided for the heavy chain CDR1, heavy chain CDR2, heavy chain CDR3, light chain CDR1, light chain CDR2, and light chain CDR3 domains. The amino acid residues varied in each domain are illustrated in the highlighted region in FIG. 2. Residues were varied one at a time via NNN mutagensis.

Selection of Clones and Determination of Binding Affinity

Single substitution libraries were bound to biotinylated hu-CD3ε, washed, eluted, and counted. Biotinylated cyno-CD3 was used as the round1 selection target, and washed for 4 hours after combinatorial phage binding from the two independent libraries (~2× selection). Biotinylated hu-CD3 was used as the round 2 selection target, and washed for 3 hours after binding of both libraries (<2× selection). PCRed inserts from the second round of selection were subcloned into the pcDNA3.4 His6 expression vector ("His6" disclosed as SEQ ID NO: 105). 180 clones were picked and DNA was purified, sequenced, and transfected into Expi293. A panel of sixteen clones with a range of affinities for human CD3ε were selected for more precise $K_d$ determination (FIG. 3).

Example 2: Cytotoxicity Assay

A bispecific antibody directed to CD20 and CD3, containing an anti-CD3 scFv variant identified in Example 1 is evaluated in vitro on its mediation of T cell dependent cytotoxicity to CD20$^+$ target cells.

Fluorescence labeled CD20$^+$ REC-1 cells (a Mantle cell lymphoma cell line, ATCC CRL-3004) are incubated with isolated PBMC of random donors or CB 15 T-cells (standardized T-cell line) as effector cells in the presence of the CD20-CD3 bispecific antibody containing an anti-CD3 scFv variant identified in Example 1. After incubation for 4 h at 37° C. in a humidified incubator, the release of the fluorescent dye from the target cells into the supernatant is determined in a spectrofluorimeter. Target cells incubated without the CD20-CD3 bispecific antibody containing an anti-CD3 scFv variant identified in Example 1 and target cells totally lysed by the addition of saponin at the end of the incubation serve as negative and positive controls, respectively.

Based on the measured remaining living target cells, the percentage of specific cell lysis is calculated according to the following formula: [1−(number of living targets$_{(sample)}$/ number of living targets$_{(spontaneous)}$)]×100%. Sigmoidal dose response curves and $EC_{50}$ values are calculated by non-linear regression/4-parameter logistic fit using the GraphPad Software. The lysis values obtained for a given variant concentration are used to calculate sigmoidal dose-response curves by 4 parameter logistic fit analysis using the Prism software.

Example 3: Thermal Stability of Anti-CD3 scFv Variants with Varying Affinities for Human CD3ε

The temperature of hydrophobic exposure ($T_h$) of a protein corresponds to the derivative of the inflection point of peak dye fluorescence and is known to correlate with melting temperature (Tm), which is a measure of protein stability. The goal of this study was to assess the $T_h$ for several anti-human CD3ε scFv variants.

Protein Production

Sequences of anti-human CD3ε scFv binding domains were cloned into pcDNA3.4 (Invitrogen) preceded by a leader sequence and followed by a 6× Histidine tag (SEQ ID NO: 105). Expi293F cells (Life Technologies A14527) were maintained in suspension in Optimum Growth Flasks (Thomson) between 0.2 to 8×1e6 cells/mL in Expi 293 media. Purified plasmid DNA was transfected into Expi293F cells in accordance with Expi293 Expression System Kit (Life Technologies, A14635) protocols, and maintained for 4-6 days post transfection. Conditioned media was partially purified by affinity and desalting chromatography. Anti-human CD3ε scFv proteins were concentrated with Amicon Ultra centrifugal filtration units (EMD Millipore), applied to Superdex 200 size exclusion media (GE Healthcare) and resolved in a neutral buffer containing excipients. Fraction pooling and final purity were assessed by SDS-PAGE and analytical SEC (size exclusion chromatography). The absorbance of purified protein solutions were determined at 280 nm using a SpectraMax M2 (Molecular Devices) and UV-transparent 96-well plates (Corning 3635) and their concentrations were calculated from molar extinction coefficients.

Differential Scanning Fluorimetry

Purified anti-human CD3ε scFv proteins were diluted to cocentrations ranging from 0.2 to 0.25 mg/mL together with 5×SYPRO orange dye (Life Technologies S6651) in 0.15% DMSO final concentration in a neutral buffer containing excipients into MicroAmp EnduraPlate optical microplates and adhesive film (Applied Biosystems 4483485 and 4311971). A plate containing diluted protein and dye mixtures was loaded into an ABI 7500 Fast real-time PCR instrument (Applied Biosytems) and subjected to a multi-step thermal gradient from 25° C. to 95° C. The thermal gradient comprised of a two minute hold at each one degree celsius step with excitation at 500 nm and emission collected with a ROX filter. $T_h$ in degrees celsius is presented, for several purified anti-human CD3ε scFv protein variants, in FIG. 4.

| SEQ ID NO: | Description | AA Sequence |
|---|---|---|
| 1 | Linker | GGGGSGGGGSGGGGS |
| 2 | HC CDR1 with valiant positions | G$X_1$$X_2$$X_3$N$X_4$Y$X_5$$X_6$N |
| 3 | HC CDR2 with variant positions | R I R S $X_7$ $X_8$ N $X_9$ Y $X_{10}$ T $X_{11}$ Y $X_{12}$ D $X_{13}$ V K |
| 4 | HC CDR3 with variant positions | H $X_{14}$ N F $X_{15}$ $X_{16}$ S $X_{17}$ I S Y W A $X_{18}$ |
| 5 | LC CDR1 with variant positions | $X_{19}$ $X_{20}$ $X_{21}$ $X_{22}$ G $X_{23}$ V $X_{24}$ $X_{25}$ G $X_{26}$ Y P N |
| 6 | LC CDR2 with variant positions | G $X_{27}$ $X_{28}$ $X_{29}$ $X_{30}$ $X_{31}$ P |
| 7 | LC CDR3 with variant positions | $X_{32}$ L W Y $X_{33}$ N $X_{34}$ W $X_{35}$ |
| 8 | Anti-CD3, clone 2B2 | EVQLVESGGGLVQPGGSLKLSCAASGFTFNKYAINWVRQAPGKGLEWVARIRSKYNNYATYYADQVKDRFTISRDDSKNTAYLQMNNLKTEDTAVYYCVRHANFGNSYISYWAYWGQGTLVTVSSGGGGSGGGGSGGGGSQTVVTQEPSLTVSPGGTVTLTCASSTGAVTSGNYPNWVQQKPGQAPRGLIGGTKFLVPGTPARFSGSLLGGKAALTLSGVQPEDEAEYYCTLWYSNRWVFGGGTKLTVL |
| 9 | Anti-CD3, clone 9F2 | EVQLVESGGGLVQPGGSLKLSCAASGFEFNKYAMNWVRQAPGKGLEWVARIRSKYNKYATYYADSVKDRFTISRDDSKNTAYLQMNNLKTEDTAVYYCVRHGNFGNSYISYWAYWGQGTLVTVSSGGGGSGGGGSGGGGSQTVVTQEPSLTVSPGGTVTLTCGSSFGAVTSGNYPNWVQQKPGQAPRGLIGGTKFLAPGTPARFSGSLLGGKAALTLSGVQPEDEAEYYCVLWYDNRWVFGGGTKLTVL |
| 10 | Anti-CD3, clone 5A2 | EVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSHISYWAYWGQGTLVTVSSGGGGSGGGGSGGGGSQTVVTQEPSLTVSPGGTVTLTCGSSTGYVTSGNYPNWVQQKPGQAPRGLIGGTSFLAPGTPARFSGSLLGGKAALTLSGVQPEDEAEYYCVLWYSNRWIFGGGTKLTVL |

| SEQ ID NO: | Description | AA Sequence |
|---|---|---|
| 11 | Anti-CD3, clone 6A2 | EVQLVESGGGLVQPGGSLKLSCAASGFMFNKYAMNWVRQAPGKG<br>LEWVARIRSKSNNYATYYADSVKDRFTISRDDSKNTAYLQMNNLK<br>TEDTAVYYCVRHGNFGNSYISYWATWGQGTLVTVSSGGGGSGGG<br>GSGGGGSQTVVTQEPSLTVSPGGTVTLTCGSSFGAVTSGNYPNWVQ<br>QKPGQAPRGLIGGTKLLAPGTPARFSGSLLGGKAALTLSGVQPEDE<br>AEYYCVLWYSNSWVFGGGTKLTVL |
| 12 | Anti-CD3, clone 2D2 | EVQLVESGGGLVQPGGSLKLSCAASGFTFNTYAMNWVRQAPGKGL<br>EWVARIRSKYNNYATYYKDSVKDRFTISRDDSKNTAYLQMNNLKT<br>EDTAVYYCVRHGNFGNSPISYWAYWGQGTLVTVSSGGGGSGGGG<br>SGGGGSQTVVTQEPSLTVSPGGTVTLTCGSSTGAVVSGNYPNWVQ<br>QKPGQAPRGLIGGTEFLAPGTPARFSGSLLGGKAALTLSGVQPEDE<br>AEYYCVLWYSNRWVFGGGTKLTVL |
| 13 | Anti-CD3, clone 3F2 | EVQLVESGGGLVQPGGSLKLSCAASGFTYNKYAMNWVRQAPGKG<br>LEWVARIRSKYNNYATYYADEVKDRFTISRDDSKNTAYLQMNNLK<br>TEDTAVYYCVRHGNFGNSPISYWAYWGQGTLVTVSSGGGGSGGG<br>GSGGGGSQTVVTQEPSLTVSPGGTVTLTCGSSKGAVTSGNYPNWV<br>QQKPGQAPRGLIGGTKELAPGTPARFSGSLLGGKAALTLSGVQPED<br>EAEYYCTLWYSNRWVFGGGTKLTVL |
| 14 | Anti-CD3, clone 1A2 | EVQLVESGGGLVQPGGSLKLSCAASGNTFNKYAMNWVRQAPGKG<br>LEWVARIRSKYNNYETYYADSVKDRFTISRDDSKNTAYLQMNNLK<br>TEDTAVYYCVRHTNFGNSYISYWAYWGQGTLVTVSSGGGGSGGG<br>GSGGGGSQTVVTQEPSLTVSPGGTVTLTCGSSTGAVTSGYYPNWVQ<br>QKPGQAPRGLIGGTYFLAPGTPARFSGSLLGGKAALTLSGVQPEDE<br>AEYYCVLWYSNRWVFGGGTKLTVL |
| 15 | Anti-CD3, clone 1C2 | EVQLVESGGGLVQPGGSLKLSCAASGFTFNNYAMNWVRQAPGKG<br>LEWVARIRSKYNNYATYYADAVKDRFTISRDDSKNTAYLQMNNLK<br>TEDTAVYYCVRHGNFGNSQISYWAYWGQGTLVTVSSGGGGSGGG<br>GSGGGGSQTVVTQEPSLTVSPGGTVTLTCGSSTGAVTDGNYPNWV<br>QQKPGQAPRGLIGGIKFLAPGTPARFSGSLLGGKAALTLSGVQPED<br>EAEYYCVLWYSNRWVFGGGTKLTVL |
| 16 | Anti-CD3, clone 2E4 | EVQLVESGGGLVQPGGSLKLSCAASGFTFNKYAVNWVRQAPGKGL<br>EWVARIRSKYNNYATYYADSVKDRFTISRDDSKNTAYLQMNNLKT<br>EDTAVYYCVRHGNFGNSYISYWAYWGQGTLVTVSSGGGGSGGGG<br>SGGGGSQTVVTQEPSLTVSPGGTVTLTCGESTGAVTSGNYPNWVQ<br>QKPGQAPRGLIGGTKILAPGTPARFSGSLLGGKAALTLSGVQPEDE<br>AEYYCVLWYSNRWVFGGGTKLTVL |
| 17 | Anti-CD3, clone 10E4 | EVQLVESGGGLVQPGGSLKLSCAASGFTFNKYPMNWVRQAPGKGL<br>EWVARIRSKYNNYATYYADSVKDRFTISRDDSKNTAYLQMNNLKN<br>EDTAVYYCVRHGNFNNSYISYWAYWGQGTLVTVSSGGGGSGGGG<br>SGGGGSQTVVTQEPSLTVSPGGTVTLTCGSSTGAVTKGNYPNWVQ<br>QKPGQAPRGLIGGTKMLAPGTPARFSGSLLGGKAALTLSGVQPEDE<br>AEYYCALWYSNRWVFGGGTKLTVL |
| 18 | Anti-CD3, clone 2H2 | EVQLVESGGGLVQPGGSLKLSCAASGFTFNGYAMNWVRQAPGKG<br>LEWVARIRSKYNNYATYYADEVKDRFTISRDDSKNTAYLQMNNLK<br>TEDTAVYYCVRHGNFGNSPISYWAYWGQGTLVTVSSGGGGSGGG<br>GSGGGGSQTVVTQEPSLTVSPGGTVTLTCGSSTGAVVSGNYPNWV<br>QQKPGQAPRGLIGGTEFLAPGTPARFSGSLLGGKAALTLSGVQPED<br>EAEYYCVLWYSNRWVFGGGTKLTVL |
| 19 | Anti-CD3, clone 2A4 | EVQLVESGGGLVQPGGSLKLSCAASGNTFNKYAMNWVRQAPGKG<br>LEWVARIRSKYNNYATYYADSVKDRFTISRDDSKNTAYLQMNNLK<br>TEDTAVYYCVRHGNFGDSYISYWAYWGQGTLVTVSSGGGGSGGG<br>GSGGGGSQTVVTQEPSLTVSPGGTVTLTCGSSTGAVTHGNYPNWV<br>QQKPGQAPRGLIGGTKVLAPGTPARFSGSLLGGKAALTLSGVQPED<br>EAEYYCVLWYSNRWVFGGGTKLTVL |
| 20 | Anti-CD3, clone 10B2 | EVQLVESGGGLVQPGGSLKLSCAASGFTFNNYAMNWVRQAPGKG<br>LEWVARIRSGYNNYATYYADSVKDRFTISRDDSKNTAYLQMNNLK<br>TEDTAVYYCVRHGNFGNSYISYWAYWGQGTLVTVSSGGGGSGGG<br>GSGGGGSQTVVTQEPSLTVSPGGTVTLTCGSYTGAVTSGNYPNWV<br>QQKPGQAPRGLIGGTKFNAPGTPARFSGSLLGGKAALTLSGVQPED<br>EAEYYCVLWYANRWVFGGGTKLTVL |
| 21 | Anti-CD3, clone 1G4 | EVQLVESGGGLVQPGGSLKLSCAASGFEFNKYAMNWVRQAPGKG<br>LEWVARIRSKYNNYETYYADSVKDRFTISRDDSKNTAYLQMNNLK<br>TEDTAVYYCVRHGNFGNSLISYWAYWGQGTLVTVSSGGGGSGGG |

| SEQ ID NO: | Description | AA Sequence |
|---|---|---|
|  |  | GSGGGGSQTVVTQEPSLTVSPGGTVTLTCGSSSGAVTSGNYPNWVQ QKPGQAPRGLIGGTKFGAPGTPARFSGSLLGGKAALTLSGVQPEDE AEYYCVLWYSNRWVFGGGTKLTVL |
| 22 | wt anti-CD3 | EVQLVESGGGLVQPGGSLKLSCAASGFTFNKYAMNWVRQAPGKG LEWVARIRSKYNNYATYYADSVKDRFTISRDDSKNTAYLQMNNLK TEDTAVYYCVRHGNFGNSYISYWAYWGQGTLVTVSSGGGGSGGG GSGGGGSQTVVTQEPSLTVSPGGTVTLTCGSSTGAVTSGNYPNWVQ QKPGQAPRGLIGGTKFLAPGTPARFSGSLLGGKAALTLSGVQPEDE AEYYCVLWYSNRWVFGGGTKLTVL |
| 23 | wt anti-CD3 HC CDR1 | GFTFNKYAMN |
| 24 | wt anti-CD3 HC CDR2 | RIRSKYNNYATYYADSVK |
| 25 | wt anti-CD3 HC CDR3 | HGNFGNSYISYWAY |
| 26 | wt anti-CD3 LC CDR1 | GSSTGAVTSGNYPN |
| 27 | wt anti-CD3 LC CDR2 | GTKFLAP |
| 28 | wt anti-CD3 LC CDR3 | VLWYSNRWV |
| 29 | HC CDR1 variant 1 | GNTFNKYAMN |
| 30 | HC CDR1 variant 2 | GFEFNKYAMN |
| 31 | HC CDR1 variant 3 | GFMFNKYAMN |
| 32 | HC CDR1 variant 4 | GFTYNKYAMN |
| 33 | HC CDR1 variant 5 | GFTFNNYAMN |
| 34 | HC CDR1 variant 6 | GFTFNGYAMN |
| 35 | HC CDR1 variant 7 | GFTFNTYAMN |
| 36 | HC CDR1 variant 8 | GFTFNEYAMN |
| 37 | HC CDR1 variant 9 | GFTFNKYPMN |
| 38 | HC CDR1 variant 10 | GFTFNKYAVN |
| 39 | HC CDR1 variant 11 | GFTFNKYAIN |
| 40 | HC CDR1 variant 12 | GFTFNKYALN |
| 41 | HC CDR2 variant 1 | RIRSGYNNYATYYADSVK |
| 42 | HC CDR2 variant 2 | RIRSKSNNYATYYADSVK |
| 43 | HC CDR2 variant 3 | RIRSKYNKYATYYADSVK |
| 44 | HC CDR2 variant 4 | RIRSKYNNYETYYADSVK |
| 45 | HC CDR2 variant 5 | RIRSKYNNYATEYADSVK |
| 46 | HC CDR2 variant 6 | RIRSKYNNYATYYKDSVK |
| 47 | HC CDR2 variant 7 | RIRSKYNNYATYYADEVK |
| 48 | HC CDR2 variant 8 | RIRSKYNNYATYYADAVK |
| 49 | HC CDR2 variant 9 | RIRSKYNNYATYYADQVK |
| 50 | HC CDR2 variant 10 | RIRSKYNNYATYYADDVK |
| 51 | HC CDR3 variant 1 | HANFGNSYISYWAY |
| 52 | HC CDR3 variant 2 | HTNFGNSYISYWAY |
| 53 | HC CDR3 variant 3 | HGNFNNSYISYWAY |
| 54 | HC CDR3 variant 4 | HGNFGDSYISYWAY |
| 55 | HC CDR3 variant 5 | HGNFGNSHISYWAY |

| SEQ ID NO: | Description | AA Sequence |
|---|---|---|
| 56 | HC CDR3 variant 6 | HGNFGNSPISYWAY |
| 57 | HC CDR3 variant 7 | HGNFGNSQISYWAY |
| 58 | HC CDR3 variant 8 | HGNFGNSLISYWAY |
| 59 | HC CDR3 variant 9 | HGNFGNSGISYWAY |
| 60 | HC CDR3 variant 10 | HGNFGNSYISYWAT |
| 61 | LC CDR1 variant 1 | ASSTGAVTSGNYPN |
| 62 | LC CDR1 variant 2 | GESTGAVTSGNYPN |
| 63 | LC CDR1 variant 3 | GSYTGAVTSGNYPN |
| 64 | LC CDR1 variant 4 | GSSFGAVTSGNYPN |
| 65 | LC CDR1 variant 5 | GSSKGAVTSGNYPN |
| 66 | LC CDR1 variant 6 | GSSSGAVTSGNYPN |
| 67 | LC CDR1 variant 7 | GSSTGYVTSGNYPN |
| 68 | LC CDR1 variant 8 | GSSTGAVVSGNYPN |
| 69 | LC CDR1 variant 9 | GSSTGAVTDGNYPN |
| 70 | LC CDR1 variant 10 | GSSTGAVTKGNYPN |
| 71 | LC CDR1 variant 11 | GSSTGAVTHGNYPN |
| 72 | LC CDR1 variant 12 | GSSTGAVTVGNYPN |
| 73 | LC CDR1 variant 13 | GSSTGAVTSGYYPN |
| 74 | LC CDR2 variant 1 | GIKFLAP |
| 75 | LC CDR2 variant 2 | GTEFLAP |
| 76 | LC CDR2 variant 3 | GTYFLAP |
| 77 | LC CDR2 variant 4 | GTSFLAP |
| 78 | LC CDR2 variant 5 | GTNFLAP |
| 79 | LC CDR2 variant 6 | GTKLLAP |
| 80 | LC CDR2 variant 7 | GTKELAP |
| 81 | LC CDR2 variant 8 | GTKILAP |
| 82 | LC CDR2 variant 9 | GTKMLAP |
| 83 | LC CDR2 variant 10 | GTKVLAP |
| 84 | LC CDR2 variant 11 | GTKFNAP |
| 85 | LC CDR2 variant 12 | GTKFGAP |
| 86 | LC CDR2 variant 13 | GTKFLVP |
| 87 | LC CDR3 variant 1 | TLWYSNRWV |
| 88 | LC CDR3 variant 2 | ALWYSNRWV |
| 89 | LC CDR3 variant 3 | VLWYDNRWV |
| 90 | LC CDR3 variant 4 | VLWYANRWV |
| 91 | LC CDR3 variant 5 | VLWYSNSWV |
| 92 | LC CDR3 variant 6 | VLWYSNRWI |
| 93 | LC CDR3 variant 7 | VLWYSNRWA |

| SEQ ID NO: | Description | AA Sequence |
|---|---|---|
| 94 | Anti-CD3, clone 2G5 | EVQLVESGGGLVQPGGSLKLSCAASGFTFNKYALNWVRQAPGKGL EWVARIRSKYNNYATEYADSVKDRFTISRDDSKNTAYLQMNNLKT EDTAVYYCVRHGNFGNSPISYWAYWGQGTLVTVSSGGGGSGGGG SGGGGSQTVVTQEPSLTVSPGGTVTLTCGSSTGAVTSGNYPNWVQQ KPGQAPRGLIGGTNFLAPGTPERFSGSLLGGKAALTLSGVQPEDEA EYYCVLWYSNRWAFGGGTKLTVL |
| 95 | Anti-CD3, clone 8A5 | EVQLVESGGGLVQPGGSLKLSCAASGFTFNEYAMNWVRQAPGKGL EWVARIRSKYNNYATYYADDVKDRFTISRDDSKNTAYLQMNNLKT EDTAVYYCVRHGNFGNSGISYWAYWGQGTLVTVSSGGGGSGGGG SGGGGSQTVVTQEPSLTVSPGGTVTLTCGSSTGAVTVGNYPNWVQ QKPGQAPRGLIGGTEFLAPGTPARFSGSLLGGKAALTLSGVQPEDE AEYYCVLWYSNRWVFGGGTKLTVL |
| 96 | Exemplary linker sequence(GS)n | |
| 97 | Exemplary linker sequence(GGS)n | |
| 98 | Exemplary linker sequence(GGGS)n | |
| 99 | Exemplary linker sequence(GGSG)n | |
| 100 | Exemplary linker sequence(GGSGG)n | |
| 101 | Exemplary linker sequence(GGGGS)n | |
| 102 | Exemplary linker sequence(GGGGG)n | |
| 103 | Exemplary linker sequence(GGG)n | |
| 104 | Exemplary linker sequence(GGGGS)4 | |
| 105 | 6X Histidine | HHHHHH |

What is claimed is:

1. A method of treating a cancer, the method comprising administering to a subject a protein, wherein the protein comprises a single chain variable fragment CD3 binding protein comprising a variable heavy chain region (VH), a variable light chain region (VL), and a linker, wherein the protein further comprises a cancer antigen binding domain, wherein the VH comprises complementarity determining regions HC CDR1, HC CDR2, and HC CDR3, wherein the VL comprises complementarity determining regions LC CDR1, LC CDR2, and LC CDR3, wherein the single chain variable fragment CD3 binding protein is at least eighty percent identical to SEQ ID NO: 22, wherein
   (a) the amino acid sequence of HC CDR1 is as set forth in SEQ ID NO. 29, SEQ ID NO. 30, SEQ ID NO. 31, SEQ ID NO. 32, SEQ ID NO. 33, SEQ ID NO. 34, SEQ ID NO. 35, SEQ ID NO. 36, SEQ ID NO. 37, SEQ ID NO. 38, SEQ ID NO. 39, or SEQ ID NO. 40;
   (b) the amino acid sequence of HC CDR2 is as set forth in SEQ ID NO. 41, SEQ ID NO. 42, SEQ ID NO. 43, SEQ ID NO. 44, SEQ ID NO. 45, SEQ ID NO. 46, SEQ ID NO. 47, SEQ ID NO. 48, SEQ ID NO. 49, or SEQ ID NO. 50;
   (c) the amino acid sequence of HC CDR3 is as set forth in SEQ ID NO. 51, SEQ ID NO. 52, SEQ ID NO. 53, SEQ ID NO. 54, SEQ ID NO. 55, SEQ ID NO. 56, SEQ ID NO. 57, SEQ ID NO. 58, SEQ ID NO. 59, or SEQ ID NO. 60;
   (d) the amino acid sequence of LC CDR1 is as set forth in SEQ ID NO. 61, SEQ ID NO. 62, SEQ ID NO. 63, SEQ ID NO. 64, SEQ ID NO. 65, SEQ ID NO. 66, SEQ ID NO. 67, SEQ ID NO. 68, SEQ ID NO. 69, SEQ ID NO. 70, SEQ ID NO. 71, SEQ ID NO. 72, or SEQ ID NO: 73;
   (e) the amino acid sequence of LC CDR2 is as set forth in SEQ ID NO. 74, SEQ ID NO. 75, SEQ ID NO. 76, SEQ ID NO. 77, SEQ ID NO. 78, SEQ ID NO. 79, SEQ ID NO. 80, SEQ ID NO. 81, SEQ ID NO. 82, SEQ ID NO. 83, SEQ ID NO. 84, SEQ ID NO. 85, or SEQ ID NO. 86; and
   (f) the amino acid sequence of LC CDR3 is as set forth in SEQ ID NO. 87, SEQ ID NO: 88, SEQ ID NO. 89, SEQ ID NO. 90, SEQ ID NO. 91, SEQ ID NO. 92, or SEQ ID NO. 93, and wherein said single chain variable fragment CD3 binding protein has an amino acid sequence that is at least 95% identical to a sequence selected from the group consisting of: SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 94, and SEQ ID NO. 95.

2. The method of claim 1, wherein HC CDR1 is SEQ ID NO. 39, HC CDR2 is SEQ ID NO. 49, HC CDR3 is SEQ ID NO. 51, LC CDR1 is SEQ ID NO. 61, LC CDR2 is SEQ ID NO. 86, and LC CDR3 is SEQ ID NO. 87.

3. The method of claim 1, wherein HC CDR1 is SEQ ID NO. 30, HC CDR2 is SEQ ID NO. 43, LC CDR1 is SEQ ID NO. 64, and LC CDR3 is SEQ ID NO. 89.

4. The method of claim 1, wherein HC CDR3 is SEQ ID NO. 55, LC CDR1 is SEQ ID NO. 67, LC CDR2 is SEQ ID NO. 77, and LC CDR3 is SEQ ID NO. 92.

5. The method of claim 1, wherein HC CDR1 is SEQ ID NO. 31, HC CDR2 is SEQ ID NO. 42, HC CDR3 is SEQ ID NO. 60, LC CDR1 is SEQ ID NO. 64, LC CDR2 is SEQ ID NO. 79, and LC CDR3 is SEQ ID NO. 91.

6. The method of claim 1, wherein HC CDR1 is SEQ ID NO. 35, HC CDR2 is SEQ ID NO. 46, HC CDR3 is SEQ ID NO. 56, LC CDR1 is SEQ ID NO. 68, and LC CDR3 is SEQ ID NO. 75.

7. The method of claim 1, wherein HC CDR1 is SEQ ID NO. 29, HC CDR2 is SEQ ID NO. 44, HC CDR3 is SEQ ID NO. 52, LC CDR1 is SEQ ID NO. 73, and LC CDR2 is SEQ ID NO. 76.

8. The method of claim 1, wherein HC CDR1 is SEQ ID NO. 33, HC CDR2 is SEQ ID NO. 48, HC CDR3 is SEQ ID NO. 57, LC CDR1 is SEQ ID NO. 69, and LC CDR2 is SEQ ID NO. 74.

9. The method of claim 1, wherein HC CDR1 is SEQ ID NO. 37, HC CDR3 is SEQ ID NO. 53, LC CDR1 is SEQ ID NO. 70, LC CDR2 is SEQ ID NO. 82, and LC CDR3 is SEQ ID NO. 88.

10. The method of claim 1, wherein HC CDR1 is SEQ ID NO. 34, HC CDR2 is SEQ ID NO. 47, HC CDR3 is SEQ ID NO. 56, LC CDR1 is SEQ ID NO. 68 and LC CDR2 is SEQ ID NO. 75.

11. The method of claim 1, wherein HC CDR1 is SEQ ID NO. 29, HC CDR3 is SEQ ID NO. 54, LC CDR1 is SEQ ID NO. 71 and LC CDR2 is SEQ ID NO. 83.

12. The method of claim 1, wherein HC CDR1 is SEQ ID NO. 33, HC CDR2 is SEQ ID NO. 41, LC CDR1 is SEQ ID NO. 63, LC CDR2 is SEQ ID NO. 84, and LC CDR1 is SEQ ID NO. 90 or wherein HC CDR1 is SEQ ID NO. 30, HC CDR2 is SEQ ID NO. 44, HC CDR3 is SEQ ID NO. 58, LC CDR1 is SEQ ID NO. 66 and LC CDR2 is SEQ ID NO. 85.

13. The method of claim 1, wherein HC CDR1 is SEQ ID NO. 40, HC CDR2 is SEQ ID NO. 45, HC CDR3 is SEQ ID NO. 56, LC CDR2 is SEQ ID NO. 78 and LC CDR3 is SEQ ID NO. 93 or wherein HC CDR1 is SEQ ID NO. 36, HC CDR2 is SEQ ID NO. 50, HC CDR3 is SEQ ID NO. 59, LC CDR1 is SEQ ID NO. 72 and LC CDR2 is SEQ ID NO. 75.

14. The method of claim 1, wherein the single chain variable fragment CD3 binding protein comprises a sequence that is at least 80% identical to SEQ ID NO. 22.

15. The method of claim 1, wherein the single chain variable fragment CD3 binding protein comprises a sequence selected from the group consisting of SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 94, and SEQ ID NO. 95.

16. The method of claim 15, wherein the single chain variable fragment CD3 binding protein comprises the sequence of SEQ ID No. 8.

17. The method of claim 1, wherein the linker has a sequence selected from those of SEQ ID NO. 1 and SEQ ID NO. 96-104.

18. The method of claim 1, wherein the cancer comprises a hematological cancer.

19. The method of claim 1, wherein the cancer comprises a solid tumor cancer.

20. A method of treating a cancer, the method comprising administering a protein,
    wherein the protein comprises a single chain variable fragment CD3 binding protein comprising a variable heavy chain region (VH) and a variable light chain region (VL),
    wherein the VH comprises complementarity determining regions HC CDR1, HC CDR2, and HC CDR3,
    wherein the VL comprises complementarity determining regions LC CDR1, LC CDR2, and LC CDR3,
    wherein the HC-CDR1, the HC-CDR2, the HC-CDR3, the LC-CDR1, the LC-CDR1, and the LC-CDR3 are not simultaneously SEQ ID NO. 23, SEQ ID NO. 24, SEQ ID NO. 25, SEQ ID NO. 26, SEQ ID NO. 27, and SEQ ID NO. 28,
    wherein the single chain variable fragment CD3 binding protein is at least 80% identical to SEQ ID NO. 22,
    wherein the protein further comprises a cancer antigen binding domain, and
    wherein the CD3 binding CDRs are selected from:
    (i) HC CDR1 is SEQ ID NO. 39, HC CDR2 is SEQ ID NO. 49, HC CDR3 is SEQ ID NO. 51, LC CDR1 is SEQ ID NO. 61, LC CDR2 is SEQ ID NO. 86, and LC CDR3 is SEQ ID NO. 87;
    (ii) HC CDR1 is SEQ ID NO. 30, HC CDR2 is SEQ ID NO. 43, HC CDR3 is SEQ ID NO. 25, LC CDR1 is SEQ ID NO. 64, LC CDR2 is SEQ ID NO. 27, and LC CDR3 is SEQ ID NO. 89;
    (iii) HC CDR1 is SEQ ID NO. 23, HC CDR2 is SEQ ID NO. 24, HC CDR3 is SEQ ID NO. 55, LC CDR1 is SEQ ID NO. 67, LC CDR2 is SEQ ID NO. 77, and LC CDR3 is SEQ ID NO. 92;
    (iv) HC CDR1 is SEQ ID NO. 31, HC CDR2 is SEQ ID NO. 42, HC CDR3 is SEQ ID NO. 60, LC CDR1 is SEQ ID NO. 64, LC CDR2 is SEQ ID NO. 79, and LC CDR3 is SEQ ID NO. 91;
    (v) HC CDR1 is SEQ ID NO. 35, HC CDR2 is SEQ ID NO. 46, HC CDR3 is SEQ ID NO. 56, LC CDR1 is SEQ ID NO. 68, LC CDR2 is SEQ ID NO. 75, and LC CDR3 is SEQ ID NO. 28;
    (vi) HC CDR1 is SEQ ID NO. 32, HC CDR2 is SEQ ID NO. 47, HC CDR3 is SEQ ID NO. 56, LC CDR1 is SEQ ID NO. 65, LC CDR2 is SEQ ID NO. 80, and LC CDR3 is SEQ ID NO. 87;
    (vii) HC CDR1 is SEQ ID NO. 29, HC CDR2 is SEQ ID NO. 44, HC CDR3 is SEQ ID NO. 52, LC CDR1 is SEQ ID NO. 73, LC CDR2 is SEQ ID NO. 76, and LC CDR3 is SEQ ID NO. 28;
    (viii) HC CDR1 is SEQ ID NO. 33, HC CDR2 is SEQ ID NO. 48, HC CDR3 is SEQ ID NO. 57, LC CDR1 is SEQ ID NO. 69, LC CDR2 is SEQ ID NO. 74, and LC CDR3 is SEQ ID NO. 28;
    (ix) HC CDR1 is SEQ ID NO. 38, HC CDR2 is SEQ ID NO. 24, HC CDR3 is SEQ ID NO. 25, LC CDR1 is SEQ ID NO. 62, LC CDR2 is SEQ ID NO. 81, and LC CDR3 is SEQ ID NO. 28;
    (x) HC CDR1 is SEQ ID NO. 37, HC CDR2 is SEQ ID NO. 24, HC CDR3 is SEQ ID NO. 53, LC CDR1 is SEQ ID NO. 70, LC CDR2 is SEQ ID NO. 82, and LC CDR3 is SEQ ID NO. 88;
    (xi) HC CDR1 is SEQ ID NO. 34, HC CDR2 is SEQ ID NO. 47, HC CDR3 is SEQ ID NO. 56, LC CDR1 is SEQ ID NO. 68, LC CDR2 is SEQ ID NO. 75, and LC CDR3 is SEQ ID NO. 28;
    (xii) HC CDR1 is SEQ ID NO. 29, HC CDR2 is SEQ ID NO. 24, HC CDR3 is SEQ ID NO. 54, LC CDR1 is SEQ ID NO. 71, LC CDR2 is SEQ ID NO. 83, and LC CDR3 is SEQ ID NO. 28;
    (xiii) HC CDR1 is SEQ ID NO. 33, HC CDR2 is SEQ ID NO. 41, HC CDR3 is SEQ ID NO. 25, LC CDR1 is SEQ ID NO. 63, LC CDR2 is SEQ ID NO. 84, and LC CDR3 is SEQ ID NO. 90;
    (xiv) HC CDR1 is SEQ ID NO. 30, HC CDR2 is SEQ ID NO. 44, HC CDR3 is SEQ ID NO. 58, LC CDR1 is SEQ ID NO. 66, LC CDR2 is SEQ ID NO. 85, and LC CDR3 is SEQ ID NO. 28;
    (xv) HC CDR1 is SEQ ID NO. 94, HC CDR2 is SEQ ID NO. 45, HC CDR3 is SEQ ID NO. 56, LC CDR1 is SEQ ID NO. 26, LC CDR2 is SEQ ID NO. 78, and LC CDR3 is SEQ ID NO. 93; or
    (xvi) HC CDR1 is SEQ ID NO. 36, HC CDR2 is SEQ ID NO. 50, HC CDR3 is SEQ ID NO. 59, LC CDR1 is SEQ ID NO. 72, LC CDR2 is SEQ ID NO. 75, and LC CDR3 is SEQ ID NO. 28.

21. The method of claim 20, wherein the single chain variable fragment CD3 binding protein comprises a sequence that is at least 80% identical to a sequence selected from the group consisting of SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 94, and SEQ ID NO. 95.

22. The method of claim 20, wherein the cancer comprises a hematological cancer.

23. The method of claim 20, wherein the cancer comprises a solid tumor cancer.

24. A method of treating a cancer comprising administering a multispecific protein comprising: (a) a single chain variable fragment CD3 binding protein, (b) a domain that specifically binds to a serum albumin, and (c) a cancer antigen binding domain, wherein the CD3 binding protein comprising a variable heavy chain region (VH), a variable light chain region (VL), wherein VH comprises complementarity determining regions HC CDR1, HC CDR2, and HC CDR3, wherein VL comprises complementarity determining regions LC CDR1, LC CDR2, and LC CDR3, and wherein
- (i) HC CDR1 is SEQ ID NO. 39, HC CDR2 is SEQ ID NO. 49, HC CDR3 is SEQ ID NO. 51, LC CDR1 is SEQ ID NO. 61, LC CDR2 is SEQ ID NO. 86, and LC CDR3 is SEQ ID NO. 87;
- (ii) HC CDR1 is SEQ ID NO. 30, HC CDR2 is SEQ ID NO. 43, HC CDR3 is SEQ ID NO. 25, LC CDR1 is SEQ ID NO. 64, LC CDR2 is SEQ ID NO. 27, and LC CDR3 is SEQ ID NO. 89;
- (iii) HC CDR1 is SEQ ID NO. 23, HC CDR2 is SEQ ID NO. 24, HC CDR3 is SEQ ID NO. 55, LC CDR1 is SEQ ID NO. 67, LC CDR2 is SEQ ID NO. 77, and LC CDR3 is SEQ ID NO. 92;
- (iv) HC CDR1 is SEQ ID NO. 31, HC CDR2 is SEQ ID NO. 42, HC CDR3 is SEQ ID NO. 60, LC CDR1 is SEQ ID NO. 64, LC CDR2 is SEQ ID NO. 79, and LC CDR3 is SEQ ID NO. 91;
- (v) HC CDR1 is SEQ ID NO. 35, HC CDR2 is SEQ ID NO. 46, HC CDR3 is SEQ ID NO. 56, LC CDR1 is SEQ ID NO. 68, LC CDR2 is SEQ ID NO. 75, and LC CDR3 is SEQ ID NO. 28;
- (vi) HC CDR1 is SEQ ID NO. 32, HC CDR2 is SEQ ID NO. 47, HC CDR3 is SEQ ID NO. 56, LC CDR1 is SEQ ID NO. 65, LC CDR2 is SEQ ID NO. 80, and LC CDR3 is SEQ ID NO. 87;
- (vii) HC CDR1 is SEQ ID NO. 29, HC CDR2 is SEQ ID NO. 44, HC CDR3 is SEQ ID NO. 52, LC CDR1 is SEQ ID NO. 73, LC CDR2 is SEQ ID NO. 76, and LC CDR3 is SEQ ID NO. 28;
- (viii) HC CDR1 is SEQ ID NO. 33, HC CDR2 is SEQ ID NO. 48, HC CDR3 is SEQ ID NO. 57, LC CDR1 is SEQ ID NO. 69, LC CDR2 is SEQ ID NO. 74, and LC CDR3 is SEQ ID NO. 28;
- (ix) HC CDR1 is SEQ ID NO. 38, HC CDR2 is SEQ ID NO. 24, HC CDR3 is SEQ ID NO. 25, LC CDR1 is SEQ ID NO. 62, LC CDR2 is SEQ ID NO. 81, and LC CDR3 is SEQ ID NO. 28;
- (x) HC CDR1 is SEQ ID NO. 37, HC CDR2 is SEQ ID NO. 24, HC CDR3 is SEQ ID NO. 53, LC CDR1 is SEQ ID NO. 70, LC CDR2 is SEQ ID NO. 82, and LC CDR3 is SEQ ID NO. 88;
- (xi) HC CDR1 is SEQ ID NO. 34, HC CDR2 is SEQ ID NO. 47, HC CDR3 is SEQ ID NO. 56, LC CDR1 is SEQ ID NO. 68, LC CDR2 is SEQ ID NO. 75, and LC CDR3 is SEQ ID NO. 28;
- (xii) HC CDR1 is SEQ ID NO. 29, HC CDR2 is SEQ ID NO. 24, HC CDR3 is SEQ ID NO. 54, LC CDR1 is SEQ ID NO. 71, LC CDR2 is SEQ ID NO. 83, and LC CDR3 is SEQ ID NO. 28;
- (xiii) HC CDR1 is SEQ ID NO. 33, HC CDR2 is SEQ ID NO. 41, HC CDR3 is SEQ ID NO. 25, LC CDR1 is SEQ ID NO. 63, LC CDR2 is SEQ ID NO. 84, and LC CDR3 is SEQ ID NO. 90;
- (xiv) HC CDR1 is SEQ ID NO. 30, HC CDR2 is SEQ ID NO. 44, HC CDR3 is SEQ ID NO. 58, LC CDR1 is SEQ ID NO. 66, LC CDR2 is SEQ ID NO. 85, and LC CDR3 is SEQ ID NO. 28;
- (xv) HC CDR1 is SEQ ID NO. 94, HC CDR2 is SEQ ID NO. 45, HC CDR3 is SEQ ID NO. 56, LC CDR1 is SEQ ID NO. 26, LC CDR2 is SEQ ID NO. 78, and LC CDR3 is SEQ ID NO. 93; or
- (xvi) HC CDR1 is SEQ ID NO. 36, HC CDR2 is SEQ ID NO. 50, HC CDR3 is SEQ ID NO. 59, LC CDR1 is SEQ ID NO. 72, LC CDR2 is SEQ ID NO. 75, and LC CDR3 is SEQ ID NO. 28.

* * * * *

UNITED STATES PATENT AND TRADEMARK OFFICE
CERTIFICATE OF CORRECTION

| | | |
|---|---|---|
| PATENT NO. | : 11,623,958 B2 | Page 1 of 1 |
| APPLICATION NO. | : 16/773806 | |
| DATED | : April 11, 2023 | |
| INVENTOR(S) | : Robert B. Dubridge et al. | |

It is certified that error appears in the above-identified patent and that said Letters Patent is hereby corrected as shown below:

In the Claims

In Column 107, Line 30, Claim 1, delete "and"

In Column 107, Lines 30 and 31, Claim 1, after "linker," delete "wherein the protein further comprises" and add -- and --

In Column 109, Line 6, Claim 12, replace "CDR1" with -- CDR3 --

In Column 109, Line 31, Claim 17, delete "selected from those" and replace "and" with -- or any one of --

In Column 110, Line 52, Claim 20 (xv), replace "or" with -- and --

In Column 111, Line 9, Claim 24, after "wherein" add -- the --

In Column 111, Line 11, Claim 24, after "wherein" add -- the --

Signed and Sealed this
Third Day of October, 2023

*Katherine Kelly Vidal*

Katherine Kelly Vidal
*Director of the United States Patent and Trademark Office*